(12) United States Patent
Dumont et al.

(10) Patent No.: US 12,257,288 B2
(45) Date of Patent: Mar. 25, 2025

(54) METHODS OF INDUCING IMMUNE TOLERANCE TO CLOTTING FACTORS

(71) Applicants: BIOVERATIV THERAPEUTICS INC., Waltham, MA (US); SWEDISH ORPHAN BIOVITRUM AB, Stockholm (SE)

(72) Inventors: Jennifer Dumont, Waltham, MA (US); Nisha Jain, Waltham, MA (US); Stefan Lethagen, Stockholm (SE)

(73) Assignees: BIOVERATIV THERAPEUTICS INC., Waltham, MA (US); SWEDISH ORPHAN BIOVITRUM AB, Stockholm (SE)

( * ) Notice: Subject to any disclaimer, the term of this patent is extended or adjusted under 35 U.S.C. 154(b) by 529 days.

(21) Appl. No.: 16/464,105

(22) PCT Filed: Dec. 1, 2017

(86) PCT No.: PCT/US2017/064323
§ 371 (c)(1),
(2) Date: May 24, 2019

(87) PCT Pub. No.: WO2018/102760
PCT Pub. Date: Jun. 7, 2018

(65) Prior Publication Data
US 2020/0085915 A1 Mar. 19, 2020

Related U.S. Application Data

(60) Provisional application No. 62/582,829, filed on Nov. 7, 2017, provisional application No. 62/558,790, filed on Sep. 14, 2017, provisional application No. 62/529,866, filed on Jul. 7, 2017, provisional application No. 62/466,937, filed on Mar. 3, 2017, provisional application No. 62/429,516, filed on Dec. 2, 2016.

(51) Int. Cl.
*A61K 38/37* (2006.01)
*A61K 38/48* (2006.01)
*A61P 7/04* (2006.01)

(52) U.S. Cl.
CPC .......... *A61K 38/37* (2013.01); *A61K 38/4846* (2013.01); *A61P 7/04* (2018.01); *C12Y 304/21022* (2013.01); *C07K 2319/21* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,695,199 A | 9/1987 | Goodacre et al. |
| 4,704,362 A | 11/1987 | Itakura et al. |
| 4,757,006 A | 7/1988 | Toole et al. |
| 4,800,159 A | 1/1989 | Mullis et al. |
| 4,868,112 A | 9/1989 | Toole, Jr. |
| 4,965,188 A | 10/1990 | Mullis et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Ooyen et al. |
| 5,364,771 A | 11/1994 | Lollar et al. |
| 5,543,502 A | 8/1996 | Nordfang et al. |
| 5,595,886 A | 1/1997 | Chapman et al. |
| 5,610,278 A | 3/1997 | Nordfang et al. |
| 5,648,260 A | 7/1997 | Winter et al. |
| 5,658,570 A | 8/1997 | Newman et al. |
| 5,712,122 A | 1/1998 | Boime et al. |
| 5,736,137 A | 4/1998 | Anderson et al. |
| 5,739,277 A | 4/1998 | Presta et al. |
| 5,789,203 A | 8/1998 | Chapman et al. |
| 5,834,250 A | 11/1998 | Wells et al. |
| 5,846,951 A | 12/1998 | Gregoriadis |
| 5,869,046 A | 2/1999 | Presta et al. |
| 5,972,885 A | 10/1999 | Spira et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |

(Continued)

FOREIGN PATENT DOCUMENTS

| | | |
|---|---|---|
| CA | 2863329 A1 | 7/2013 |
| EP | 0 154 316 A2 | 9/1985 |

(Continued)

OTHER PUBLICATIONS

Kempton, C.L. and White, G.C. Blood;13(1):11-17 (Year: 2009).*
(Jan. 2017) "ELOCTATE® Package Insert", Retrieved from: « http://worldwideweb.eloctate.com/_assets/pdf/ELOCTATE PI_January2017.pdf.».
(Feb. 28-Mar. 2, 2006) "Report of Expert Meeting on FVIII Products and Inhibitor Development", European Medicine Agency, 32 Pages.
Armour, et al. (Aug. 1999) "Recombinant Human IgG Molecules Lacking Fcgamma Receptor I Binding and Monocyte Triggering Activities", European Journal of Immunology, vol. 29, No. 8, pp. 2613-2624.

(Continued)

*Primary Examiner* — Michael Szperka
(74) *Attorney, Agent, or Firm* — LATHROP GPM LLP; James H. Velema, Esq.; James V. DeGiulio, Esq.

(57) ABSTRACT

The present disclosure provides methods inducing immune tolerance in a human, comprising administering to the human an effective amount of a composition or a chimeric protein comprising a clotting factor and an Fc region.

19 Claims, 15 Drawing Sheets

(56) References Cited

U.S. PATENT DOCUMENTS

| | | |
|---|---|---|
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,376,463 B1 | 4/2002 | Lollar et al. |
| 6,413,777 B1 | 7/2002 | Reff et al. |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,737,056 B1 | 5/2004 | Presta |
| 6,821,505 B2 | 11/2004 | Ward |
| 6,998,253 B1 | 2/2006 | Presta et al. |
| 7,041,635 B2 | 5/2006 | Kim et al. |
| 7,083,784 B2 | 8/2006 | Dall'acqua et al. |
| 7,199,223 B2 | 4/2007 | Bossard et al. |
| 7,317,091 B2 | 1/2008 | Lazar et al. |
| 7,348,004 B2 | 3/2008 | Peters et al. |
| 7,381,408 B2 | 6/2008 | Mezo et al. |
| 7,404,956 B2 | 7/2008 | Peters et al. |
| 7,632,921 B2 | 12/2009 | Pan et al. |
| 7,820,162 B2 | 10/2010 | Mezo et al. |
| 7,862,820 B2 | 1/2011 | Peters et al. |
| 8,329,182 B2 | 12/2012 | Peters et al. |
| 8,759,293 B2 | 6/2014 | Barnett |
| 8,815,250 B2 | 8/2014 | Rivera et al. |
| 8,932,830 B2 | 1/2015 | Peters et al. |
| 9,050,318 B2 | 6/2015 | Dumont et al. |
| 9,233,145 B2 | 1/2016 | Pierce et al. |
| 9,241,978 B2 | 1/2016 | Dumont et al. |
| 9,266,145 B2 | 2/2016 | Maurer et al. |
| 9,623,091 B2 | 4/2017 | Pierce et al. |
| 9,629,903 B2 | 4/2017 | Pierce et al. |
| 9,636,416 B2 | 5/2017 | Peters et al. |
| 9,670,475 B2 | 6/2017 | Pierce et al. |
| 9,675,676 B2 | 6/2017 | Pierce et al. |
| 9,867,873 B2 | 1/2018 | Pierce et al. |
| 10,221,455 B2 | 3/2019 | Jiang et al. |
| 10,391,152 B2 | 8/2019 | Jiang et al. |
| 10,568,943 B2 | 2/2020 | Pierce et al. |
| 10,745,680 B2 | 8/2020 | Liu et al. |
| 10,881,742 B2 | 1/2021 | Dumont et al. |
| 10,898,554 B1 | 1/2021 | Pierce et al. |
| 11,225,650 B2 | 1/2022 | Pierce et al. |
| 11,266,720 B2 | 3/2022 | Dumont et al. |
| 11,286,528 B2 | 3/2022 | Jiang et al. |
| 11,642,398 B2 | 5/2023 | Brader et al. |
| 2002/0038002 A1 | 3/2002 | Zaghouani et al. |
| 2003/0211113 A1 | 11/2003 | Kakkis et al. |
| 2003/0235536 A1 | 12/2003 | Blumberg et al. |
| 2004/0096456 A1 | 5/2004 | Conti-Fine et al. |
| 2004/0110929 A1 | 6/2004 | Bjorn et al. |
| 2005/0100990 A1 | 5/2005 | Saenko et al. |
| 2005/0147618 A1 | 7/2005 | Rivera et al. |
| 2005/0260194 A1 | 11/2005 | Peters et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2009/0087411 A1 | 4/2009 | Fares et al. |
| 2009/0163699 A1 | 6/2009 | Chamberlain et al. |
| 2009/0264627 A1 | 10/2009 | Gillies et al. |
| 2010/0239554 A1 | 9/2010 | Schellenberger et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0159540 A1 | 6/2011 | Mezo et al. |
| 2011/0172146 A1 | 7/2011 | Schellenberger et al. |
| 2011/0182896 A1 | 7/2011 | Rivera et al. |
| 2011/0268737 A1 | 11/2011 | Favier et al. |
| 2012/0142593 A1 | 6/2012 | Zhao et al. |
| 2013/0108629 A1 | 5/2013 | Dumont et al. |
| 2013/0171175 A1 | 7/2013 | Pierce et al. |
| 2013/0202595 A1 | 8/2013 | Pierce et al. |
| 2013/0274194 A1 | 10/2013 | Dumont et al. |
| 2014/0308280 A1 | 10/2014 | Maloney et al. |
| 2014/0370035 A1* | 12/2014 | Jiang ............... A61P 1/02 424/178.1 |
| 2015/0023959 A1 | 1/2015 | Chhabra et al. |
| 2015/0158929 A1 | 6/2015 | Schellenberger et al. |
| 2015/0252345 A1 | 9/2015 | Pierce et al. |
| 2015/0266943 A1 | 9/2015 | Chhabra et al. |
| 2015/0266944 A1 | 9/2015 | Jiang et al. |
| 2016/0199455 A1 | 7/2016 | Dumont et al. |
| 2016/0257943 A1 | 9/2016 | Pierce et al. |
| 2016/0346365 A1 | 12/2016 | Pierce et al. |
| 2017/0226189 A1 | 8/2017 | Peters et al. |
| 2017/0266309 A1 | 9/2017 | Peters et al. |
| 2019/0241960 A1 | 8/2019 | Jiang et al. |

FOREIGN PATENT DOCUMENTS

| | | |
|---|---|---|
| EP | 0295597 A2 | 12/1988 |
| EP | 0 401 384 A1 | 12/1990 |
| EP | 2 173 890 A1 | 4/2010 |
| EP | 2184070 A1 | 5/2010 |
| EP | 2802668 A1 | 11/2014 |
| EP | 3453402 A1 | 3/2019 |
| EP | EP 3 548 063 A1 | 10/2019 |
| JP | 2005-530762 A | 10/2005 |
| JP | 2007-500744 A | 1/2007 |
| JP | 2011-505414 A | 2/2011 |
| JP | 2011-523663 A | 8/2011 |
| JP | 2012-507994 A | 4/2012 |
| JP | 2012-522490 A | 9/2012 |
| JP | 2013-510581 A | 3/2013 |
| JP | 2013-512678 A | 4/2013 |
| JP | 2017-149784 A | 8/2017 |
| WO | WO 1987/004187 A1 | 7/1987 |
| WO | WO 1988/000831 A1 | 2/1988 |
| WO | WO 1988/003558 A1 | 5/1988 |
| WO | WO 1988/007089 A1 | 9/1988 |
| WO | WO 1988/008035 A1 | 10/1988 |
| WO | WO 1991/009122 A1 | 6/1991 |
| WO | WO 1992/016221 A1 | 10/1992 |
| WO | WO 1993/020093 A1 | 10/1993 |
| WO | WO 1994/011503 A2 | 5/1994 |
| WO | WO 1995/034326 A1 | 12/1995 |
| WO | WO 1996/014339 A1 | 5/1996 |
| WO | WO 1998/005787 A1 | 2/1998 |
| WO | WO 1998/023289 A1 | 6/1998 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2002/044215 A2 | 6/2002 |
| WO | WO 2002/060919 A2 | 8/2002 |
| WO | WO 2003/074569 A2 | 9/2003 |
| WO | WO 2003/077834 A2 | 9/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/099249 A2 | 11/2004 |
| WO | WO 2004/101739 A2 | 11/2004 |
| WO | WO 2004/101740 A2 | 11/2004 |
| WO | WO 2005/001025 A2 | 1/2005 |

(56) References Cited

FOREIGN PATENT DOCUMENTS

| | | |
|---|---|---|
| WO | WO 2005/040217 A2 | 5/2005 |
| WO | WO 2005/047327 A2 | 5/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/074199 A1 | 7/2006 |
| WO | WO 2006/085967 A2 | 8/2006 |
| WO | WO 2007/021494 A2 | 2/2007 |
| WO | WO 2008/033413 A2 | 3/2008 |
| WO | WO 2008/155134 A1 | 12/2008 |
| WO | WO 2009/058322 A1 | 5/2009 |
| WO | WO 2009/071886 A1 | 6/2009 |
| WO | WO 2009/149303 A1 | 12/2009 |
| WO | WO 2010/006635 A1 | 1/2010 |
| WO | WO 2010/052228 A1 | 5/2010 |
| WO | WO 2010/091122 A1 | 8/2010 |
| WO | WO 2010/111414 A1 | 9/2010 |
| WO | WO 2010/144502 A2 | 12/2010 |
| WO | WO 2010/144508 A1 | 12/2010 |
| WO | WO 2011/028228 A1 | 3/2011 |
| WO | WO 2011/028229 A1 | 3/2011 |
| WO | WO 2011/028344 A2 | 3/2011 |
| WO | WO 2011/060242 A2 | 5/2011 |
| WO | WO-2011069164 A2 * | 6/2011 ............ A61K 38/37 |
| WO | WO 2012/006623 A2 | 1/2012 |
| WO | WO-2013009627 A2 * | 1/2013 ............ A61K 38/37 |
| WO | WO-2013106789 A1 * | 7/2013 ............ A61K 38/21 |
| WO | WO 2015/106052 A1 | 7/2015 |
| WO | WO 2018/102760 A1 | 6/2018 |

OTHER PUBLICATIONS

Astermark, et al. (Dec. 1, 2006) "Polymorphisms in the TNFA Gene and the Risk of Inhibitor Development in Patients with Hemophilia A", Hemostasis, Thrombosis, and Vascular Biology, Blood, vol. 108, No. 12, pp. 3739-3745.
Bai, et al. (May 17, 2005) "Recombinant Granulocyte Colony-Stimulating Factor-Transferrin Fusion Protein as An Oral Myelopoietic Agent", Proceedings of the National Academy of Sciences of the United States of America, vol. 102, No. 20, pp. 7292-7296.
Batsuli, et al. (Apr. 26, 2016) "Innovating Immune Tolerance Induction for Haemophilia", Haemophilia, vol. 22, Suppl. 5, pp. 31-35.
Benhar, et al. (Dec. 1994) "Cloning, Expression and Characterization of The Fv Fragments of The Anti-Carbohydrate mAbs BI and B5 As Single-Chain Immunotoxins", Protein Engineering, Design and Selection, vol. 7, No. 12, pp. 1509-1515.
Bovenschen, et al. (2005) "LDL Receptor Cooperates with LDL Receptor-Related Protein in Regulating Plasma Levels of Coagulation Factor VIII In vivo", Blood, vol. 106, pp. 906-912.
Bovenschen, Niels (2010) "LDL Receptor Polymorphisms Revisited", Blood, vol. 116, No. 25, pp. 5439-5440.
Brandsma, et al. (Mar.-Apr. 2011) "Recombinant Human Transferrin: Beyond Iron Binding and Transport", Biotechnology Advances, vol. 29, No. 2, pp. 230-238.
Burmeister, et al. (Nov. 24, 1994) "Crystal Structure of The Complex of Rat Neonatal Fc Receptor with Fc", Nature, vol. 372, No. 6504, pp. 379-383.
Cameron, et al. (Feb. 1998) "The Canine Factor VIII cDNA and 5' Flanking Sequence", Journal of Thrombosis and Haemostasis, vol. 79, No. 2, pp. 317-322.
Capon, et al. (Feb. 9, 1989) "Designing CD4 Immunoadhesins For AIDS Therapy", Nature, vol. 337, No. 6207, pp. 525-531.
Dennis, et al. (Sep. 20, 2002) "Albumin Binding as a General Strategy for Improving the Pharmacokinetics of Proteins", Journal of Biological Chemistry, vol. 277, No. 38, pp. 35035-35043.
Dobeli, et al. (1988) "Role of The Carboxy-Terminal Sequence on The Biological Activity of Human Immune Interferon (IFN-y)", Journal of Biotechnology, vol. 7, No. 3, pp. 199-216.

Eaton, et al. (Dec. 1986) "Construction and Characterization of an Active Factor VIII Variant Lacking the Central One-Third of the Molecule", Biochemistry, vol. 25, No. 26, pp. 8343-8347.
Francis, G E. (1992) "Protein Modification and Fusion Proteins", Focus on Growth Factors, vol. 3, No. 2, Mediscript, England, pp. 4-10.
Friend, et al. (Dec. 15, 1999) "Phase I Study of An Engineered Aglycosylated Humanized Cd3 Antibody in Renal Transplant Rejection1", Transplantation, vol. 68, Issue 11, pp. 1632-1637.
Groomes, et al. (May 2016) "Reduction of Factor VIII Inhibitor Titers During Immune Tolerance Induction with Recombinant Factor VIII-Fc Fusion Protein", Pediatric Blood & Cancer, vol. 63, Issue 5, pp. 922-924.
Ho, et al. (Apr. 15, 1989) "Site-Directed Mutagenesis by Overlap Extension Using the Polymerase Chain Reaction", Gene, vol. 77, No. 1, pp. 51-59.
Hoeben, et al. (1990) "Expression of Functional Factor Viii in Primary Human Skin Fibroblasts After Retrovirus-Mediated Gene Transfer", Journal of Biological Chemistry, vol. 265, No. 13, pp. 7318-7323.
Holstein, et al. (Oct. 15, 2016) "Current View and Outcome of ITI Therapy—A Change Over Time?", Thrombosis Research, vol. 148, pp. 38-44.
Israel, et al. (Sep. 1997) "Expression of The Neonatal Fc Receptor, FcRn, On Human Intestinal Epithelial Cells", Immunology, vol. 92, No. 1, pp. 69-74.
Kasuda, et al. (Aug. 2008) "Establishment of Embryonic Stem Cells Secreting Human Factor VIII for Cell-Based Treatment of Hemophilia A", Journal of Thrombosis and Haemostasis, vol. 6, No. 8, pp. 1352-1359.
Kim, et al. (Sep. 2010) "Transferrin Fusion Technology: a Novel Approach to Prolonging Biological Half-Life of Insulinotropic Peptides", Journal of Pharmacology and Experimental Therapeutics, vol. 334, No. 3, pp. 682-692.
Kobayashi, et al. (Feb. 2002) "FcRn-Mediated Transcytosis of Immunoglobulin G in Human Renal Proximal Tubular Epithelial Cells", American Journal of Physiology-Renal Physiology, vol. 282, No. 2, pp. F358-F365.
Kraulis, et al. (Jan. 8, 1996) "The Serum Albumin-Binding Domain of Streptococcal Protein G is a Three-Helical Bundle: a Heteronuclear NMR Study", FEBS Letters, vol. 378, Issue 2, pp. 190-194.
Krishnamoorthy, et al. (Mar. 2016) "Recombinant Factor VIII Fc (rFVIIIFc) Fusion Protein Reduces Immunogenicity and Induces Tolerance in Hemophilia a Mice", Cellular Immunology, vol. 301, pp. 30-39.
Langner, et al. (Apr. 1988) "Synthesis of Biologically Active Deletion Mutants of Human Factor VIII:C", Behring Institute Mitteilungen, No. 82, pp. 16-25.
Larrick, et al. (1989) "Rapid Cloning of Rearranged Immunoglobulin Genes from Human Hybridoma Cells using Mixed Primers and the Polymerase Chain Reaction", Biochemical and Biophysical Research Communications, vol. 160, No. 3, pp. 1250-1256.
Lenting, et al. (May 2010) "The Disappearing Act of Factor VIII", Haemophilia, vol. 16, No. 102, pp. 6-15.
Li, et al. (May 2002) "The Role of The Transferrin-Transferrin-Receptor System in Drug Delivery and Targeting", Trends in Pharmacological Sciences, vol. 23, No. 5, pp. 206-209.
Linhult, et al. (Feb. 2002) "Mutational Analysis of The Interaction Between Albumin-Binding Domain from Streptococcal Protein G and Human Serum Albumin", Protein Science, vol. 11, No. 2, pp. 206-213.
Malec, et al. (Nov. 2016) "Extended Half-Life Factor VIII for Immune Tolerance Induction in Haemophilia", Haemophilia, vol. 22, Issue 6, pp. e552-e554.
Malec, et al. (Dec. 2015) "Immune Tolerance Induction Using Rfviiifc (Eloctate)", Blood, vol. 126, No. 23, 57th Annual Meeting of the American-Society-of-Hematology, pp. 1-2.
Malik, et al. (Sep. 1992) "Polyethylene Glycol (PEG)-Modified Granulocyte-Macrophage Colony-Stimulating Factor (GM-CSF) With Conserved Biological Activity", Experimental Hematology, vol. 20, No. 8, pp. 1028-1035.

(56) References Cited

OTHER PUBLICATIONS

Mannucci, et al. (Jun. 1, 2001) "The Hemophilias—From Royal Genes to Gene Therapy", New England Journal of Medicine, vol. 344, No. 23, pp. 1773-1779.
Martinelli, et al. (2010) "Polymorphisms at LDLR Locus May Be Associated with Coronary Artery Disease Through Modulation of Coagulation Factor VIII Activity and Independently from Lipid Profile", Blood, vol. 116, pp. 5688-5697.
Mei, et al. (Jul. 15, 2010) "Rational Design of a Fully Active, Long-Acting PEGylated Factor VIII for Hemophilia A Treatment", Blood, vol. 116, No. 2, pp. 270-279.
Meulien, et al. (1988) "A New Recombinant Procoagulant Protein Derived from the cDNA Encoding Human Factor Viii", Protein Engineering, Design and Selection, vol. 2, No. 4, pp. 301-306.
Miao, et al. (May 1, 2004) "Bioengineering of Coagulation Factor VIII for Improved Secretion", Blood, vol. 103, No. 9, pp. 3412-3419.
Peyvandi, et al. (Jul. 2006) "Genetic Diagnosis of Haemophilia and Other Inherited Bleeding Disorders", Haemophilia, vol. 12, Suppl 3, pp. 82-89.
Pipe, et al. (2011) "Functional Factor VIII Made with Von Willebrand Factor at High Levels in Transgenic Milk", Journal of Thrombosis and Haemostasis, vol. 9, No. 11, pp. 2235-2242.
Ragni, et al. (Sep. 2016) "Inhibitor Development in Two Cousins Receiving Full-Length Factor Viii (Fviii) and FVIII-Fc Fusion Protein", Hemophilia, vol. 22, Issue 5, pp. e462-e464.
Rodriguez-Merchan, et al. (2002) "Inhibitors in Patients with Hemophilia", Blackwell Science, Ltd.
Ron, et al. (1993) "Expression of Biologically Active Recombinant Keratinocyte Growth Factor. Structure/Function Analysis of Amino-Terminal Truncation Mutants", Journal of Biological Chemistry, vol. 268, No. 4, pp. 2984-2988.
Roth, et al. (1993) "Expression of Polysialic Acid in Human Tumors and Its Significance for Tumor Growth", Polysialic Acid: From Microbes to Man, pp. 335-348.
Routledge, et al. (Oct. 1, 1995) "The Effect of Aglycosylation on the Immunogenicity of a Humanized Therapeutic CD3 Monoclonal Antibody", Transplantation, vol. 60, No. 8, pp. 847-853.
Ruberti, et al. (Jul. 12, 1994) "The Use of The RACE Method to Clone Hybridoma cDNA When V Region Primers Fail", Journal of Immunological Methods, vol. 173, No. 1, pp. 33-39.
Sarver, et al. (Dec. 1987) "Stable Expression of Recombinant Factor Viii Molecules Using A Bovine Papillomavirus Vector", DNA, vol. 6, No. 6, pp. 553-564.
Schlapschy, et al. (Jun. 1, 2007) "Fusion of A Recombinant Antibody Fragment with A Homo-Amino-Acid Polymer: Effects on Biophysical Properties and Prolonged Plasma Half-Life", Protein Engineering, Design and Selection, vol. 20, No. 6, pp. 273-284.
Shields, et al. (Mar. 2, 2001) "High Resolution Mapping of The Binding Site on Human IgG1 for Fc Gamma RI, Fc Gamma RII, Fc Gamma RIII, and FcRn and Design of IgG1 Variants with Improved Binding to The Fc Gamma R", Journal of Biological Chemistry, vol. 276, No. 9, pp. 6591-6604.
Story, et al. (Dec. 1, 1994) "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381.
Toole, et al. (Aug. 1986) "A Large Region (Approximately Equal to 95 kDa) Of Human Factor VIII is Dispensable for In Vitro Procoagulant Activity", Proceedings of the National Academy of Sciences, vol. 83, No. 16, pp. 5939-5942.
Wang, et al. (Nov. 7, 2011) "Receptor-Mediated Activation of a Proinsulin-Transferrin Fusion Protein in Hepatoma Cells", Journal of Controlled Release, vol. 155, No. 3, pp. 386-392.
Ward, et al. (Apr. 1995) "The Effector Functions of Immunoglobulins: Implications for Therapy", Therapeutic immunology, vol. 2, No. 2, pp. 77-94.
Cutler, et al. (2002) "The Identification and Classification of 41 Novel Mutations in The Factor VIII Gene (F8c)", Human Mutation, vol. 19, No. 3, pp. 274-278.

Genbank, "*Homo sapiens* Transferrin (TF), mRNA," Accession No. XM002793, accessed at https://www.ncbi.nlm.nih.gov/nuccore/XM_002793.7?report=genbank, accessed on Jan. 1, 2018, 2 pages.
Genbank, "*Homo sapiens* transferrin (TF), mRNA," Accession No. XM039845, accessed at https://www.ncbi.nlm.nih.gov/nuccore/XM_039845.1?report=genbank, accessed on Jan. 1, 2018, 2 pages.
Genbank, "*Homo sapiens* transferrin (TF), mRNA," Accession No. XM039847, accessed at https://www.ncbi.nlm.nih.gov/nuccore/XM_039847.1?report=genbank, accessed on Jan. 1, 2018, 2 pages.
Genbank, "*Homo sapiens* transferrin (TF), transcript variant 1. mRNA," Accession No. NM001063, accessed at https://www.ncbi.nlm.nih.gov/nuccore/NM_001063, accessed on Jan. 1, 2018, 5 pages.
Genbank, "Human transferrin mRNA, complete cds," Accession No. M12530, accessed at https://www.ncbi.nlm.nih.gov/nuccore/339452/, accessed on Jan. 1, 2018, 2 pages.
Genbank, "Transferrin [human, liver, mRNA, 2347 nt]," Accession No. S95936, accessed at https://www.ncbi.nlm.nih.gov/nuccore/595936, accessed on Jan. 1, 2018, 2 pages.
Holt, et al. (May 2008) "Anti-Serum Albumin Domain Antibodies for Extending the Half-Lives of Short Lived Drugs", Protein Engineering, Design and Selection, vol. 21, No. 5, pp. 283-288.
Horton, et al. (1993) "Gene Splicing by Overlap Extension", Methods in Enzymology, vol. 217, pp. 270-279.
International Search Report & Written Opinion Received for PCT Application No. PCT/US2017/064323, mailed on Mar. 28, 2018.
Lillicrap, "Extending half-life in coagulation factors: where do we stand?", Thrombosis Research. 2008, 122(Suppl. 4): S2-S8.
Muller, et al. (Aug. 2007) "Recombinant Bispecific Antibodies for Cellular Cancer Immunotherapy", Current opinion in molecular therapeutics, vol. 9, No. 4, pp. 319-326.
Oldenburg et al., "Primary and rescue immune tolerance induction in children and adults: a multicentre international study with a VWF-containing plasma-derived FVIII concentrate", Haemophilia, 2014, 20: 83-91.
Roovers, et al. (Mar. 2007) "Efficient Inhibition of EGFR Signaling and of Tumour Growth by Antagonistic anti-EFGR Nanobodies", Cancer Immunology, Immunotherapy, vol. 56, No. 3, pp. 303-317.
Sommermeyer, et al. (1987) "Klinisch Verwendete Hydroxyethylstärke: Physikalischchemische Charakterisierung", Krankenhauspharmazie, vol. 8, No. 8, Deutscher Apotheker Verlag, Birkenwaldstr, Germany, pp. 271-278.
Trussel, et al. (Dec. 2009) "New Strategy for The Extension of The Serum Half-Life of Antibody Fragments", Bioconjugate Chemistry, vol. 20, No. 12, pp. 2286-2292.
Weidler, et al. (May 1991) "Pharmacokinetic Parameters as Criteria for Clinical Use of Hydroxyethyl Starch Preparations", Arzneimittelforschung/Drug Research, vol. 41, No. 5, pp. 494-498.
Akilesh, et al., "Neonatal FcR Expression in Bone Marrow-Derived Cells Functions to Protect Serum IgG from Catabolism," The Journal of Immunology 179(7):4580-4588, The American Association of Immunologists, Inc., United States (2007).
Aledort, et al., "A longitudinal study of orthopaedic outcomes for severe factor-VIII deficient haemophiliacs," Journal of Internal Medicine 236(4):391-399, Blackwell Scientific Publications, England (1994).
Armour, et al., "Recombinant human IgG molecules lacking Fcγ receptor I binding and monocyte triggering activities," European Journal of Immunology 29(8):2613-2624, Wiley-VCH Verlag GmbH, Germany (1999).
Astermark et al., "Polymorphisms in the CTLA-4 gene and inhibitor development in patients with severe hemophilia A," Journal of Thrombosis and Haemostasis 5(2):263-265, International Society on Thrombosis and Haemostasis, England (2007).
Astermark et al., "Polymorphisms in the IL10 but not in the IL1beta and IL4 genes are associated with inhibitor development in patients with hemophilia A," Blood 107(8):3167-3172, The American Society of Hematology, United States (2006).
Astermark et al., (2005) "The Malmö International Brother Study (MIBS): Genetic defects and inhibitor development in siblings with severe hemophilia A", Haematologica, 90(7): 924-931.

(56) References Cited

OTHER PUBLICATIONS

Astermark et al., "The Malmö International Brother Study (MIBS): further support for genetic predisposition to inhibitor development in hemophilia patients", Haemophilia, May 2001, 7(3): 267-272.
Astermark, "Immune tolerance induction in patients with haemophilia A", Thromb Res, Jan. 2011, 127(Suppl 1): S6-S9, Epublished Nov. 5, 2010.
Astermark, et al., "Basic Aspects of Inhibitors to Factors VIII and IX and the Influence of Non-Genetic Risk Factors", J. Haemophilia, vol. 12, Supplement 6, pp. 8-13, Dec. 2006.
Aznar, et al., "The orthopaedic status of severe haemophiliacs in Spain," Haemophilia 6(3):170-176, Blackwell Science, England (2000).
Bajaj et al., "Redetermination of the Rate-Limiting Step in the Activation of Factor IX by Factor XIa and by Factor VIIa/Tissue Factor. Explanation for Different Electrophoretic Radioactivity Profiles Obtained on Activation of 3H- and 125I-Labeled Factor IX," Biochemistry 22(17):4047-4053, American Chemical Society, United States (1983).
Bi et al., "Targeted Disruption of the Mouse Factor VIII Gene Produces a Model of Haemophilia A," Nature Genetics 10(1):119-121, Nature Publishing Co., United States (1995).
Bitonti et al., "Pulmonary delivery of an erythropoietin Fc fusion protein in non-human primates through an immunoglobulin transport pathway," Proceedings of the National Academy of Sciences USA 101(26):9763-9768, The National Academy of Sciences, United States (2004).
Borvak et al., "Functional Expression of the MHC Class I-related Receptor, FcRn, in Endothelial Cells of Mice," International Immunology 10(9):1289-1298, Oxford University Press, i England (1998).
Brandstetter et al., "X-ray structure of clotting factor IXa: active site and module structure related to Xase activity and hemophilia B," Proceedings of the National Academy of Sciences USA 92(21):9796-9800, The National Academy of Sciences, United States (1995).
Brunetti-Pierri et al., "Bioengineered factor IX molecules with increased catalytic activity improve the therapeutic index of gene therapy vectors for hemophilia B," Human Gene Therapy 20(5):479-485, Mary Ann Liebert. Inc., United States (2009).
Brutlag et al., "Improved sensitivity of biological sequence database searches," Computer Applications in the Biosciences 6(3):237-245, Oxford University Press, England (1990).
Butenas et al., "Blood coagulation," Biochemistry (Moscow) 67(1):3-12, MAIK Nauka/Interperiodica, United States (2002).
Callaghan et al., "Immune tolerance induction in 31 children with haemophilia A: is ITI less successful in African Americans?", Haemophilia, May 2011, 17(3): 483-489, Epublished Dec. 1, 2010.
Cao, et al., "Role of regulatory T cells in tolerance to coagulation factors," Journal of Thrombosis and Haemostasis 7(Suppl 1):88-91, Blackwell Publishing, England (2009).
Castaman, G., et al., "Pregnancy and Delivery in Women with Von Willebrand's Disease and Different Von Willebrand Factor Mutations," Haematologica 95(6):963-969, Ferrata Storti Foundation, Italy (2010).
Chang, J., et al., "Changing Residue 338 in Human Factor IX from Arginine to Alanine Causes an Increase in Catalytic Activity," The Journal of Biological Chemistry 273(20):12089-12094, The American Society for Biochemistry and Molecular Biology, Inc., United States (1998).
Coppola et al., (2009) "Factor VIII gene (F8) mutations as predictors of outcome in immune tolerance induction of hemophilia A patients with high-responding inhibitors", J Thromb Haemost, 7(11): 1809-1815, doi: 10.1111/j.1538-7836.2009.03615.x.
Coppola, A., et al., "Primary Prophylaxis in Children with Haemophilia," Blood Transfusion Prophylaxis in Congenital Coagulation Disorders 6(Suppl 2):s4-s11, Society of Transfusion Medicine and Immunohaematology, Italy (2008).
Damiano et al., (2000) "Immune tolerance for haemophilia patients with inhibitors: analysis of the western United States experience", The Tri-Regional Nursing Group, Haemophilia, 6(5): 526-532.

De Groot, et al., "Activation of Natural Regulatory T Cells by IgG Fc-Derived Peptide 'Tregitopes'", Blood, vol. 112, No. 8, pp. 3303-3311, Oct. 15, 2008.
Delignant, "Transplacental Delivery of FC-Fused Recombinant Factor VIII ($_R$FVIIIFC) In FVIII-Deficient Mice", Centre de Recherche Des Cordeliers, Presented at EAHAD 2021 Virtual Congress, Session 7, Feb. 5, 2021, 15 pages.
Delignant, Abstract—"Transplacental Delivery of FC-Fused Factor VIII ($_R$FVIIIFC) in FVIII-Deficient Mice", Centre de Recherche Des Cordeliers, EAHAD 2021 Virtual Congress, Session 7, Feb. 5, 2021, 2 pages.
Dimichele et al., (2002) "The North American Immune Tolerance Registry: practices, outcomes, outcome predictors", Thromb Haemost, 87(1): 52-57.
Dimichele, (2009) "The North American Immune Tolerance Registry: contributions to the thirty-year experience with immune tolerance therapy", Haemophilia, 15(1): 320-328, doi:10.1111/j.1365-2516.2008.01880.x.
Dumont, J.A., et al., "Delivery of an Erythropoietin-Fc Fusion Protein by Inhalation in Humans through an Immunoglobulin Transport Pathway," Journal of Aerosol Medicine 18(3):294-303, May Ann Liebert, Inc., United States (2005).
Dumont, J.A., et al., "Factor VIII-Fc Fusion Protein Shows Extended Half-Life and Hemostatic Activity in Hemophilia A Dogs," ASH 51st Annual Meeting Abstracts 114(22): Abstract 545, The American Society of Hematology, United States (2009).
Dumont, J.A., et al., "Monomeric Fc Fusion Technology: An Approach to Create Long-Lasting Clotting Factors," in: Therapeutic Proteins- Strategies to Modulate Half-Life, Kontermann R., ed., Chapter 10, pp. 189-206, Wiley Blackwell, Germany (Mar. 26, 2012).
Dumont, J.A., et al., "Monomeric Fc Fusion: Impact on Pharmacokinetic and Biological Activity of Protein Therapeutics," BioDrugs 20(3): 151-160, Adis Data Information B.V., New Zealand (2006).
Dumont, J.A., et al., "Prolonged Activity of a Recombinant Factor VIII-Fc Fusion Protein in Hemophilia a Mice and Dogs," Blood 119(13):3024-3030, The American Society of Hematology, United States (Mar. 29, 2012).
Eckhardt, C.L., et al., "Surgery and inhibitor development in hemophilia A: a systematic review," Journal of Thrombosis and Haemostasis 9(10):1948-1958, Blackwell Publishing, England (Oct. 2011).
Eigenbrot, et al., "The Factor VII Zymogen Structure Reveals Reregistration of β Strands during Activation", Structure, vol. 9, No. 7, pp. 627-636, Jul. 3, 2001.
EMA European Medicines Agency, "Reflection Paper on Immune Tolerance Induction in haemophilia A patients with inhibitors", Committee for Medicinal Products for Human Use, Mar. 21, 2013.
English language Abstract of European Patent Publication No. EP 0295597 A2, European Patent Office, Espacenet database—Worldwide (1988).
Ettingshausen et al., "Early long-term FEIBA prophylaxis in haemophilia A patients with inhibitor after failing immune tolerance induction: A prospective clinical case series", Haemophilia, Jan. 2010, 16(1): 90-100.
Extended European Search Report for European Application No. 18183272.6, dated Feb. 13, 2019.
Fatouros, A., et al., "Recombinant factor VIII SQ influence of oxygen, metal ions, pH and ionic strength on its stability in aqueous solution," International Journal of Pharmaceutics 155(1):121-131, Elsevier, United States (1997).
Feagan, et al., "Ustekinumab as Induction and Maintenance Therapy for Crohn's Disease", New England Journal of Medicine, vol. 375, No. 20, pp. 1946-1960, Nov. 17, 2016.
Feldman, B.M., et al., "Tailored prophylaxis in severe hemophilia A: interim results from the first 5 years of the Canadian Hemophilia Primary Prophylaxis Study," Journal of Thrombosis and Haemostasis 4(6):1228-1236, Blackwell Publishing, England (2006).
Foster, P.A., et al., "Synthetic factor VIII peptides with amino acid sequences contained within the C2 domain of factor VIII inhibit factor VIII binding to phosphatidylserine," Blood 75(10):1999-2004, The American Society of Hematology, United States (1990),.

(56) References Cited

OTHER PUBLICATIONS

Franchini et al., (2011), "Immune tolerance induction for patients with severe hemophilia A: a critical literature review", J Thromb Thrombolysis, 32(4): 439-447, doi:10.1007/s11239-011-0624-3.

Franchini et al., (2013) "Systematic review of the role of FVIII concentrates in inhibitor development in previously untreated patients with severe hemophilia A: a 2013 update", Semin Thromb Hemost, 39(7): 752-766, doi: 10.1055/s-0033-1356715.

Freiburghaus, et al., "Tolerance Induction Using the Malmö Treatment Model 1982-1995", Haemophilia, vol. 5, No. 1, pp. 32-39, Jan. 1999.

Gayle, R.B., III., et al., "Identification of Regions in Interleukin-Iα Important for Activity," The Journal of Biological Chemistry 268(29):22105-22111, The American Society for Biochemistry and Molecular Biology, Inc., United States (1993).

GenBank, "Homo sapiens coagulation factor VIII, procoagulant component (F8), transcript variant 1, mRN A," Accession No. NM_000132.3, accessed at http://www.ncbi.nlm.nih.gov/nuccore/NM_000132.3, 2008, 12 pages.

GenBank, "Homo sapiens mRNA for immunoglobulin kappa heavy chain," Accession No. Y14735.1, accessed at http://www.ncbi.nlm.nih.gov/nuccore/Y14735, Aug. 19, 1998, 3 pages.

George, et al., "Profile of Efraloctocog Alfa and its Potential in the Treatment of Hemophilia A", Journal of Blood Medicine, vol. 6, pp. 131-141, Apr. 24, 2015.

Geraghty, S., et al., "Practice patterns in haemophilia A therapy—global progress towards optimal care," Haemophilia 12(1):75-81, Blackwell Publishing Ltd., England (2006).

Gitschier, J., et al., "Characterization of the human factor VIII gene," Nature 312(5992):326-330, Nature Publishing Group, England (1984).

Gouw et al., (2013), "Factor VIII products and inhibitor development in severe hemophilia A", N Engl J Med, 368(3): 231-239, doi: 10.1056/NEJMoa1208024.

Gouw et al., "Discordant antibody response in monozygotic twins with severe haemophilia A caused by intensive treatment", Haemophilia, May 2009, 15(3): 712-717.

Graham, J.B., et al., "Canine Hemophilia: Observations on the Course, the Clotting Anomaly, and the Effect of Blood Transfusions," The Journal of Experimental Medicine 90(2):97-111, The Rockefeller University Press, United States (1949).

Green, D., "Factor VIII inhibitors: a 50-year perspective," Haemophilia 17(6):831-838, Blackwell Publishing Ltd., England (Nov. 2011).

Gringeri et al., "Immune tolerance induction with high purity von Willebrand factor/VIII complex concentrate in haemophilia A patients with inhibitors at high risk of a poor response", Haemophilia, Jul. 2007, 13(4): 373-379.

Gringeri, (2007) "VWF/FVIII concentrates in high-risk immunotolerance: the RESIST study", Haemophilia, 13(Suppl 5): 73-77, doi:10.1111/j.1365-2516.2007.01579.x.

Grubb, J.H., et al., "Infused Fc-tagged β-glucuronidase crosses the placenta and produces clearance of storage in utero in mucopolysaccharidosis VII mice," Proceedings of the National Academy of Sciences USA 105(24)8375-8380, The National Academy of Sciences, United States (2008).

Gupta et al., (2015) "Regulation of immune responses to protein therapeutics by transplacental induction of T cell tolerance", Sci Transl Med, 7(275): 275ra221, doi:10.1126/scitranslmed.aaa1957.

Hacker, M.R., et al., "Barriers to compliance with prophylaxis therapy in haemophilia," Haemophilia 7(4):392-396, Blackwell Science, England (2001).

Hay et al., (2012) "The principal results of the International Immune Tolerance Study: a randomized dose comparison", Blood, 119(6): 1335-1344, doi:10.1182/blood-2011-08-369132.

Hay et al., "The diagnosis and management of factor VIII and IX inhibitors: a guideline from the United Kingdom Haemophilia Centre Doctors Organization," British Journal of Haematology 133(6):591-605, Blackwell Publishing, England (2006).

Haya et al., (2001) "Immune tolerance treatment in haemophilia patients with inhibitors: the Spanish Registry", Haemophilia, 7(2): 154-159.

Healey, J.F., et al., "The cDNA and derived amino acid sequence of porcine factor VIII," Blood 88(11):4209-4214, The American Society of Hematology, United States (1996).

Herzog, R.W., et al., "Long-term correction of canine hemophilia B by gene transfer of blood coagulation factor IX mediated by adeno-associated viral vector," Nature Medicine 5(1):56-63, Nature Publishing Co., United States (1999).

Huang, C., "Receptor-Fc Fusion Therapeutics Traps, and MIMETIBODYTM Technology," Current Opinion in Biotechnology 20(6):692-699, Current Biology, England (2009).

International Search Report and Written Opinion for International Application No. PCT/US2013/021332, mailed Mar. 18, 2013.

Ishiguro, "Immune Mechanisms Involved in the Development and Eradication of Anti-Factor VIII Alloantibodies in Hemophilia", Japanese Journal of Clinical Immunology, vol. 34, Issue 6, pp. 476-484, 2011.

Jimenez-Yuste et al., (2016) "Long-term outcome of haemophilia A patients after successful immune tolerance induction therapy using a single plasma-derived FVIII/VWF product: the long-term ITI study", Haemophilia, 22(6): 859-865, doi:10.1111/hae.12986.

Karpf, D.M., et al., "Preclinical pharmacokinetic (PK) evaluation of glycopegylated long acting RFVIII," Hemophilia 16(Suppl. 4):40 Blackwell Publishing Ltd., England (2010).

Kasper C.K., "Diagnosis and Management of Inhibitors to Factors VIII and IX: An Introductory Discussion for Physicians," Treatment of Hemophilia 34:1-22, World Federation of Hemophilia, Canada (2004).

Kau, et al., "Anti-Interleukin 4 and 13 for Asthma Treatment in the Era of Endotypes", Current Opinion in Allergy and Clinical Immunology, vol. 14, No. 6, pp. 570-575, Dec. 2014.

Kempton et al., (2014) "Toward optimal therapy for inhibitors in hemophilia", Blood, 124(23): 3365-3372, doi:10.1182/blood-2014-05-577643.

Kreuz et al., (2016) "First prospective report on immune tolerance in poor risk haemophilia A inhibitor patients with a single factor VIII/von Willebrand factor concentrate in an observational immune tolerance induction study", Haemophilia, 22(1): 87-95, doi:10.1111/hae.12774.

Kreuz, et al., "Immune Tolerance Therapy in Paediatric Haemophiliacs with Factor VIII Inhibitors: 14 Years Follow-up", Haemophilia, vol. 1, No. 1, pp. 24-32, Jan. 1, 1995.

Kreuz, W., et al., "When should prophylactic treatment in patients with haemophilia A and B start? —The German experience," Haemophilia 4(4):413-417, Blackwell Science Ltd., England (1998).

Kroner et al. (1999) "Comparison of the international immune tolerance registry and the North American immune tolerance registry", Vox Sang, 77(Suppl 1): 33-37.

Kurth et al., (2011) "The use of a single von Willebrand factor-containing, plasma-derived FVIII product in hemophilia A immune tolerance induction: the US experience", J Thromb Haemost, 9(11): 2229-2234, doi: 10.1111/j.1538-7836.2011.04493.x.

Lee, C.A., et al., "Pharmacokinetics of Recombinant Factor VIII (Recombinate) Using One- Stage Clotting and Chromogenic Factor VIII Assay," Thrombosis and Haemostasis 82(6):1644-1647, Schattauer Verlag, Germany (1999).

Lei, T.C., "Induction of tolerance to factor VIII inhibitors by gene therapy with immunodominant A2 and C2 domains presented by B cells as Ig fusion proteins," Blood 105(12):4865-4870, The American Society of Hematology, United States (2005).

Lencer, W.I. and Blumberg, R.S., "A passionate kiss, then run: exocytosis and recycling of IgG by FcRn," TRENDS in Cell Biology 15(1):5-9, Elsevier Science Publishers, England (2005).

Lenting, P.J., et al., "Clearance mechanisms of von Willebrand factor and factor VIII," Journal of Thrombosis and Haemostasis 5(7):1353-1360, Blackwell Publishing, England (2007).

Liesner, R.J., et al., "The impact of prophylactic treatment on children with severe haemophilia," British Journal of Haematology 92(4):973-978, Blackwell Publishing, England (1996).

(56) References Cited

OTHER PUBLICATIONS

Lillicrap, D., "Improvements in factor concentrates," Current Opinion in Hematology 17(5):393-397, Lippincott Williams & Wilkins, United States (2010).

Ling, et al., "Classification of the Kinetics of Factor VIII Inhibitors in Haemophilia A: Plasma Dilution Studies Are More Discriminatory Than Time-Course Studies", British Journal of Haematology, vol. 114, No. 4, pp. 861-867, Sep. 2001.

Liu, T. Z., et al. "Recombinant FVIII Fc fusion protein is fully active in treating acute injury and demonstrates prolonged prophylactic efficacy in hemophilia A mice," Journal of Thrombosis and Haemostasis 9(Supp.2):561, Abstract P-WE-131, Blackwell Publishing, United States (Jul. 2011).

Liu, T., et al., "Evaluation of antibody responses to rFVIIIFc compared to Xyntha® and Advate® in hemophilia A mice," Hemophilia 18(Suppl. 3):41, Blackwell Publishing Ltd., England (Jul. 9, 2012).

Liu, T., et al., "Site-Specific PEGylation of Factor VIII (PEG-FVIII) Preserves Full Clotting Activity and Extends Therapeutic Efficacy in Hemophilia A Dogs," 50th ASH Annual Meeting and Exposition Online Program and Abstracts:511, The American Society of Hematology, United States (2008).

Livak, K.J. and Schmittgen T.D., "Analysis of relative gene expression data using real-time quantitative PCR and the 2-ΔΔCT Method," Methods 25(4):402-408, Academic Press, United States (2001).

Ljung, R.C.R., "Prophylactic treatment in Sweden—overtreatment or optimal model?" Haemophilia 4(4):409-412, Blackwell Science Ltd., England (1998).

Löfqvist, et al., "Haemophilia Prophylaxis In Young Patients ± A Long-Term Follow-Up", Journal of Internal Medicine, vol. 241, pp. 395-400, 1997.

Lollar, P. and Parker, E.T., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (1991).

Lollar, P., et al., "Coagulant Properties of Hybrid Human/Porcine Factor VIII Molecules," Journal of Biological Chemistry 267(33):23652-23657, The American Society for Biochemistry and Molecular Biology, Inc., United States (1992).

Lozier, J.N., et al., "The Chapel Hill Hemophilia A Dog Colony Exhibits a Factor VIII Gene Inversion," Proceedings of the National Academy of Sciences USA 99(20):12991-12996, The National Academy of Sciences, United States (2002).

Manco-Johnson, M., et al., "Prophylaxis versus Episodic Treatment to Prevent Joint Disease in Boys with Severe Hemophilia," New England Journal of Medicine 357(6):535-544, Massachusetts Medical Society, United States (2007).

Mariani et al., "Immune tolerance induction in hemophilia A: a review", Semin Thromb Hemost., Feb. 2003, 29(1): 69-76.

McCue, J.T., et al., "Applicants of a Novel Affinity Adsorbent for the Capture and Purification of Recombinant Factor VIII Compounds," Journal of Chromatography A 1216(45):7824-7830, Elsevier, Netherlands (2009).

Meslier, Y., et al., "Induction of Tolerance to Therapeutic FVIII by Materno-Fetal Transfer in a Hemophilia A mouse model," European Journal Immunology 2009: Tuesday, Poster Sessions, abstract PD11/26, p. S536, Wiley-VCI-1 Verlag Gmbh & Co. KGaA, Germany (2009).

Metzner, H.J., et al., "Characterization of factor VIII/von Willebrand factor concentrates using a modified method of von Willebrand factor multimer analysis," Haemophilia 4(Suppl. 3):25-32, Blackwell Science Ltd., England (1998).

Metzner, H.J., et al., "Genetic fusion to albumin improves the pharmacokinetic properties of factor IX," Journal of Thrombosis and Haemostasis 102(4):634-644, Stuttgart, Schattauer, Germany (2009).

Mikaelsson, M. and Oswaldsson, U., "Assaying the Circulating Factor VIII Activity in Hemophilia A Patients Treated with Recombinant Factor VIII Products," Seminars in Thrombosis and Hemostasis 28(3):257-264, Thieme, United States (2002).

Molho, P., et al., "Epidemiological survey of the orthopaedic status of severe hemophilia A and B patients in France," Haemophilia 6(1):23-32, Blackwell Science Ltd., England (2000).

Morfini, M., "Pharmacokinetics of factor VIII and factor IX," Hemophilia 9(Suppl. 1):94-100, Blackwell Publishing Ltd., England (2003).

Møss, J., et al., "Safety and pharmacokinetic of a glycoPEGylated recombinant activated factor VIII derivative: a randomized first human dose trial in healthy subjects," Journal of Thrombosis and Haemostasis 9(7):1368-1374, Blackwell Publishing Ltd., England (Jul. 2011).

Nakar et al., (2015) "Prompt immune tolerance induction at inhibitor diagnosis regardless of titre may increase overall success in haemophilia A complicated by inhibitors: experience of two U.S. centres", Haemophilia, 21(3): 365-373, doi:10.1111/hae.12608.

Negrier, C., et al., "Enhanced pharmacokinetic properties of a glycoPEGylated recombinant factor IX: a first human dose trial in patients with hemophilia B," Blood 118(10):2695-2701, The American Society of Hematology, United States (Sep. 2011).

Ngo, J.C.K., et al., "Crystal structure of human factor VIII: implications for the formation of the factor IXa-factor VIIIa complex," Structure 16(4):597-606, Cell Press, United States (2008).

Nilsson, I.M., et al., "Twenty-five years' experience of prophylactic treatment in severe haemophilia A and B," Journal of Internal Medicine 232(1):25-32, Blackwell Scientific Publications, England (1992).

Noble, et al., "IL-12 and IL-4 Activate a CD39- Dependent Intrinsic Peripheral Tolerance Mechanism in CD+ T Cells", European Journal of Immunology, vol. 46, No. 6, 11 Pages, Jun. 2016.

Oganesyan, V., et al., "Structural characterization of a human Fc fragment engineered for extended serum half-life," Molecular Immunology 46(8-9):1750-1755, Pergamon Press, England (2009).

Oldenburg et al., (2006) "Genetic risk factors for inhibitors to factors VIII and IX", Haemophilia, 12(Suppl 6): 15-22, doi:10.1111/j.1365-2516.2006.01361.x.

Pan, J., et al., "Enhanced Efficacy of Recombinant FVIII in Noncovalent Complex with PEGylated Liposome in Hemophilia A Mice," Blood 114(13):2802-2811, The American Society of Hematology, United States (2009).

Pavlova, A., et al., "Impact of polymorphisms of the major histocompatibility complex class II, interleukin-10, tumor necrosis factor-α and cytotoxic T-lymphocyte antigen-4 genes on inhibitor development in severe hemophilia A," Journal of Thrombosis and Haemostasis 7(12):2006-2015, Blackwell Publishing, England (2009).

Persson, E., et al., "Rational design of coagulation factor VIIa variant with substantially increased intrinsic activity," Proceedings of the National Academy of Sciences USA 98(24):13583-13588, The National Academy of Sciences, United States (2001).

Persson, E., et al., "Substitution of valine for leucine 305 in factor VIIa increases the intrinsic enzymatic activity," The Journal of Biological Chemistry 276(31):29195-29199, The American Society for Biochemistry and Molecular Biology, Inc., United States (2001).

Peters, R.T., et al., "Biochemical and Functional Characterization of a Recombinant Monomeric Factor VIII-Fc Fusion Protein," Journal of Thrombosis and Haemostasis 11(1):132-141, Blackwell Publishing, England (Published online: Jan. 27, 2013).

Peters, R.T., et al., "Prolonged Activity of Factor IX as a Monomeric Fc Fusion Protein," Blood 115(10): 2057-2064, The American Society of Hematology, United States (Mar. 2010; Prepub. Online Jan. 2010).

Petrini, P., et al., "Prophylaxis with factor concentrates in preventing hemophilic arthropathy," The American Journal of Pediatric Hematology/Oncology 13(3):280-287, Raven Press, United States, (1991).

Petrovan, R.J. and Ruf, W., "Residue Met156 Contributes to the Labile Enzyme Conformation of Coagulation Factor VIIa," The Journal of Biological Chemistry 276(9):6616-6620, The American Society for Biochemistry and Molecular Biology, Inc., United States (2001).

(56) References Cited

OTHER PUBLICATIONS

Powell, J.S., et al., "Safety and prolonged activity of recombinant factor VIII Fc fusion protein in hemophilia A patients," Blood 119(13):3031-3037, The American Society of Hematology, United States (Mar. 29, 2012).
Qadura, M., et al., "Reduction of the immune response to factor VIII mediated through tolerogenic factor VIII presentation by immature dendritic cells," Journal of Thrombosis and Haemostasis 6(12):2095-2104, Blackwell Publishing Ltd., England (2008).
Risebrough, N., et al., "Cost-utility analysis of Canadian tailored prophylaxis, primary prophylaxis and on-demand therapy in young children with severe haemophilia A," Haemophilia 14(4):743-752, Blackwell Publishing Ltd., England (2008).
Roberts, S.A., et al., "Engineering factor Viii for Hemophilia Gene Therapy," Genetic Syndrome Gene Therapy S1: 1-7, OMICS, India (2011).
Rocino, et al., "Successful Immune Tolerance Treatment with Monoclonal or Recombinant Factor VIII Concentrates in High Responding Inhibitor Patients", Vox Sanguinis, vol. 77, Supplement 1, pp. 65-69, Sep. 2001.
Rodriguez-Merchan, E.C., "Management of Musculoskeletal Complications of Hemophilia," Seminars in Thrombosis and Hemostasis 25(1):87-95, Thieme, United States (2003).
Rojas, et al., "IL-10: A Multifunctional Cytokine in Viral Infections", Review Article, Journal of Immunology Research, 15 Pages, Feb. 20, 2017.
Roopenian, D.C., and Akilesh, S., "FcRn: the Neonatal Fc Receptor Comes of Age," Nature Reviews Immunology 7(9):715-725, Nature Publishing Group, England (2007).
Rosén, S., "Assay of Factor VIII:C with a Chromogenic Substrate," New Frontiers in Hemophilia Research, the XVth World Federation of Hemophilia Congress Stockholm, Sweden, Jun. 27-Jul. 1, 1983, published in Scandinavian Journal of Rheumatology Supplement 33(S40):139-145, Munksgaard, Denmark (1984).
Röstin, J., et al., "B-Domain Deleted Recombinant Coagulation Factor VIII Modified with Monotherapy Polyethylene Glycol," Bioconjugate Chemistry 11(3):387-396, American Chemical Society, United States (2000).
Sakurai, et al., "Acquired Hemophilia A: A Frequently Overlooked Autoimmune Hemorrhagic Disorder", Journal of Immunology Research, vol. 2014, Article ID 320674, 10 Pages, Mar. 24, 2014.
Salas, J., et al., "Enhanced pharmacokinetics of factor VIIA as a monomeric FC Fusion," Journal of Thrombosis and Haemostasis 9(Suppl. 2):268, Blackwell Publishing, England (Jul. 2011).
Scalone et al., (2006) "Quality of life is associated to the orthopaedic status in haemophilic patients with inhibitors", Haemophilia, 12(2): 154-162, doi:10.1111/j.1365-2516.2006.01204.x.
Schmidt, S.R., "Fusion proteins as biopharmaceuticals—Applications and challenges," Current Opinion in Drug Discovery & Development 12(2):284-295, Thomson Reuters, England (2009).
Shen, B.W., et al., "The tertiary structure and domain organization of coagulation factor VIII," Blood 111(3):1240-1247, The American Society of Hematology, United States (2007).
Sichler, K., et al., "Physiological fl Xa activation involves a cooperative conformational rearrangement of the 99-loop," The Journal of Biological Chemistry 278(6):4121-4126, The American Society for Biochemistry and Molecular Biology, Inc., United States (2003).
Simioni, P., et al., "X-linked thrombophilia with a mutant factor IX (factor IX Padua)," The New England Journal of Medicine 361(17): 1671-1675, Massachusetts Medical Society, United States (2009).
Simister, "Placental Transport of Immunoglobulin G", Vaccine, vol. 21, No. 24, pp. 3365-3369, Jul. 28, 2003.
Smith, N.L., et al., "Novel associations of multiple genetic loci with plasma levels of factor VII, factor VIII, and von Willebrand factor: The CHARGE (Cohorts for Heart and Aging Research in Genome Epidemiology) Consortium," Circulation 121(12):1382-1392, American Heart Association Inc., United States (2010).
Soejima, K., et al., "Factor VIIa modified in the 170 loop shows enhanced catalytic activity but does not change the zymogen-like property," The Journal of Biological Chemistry 276(20):17229-17235, The American Society for Biochemistry and Molecular Biology, Inc., United States (2001).
Soejima, K., et al., "The 99 and 170 loop-modifier factor VIIa mutants show enhanced catalytic activity without tissue factor," The Journal of Biological Chemistry 277(50):49027-49035, The American Society for Biochemistry and Molecular Biology, Inc., United States (2002).
Spitzer, S.G., et al., "Replacement of isoleucine-397 threonine in the clotting proteinase factor IXa (Los Angeles and Long Beach variants) affects macromolecular catalysis but not L-tosylarginine methyl ester hydrolysis. Lack of correlation between the ox brain prothrombin time and the mutation site in the variant proteins," The Journal of Biological Chemistry 265(1):219-225, The American Society for Biochemistry and Molecular Biology, Inc., United States (1990).
Srivastava et al., (Jan. 2013) "Guidelines for the management of hemophilia", Haemophilia, 19(1): e1-47, doi:10.1111/j.1365-2516.2012.02909.x.
Stiefel et al., "Immune tolerance induction with high-dose FVIII and pulsed intravenous immunoglobulin", Haemostaseologie, Nov. 2010, 30(Suppl 1): S119-S121 (Article in German - English abstract included).
Streif et al., "Inhibitor treatment by rituximab in congenital haemophilia A- Two case reports", Haemostaseologie, May 2009, 29(2): 151-154 (Article in German unavailable—English abstract included).
Stroobants, A.K., et al., "Differences between one stage clotting and chromogenic factor VIII assay results," Journal of Thrombosis and Haemostasis 9(Suppl 2):381 (Abstract P-TU-230), Blackwell Publishing, England (Jul. 2011).
Strürzebecher, J., "Dramatic enhancement of the catalytic activity of coagulation factor IXa by alcohols," FEBS Letters 412(2):295-300, Federation of European Biochemical Societies, Netherlands (1997).
Supplementary European Search Report received for European Patent Application No. 13735995.6, mailed on Jul. 27, 2015.
Tagariello et al., (2013) "High rate of spontaneous inhibitor clearance during the long term observation study of a single cohort of 524 haemophilia A patients not undergoing immunotolerance", J Hematol Oncol, 6: 63, doi:10.1186/1756-8722-6-63.
Ter Avest et al., "Successful low-dose immune tolerance induction in severe haemophilia A with inhibitors below 40 Bethesda Units", Haemophilia, May 2010, 16(102): 71-79.
Thom et al., "Spontanous disappearance of high titre factor VIII inhibitor 15 years after unsuccessful ITI", Haemostaseologie, May 2009, 29(2): 149-150 (Article in German - English abstract included).
Toole, J.J., et al., "Molecular cloning of a cDNA encoding human antihaemophilic factor," Nature 312(5992):342-347, Nature Publishing Group, England (1984).
Vaccaro, C., et al., "Engineering the Fc region of immunoglobulin G to modulate in vivo antibody levels," Nature Biotechnology 23(10): 1283-1288, Nature America Publishing, United States (2005).
Valentino et al., (2015) "US Guidelines for immune tolerance induction in patients with haemophilia A and inhibitors", Haemophilia, 21(5): 559-567, doi:10.1111/hae.12730.
Van Den Berg, H.M., et al., "Comparing outcomes of different treatment regimens for severe haemophilia," Haemophilia 9(1 Suppl):27-31, Blackwell Science, United States (2003).
Van Den Berg, H.M., et al., "Issues surrounding therapeutic choices for hemophilia patients," Haematologica 89(6):645-650, Ferrata Storti Foundation, Italy (2004).
Van Rooijen, et al., "Liposomes for Specific Depletion of Macrophages from Organs and Tissues", Methods of Molecular Biology, vol. 605, pp. 189-203, 2010.
Van Schooten, et al., "Macrophages Contribute to the Cellular Uptake of Von Willebrand Factor and Factor VIII in Vivo", Blood, vol. 112, No. 5, pp. 1704-1712, Sep. 1, 2008.
Vasanthi, et al., "Role of Tumor Necrosis Factor-Alpha in Rheumatoid Arthritis: a Review", APLAR Journal of Rheumatology, vol. 10, No. 4, pp. 270-274, Dec. 2007.
Vehar, G.A., et al., "Structure of human factor VIII," Nature 312(5992):337-342, Nature Publishing Group. England (1984).
Vysotchin, A., et al., "Domain structure and domain-domain interactions in human coagulation factor IX," The Journal of Biological Chemistry 268(12):8436-8446, The American Society for Biochemistry and Molecular Biology, Inc., United States (1993).

(56) References Cited

OTHER PUBLICATIONS

Wakabayashi, H., et al., "Residues 110-126 in the A1 Domain of Factor VIII Contain a Ca2+ Binding Site Required for Cofactor Activity," The Journal of Biological Chemistry 279(13): 12677-12684, The American Society for Biochemistry and Molecular Biology, Inc., United States (2004).

Weimer, T., et al., "Prolonged in-vivo half-life of factor VIIa by fusion to albumin," Thrombosis and Haemostasis 99(4):659-667, Stuttgart, Schattauer, Germany (2008).

Whelan et al., (2013) "Distinct characteristics of antibody responses against factor VIII in healthy individuals and in different cohorts of hemophilia A patients", Blood, 121(6): 1039-1048, doi:10.1182/blood-2012-07-444877.

White, G.C., 2nd., et al., "A multicenter study of recombinant factor VIII (recombinate TM) in previously treated patients with hemophilia A. The Recombinate previously treated patient study group," Thrombosis and Haemostasis 77(4):660-667, Stuttgart, Schattauer, Germany (1997).

Wood., W.I., et al., "Expression of active human factor VIII from recombinant DNA clones," Nature 312(5992):330-337, Nature Publishing Group, England (1984).

Yoshida, M., et al., Human neonatal Fc receptor mediates transport of IgG into luminal secretions for delivery of antigens to mucosal dendritic cells, Immunity 20(6):769-783, Cell Press, United States (2004).

Zögg, T. and Brandstetter, H., "Structural basis of the cofactor- and substrate-assisted activation of human coagulation factor IXa," Structure 17(12):1669-1678, Cell Press, United States (2009).

Coppola et al., "Optimizing management of immune tolerance induction in patients with severe haemophilia A and inhibitors: towards evidence-based approaches", Br J Haematol., Sep. 2010, 150(5): 515-528, Epublished Jun. 22, 2010.

Huang et al., "EMA Reflection paper on Immune Tolerance Induction for Patients Having Hemophilia A Developed with Inhibitory Antibodies", Jul. 30, 2012.

Pipe, "New therapies for hemophilia", Hematology Am Soc Hematol Educ Program, Treatment of Congenital Bleeding Disorders, Dec. 2, 2016, 2016(1): 650-656.

\* cited by examiner

METHODS OF INDUCING IMMUNE TOLERANCE TO CLOTTING FACTORS

CROSS-REFERENCE TO RELATED APPLICATIONS

This application is a 35 U.S.C. § 371 filing of International Patent Application No. PCT/US2017/064323, filed Dec. 1, 2017, which claims the benefit of U.S. Provisional Patent Application Ser. Nos. 62/429,516, filed Dec. 2, 2016, 62/466,937, filed Mar. 3, 2017, 62/529,866, filed Jul. 7, 2017, 62/558,790, filed Sep. 14, 2017, and 62/582,829, filed Nov. 7, 2017, each of which are incorporated herein by reference in their entirety.

FIELD OF THE DISCLOSURE

The present disclosure relates generally to the field of therapeutics for hemostatic disorders.

BACKGROUND

Hemophilia an X-linked bleeding disorder caused by mutations and/or deletions in genes encoding coagulation proteins, in particular the factor VIII (FVIII) gene, resulting in a deficiency of FVIII activity (hemophilia A), or the factor IX gene, resulting in a deficiency of FIX activity (hemophilia B) (see, e.g., Peyvandi, F. et al. *Haemophilia* 12:82-89 (2006)). The disease is characterized by spontaneous hemorrhage and excessive bleeding after trauma. Treatment of hemophilia is by replacement therapy targeting restoration of FVIII and/or FIX activity to prevent spontaneous bleeding (see, e.g., Mannucci, P. M., et al., *N. Engl. J. Med.* 344:1773-1779 (2001).

Clotting factor replacement therapy is the leading treatment of hemophilia. However, a substantial portion of hemophilia patients, including nearly 30% of patients with severe hemophilia A, develop inhibitors against the clotting factor products, greatly reducing their efficacy in these patients. The immune response is a T-cell-dependent or B-cell-mediated immune response directed against the infused clotting factor, e.g., a FVIII replacement therapy.

While people with severe hemophilia are more likely to develop inhibitors, approximately 5-8% of people with mild or moderate hemophilia A develop inhibitors. Development of clotting factor inhibitors can be deadly because the antibodies can inhibit not only the factor concentrate infused but also any small percentage of factor protein that the body was producing naturally. Therefore, a person with mild or moderate hemophilia who develops an inhibitor now, in effect, has severe hemophilia (<1% circulating factor).

Approximately 2-3% of people with hemophilia B develop inhibitors. While inhibitors in people with hemophilia B are less common than hemophilia A, it can be even more challenging as about half of hemophilia B inhibitor patients will develop an anaphylactic reaction to infused FIX, which can be life-threatening.

Therefore, a need remains for methods of inducing immune tolerance in a human who has already developed an immune response to one or more clotting factors and who has not responded to a previous immune tolerance therapy.

BRIEF SUMMARY

The present disclosure provides a method of inducing immune tolerance in a human with hemophilia, comprising administering to the human an effective amount of a chimeric protein comprising a clotting factor and an Fc region or a composition comprising a clotting factor and an Fc region, wherein the human has developed an inhibitor against the clotting factor and failed to respond to one or more previous immune tolerance therapy against the clotting factor. In some aspects, the method further comprises measuring the level of an inhibitory immune response before the administration and measuring the level of an inhibitory immune response after the administration. In some aspects, the method further comprises comparing the level of the inhibitory immune response before the administration to the level of the inhibitory immune response after the administration.

The present invention further provides a method of inducing immune tolerance in a human with hemophilia, comprising (1) administering to the human an effective amount of a chimeric protein comprising a clotting factor and an Fc region or a composition comprising a clotting factor and an Fc region, wherein the effective amount of the chimeric protein induces immune tolerance in the human; and (2) following induction of immune tolerance, administering to the human a tapering regimen of the chimeric protein. In certain aspects, the induction of immune tolerance occurs when the titer of the inhibitory antibodies in the human is less than about 0.6 BU. In certain aspects, the method further comprises (3) following the tapering regimen, administering to the human a prophylactic dose of the clotting factor. In certain aspects, the human has not been treated with a previous immune tolerance therapy against the clotting factor.

In some aspects, the human has developed an inhibitory immune response to the clotting factor. In some embodiments, the inhibitory immune response comprises production of inhibitory antibodies against the clotting factor. In some embodiments, the titer of the inhibitory antibodies prior to the administration is at least about 0.6 Bethesda Units (BU). In some embodiments, the titer of the inhibitory antibodies after the administration is less than about 0.6 BU.

In some aspects, the immune response comprises a cell-mediated immune response. In some embodiments, the cell-mediated immune response comprises the release of a cytokine. In some embodiments, the administration reduces the level of a cytokine in the human compared to the level in the human after a previous treatment with a polypeptide consisting of a FVIII polypeptide. In some embodiments, the cytokine selected from the group consisting of IL-12, IL-4, IL-17, TNF-α, and any combination thereof.

In certain aspects, an expression of one or more tolerogenic molecules is increased after the administration relative to the expression level of the one or more tolerogenic molecules prior to the administration. In some embodiments, the one or more tolerogenic molecules is selected from IL-10, TGF-β, IL-35, IDO-1, and any combination thereof. In other embodiments, the immune response comprises a clinical symptom selected from the group consisting of: increased bleeding tendency, high clotting factor consumption, lack of response to clotting factor therapy, decreased efficacy of clotting factor therapy, and shortened half-life of the clotting factor.

In some embodiments, the human was previously diagnosed as having developed an inhibitory immune response to the clotting factor at least about 1 month, at least about 2 months, at least about 3 months, at least about 6 months, at least about 12 months, at least about 18 months, at least about 24 months, at least about 30 months, at least about 36 months, at least about 42 months, at least about 48 years, at least about 54 months, at least about 60 months, at least about 6 years, at least about 7 years, at least about 8 years, or at least about 10 years prior to the administration. In some embodiments, the time to tolerance is about 1 to about 24 weeks, about 1 to about 23 weeks, about 1 to about 22 weeks, about 1 to about 21 weeks, about 2 to about 20 weeks, about 2 to about 19 weeks, about 2 to about 18 weeks, about 2 to about 17 weeks, about 3 to about 16 weeks, about 3 to about 15 weeks, about 3 to about 14 weeks, about 3 to about 13 weeks, about 4 to about 12 weeks, about 4 to about 11 weeks, about 4 to about 10 weeks, about 4 to about 9 weeks, about 5 to about 8 weeks, about 5 to about 7 weeks, about 5 to about 6 weeks, about 1 to about 12 weeks, about 1 to about 11 weeks, about 1 to about 10 weeks, about 1 to about 9 weeks, about 1 to about 8 weeks, about 1 to about 7 weeks, about 1 to about 6 weeks, about 1 to about 5 weeks, or about 1 to about 4 weeks.

In some aspects, the clotting factor is factor VIII (FVIII). In some embodiments, the chimeric protein comprises FVIII-Fc. In certain embodiments, the chimeric protein comprises a FVIII portion and a VWF portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other.

In some aspects, the chimeric protein further comprises a half-life extending moiety. In certain embodiments, the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof.

In some embodiments, the effective amount of the chimeric protein comprising FVIII and an Fc region is from about 20 IU/kg to about 300 IU/kg. In some embodiments, the chimeric protein comprising FVIII-Fc is administered at a dosing interval of about one day, about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days.

In certain aspects, the human previously developed a FVIII inhibitory immune response. In some embodiments, the human has a bleeding condition selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intra cranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

EMBODIMENTS

E1. A method of inducing immune tolerance in a human with hemophilia, comprising administering to the human an effective amount of a chimeric protein comprising a clotting factor and an Fc region, wherein the human has developed an inhibitor against the clotting factor and failed to respond to one or more previous immune tolerance therapy against the clotting factor.

E2. The method of E1, further comprising measuring the level of an inhibitory immune response before the administration and measuring the level of an inhibitory immune response after the administration.

E3. The method of E2, further comprising comparing the level of the inhibitory immune response before the administration to the level of the inhibitory immune response after the administration.

E4. The method of any one of E1 to E3, wherein the human has developed an inhibitory immune response to the clotting factor.

E5. The method of E4, wherein the inhibitory immune response comprises production of inhibitory antibodies against the clotting factor.

E6. The method of E5, wherein the titer of the inhibitory antibodies prior to the administration is at least about 0.6 Bethesda Units (BU).

E7. The method of E5 or E6, wherein the titer of the inhibitory antibodies prior to the administration is at least about 1 BU, at least about 2 BU, at least about 3 BU, at least about 4 BU, at least about 5 BU, at least about 6 BU, at least about 7 BU, at least about 10 BU, at least about 20 BU, at least about 30 BU, at least about 40 BU, at least about 50 BU, at least about 100 BU, at least about 150 BU, or at least about 200 BU.

E8. The method of any one of E5 to E7, wherein the titer of the inhibitory antibodies prior to the administration is at least about 5 BU.

E9. The method of any one of E5 to E8, wherein the titer of the inhibitory antibodies after the administration is less than about 0.6 BU.

E10. The method of any one of E5 to E9, wherein the titer of the inhibitory antibodies after the administration is 0 BU.

E11. The method of claim any one of E1 to E10, wherein the immune response comprises a cell-mediated immune response.

E12. The method of E11, wherein the cell-mediated immune response comprises the release of a cytokine.

E13. The method of E12, wherein the administration reduces the level of a cytokine in the human compared to the level in the human after a previous treatment with a polypeptide consisting of a FVIII polypeptide.

E14. The method of E12 or E13, wherein the cytokine selected from the group consisting of IL-12, IL-4, IL-17, TNF-α, and any combination thereof.

E15. The method of any one of E1 to E14, wherein an expression of one or more tolerogenic molecules is increased after the administration relative to the expression level of the one or more tolerogenic molecules prior to the administration.

E16. The method of E15, wherein the one or more tolerogenic molecules is selected from IL-10, TGF-β, IL-35, IDO-1, and any combination thereof.

E17. The method of any one of E1 to E14, wherein the immune response comprises a clinical symptom selected from the group consisting of: increased bleeding tendency, high clotting factor consumption, lack of response to clotting factor therapy, decreased efficacy of clotting factor therapy, and shortened half-life of the clotting factor.

E18. The method of any one of E1 to E17, wherein the human was previously diagnosed as having developed an inhibitory immune response to the clotting factor at least about 3 months, at least about 6 months, at least about 12 months, at least about 18 months, at least about 24 months, at least about 30 months, at least about 36 months, at least about 42 months, at least about 48 years, at least about 54 months, at least about 60 months, at least about 6 years, at least about 7 years, at least about 8 years, or at least about 10 years prior to the administration.

E19. The method of any one of E1 to E18, wherein the human was previously diagnosed as having developed an inhibitory immune response to the clotting factor at least about 5 years prior to the administration.

E20. The method of any one of E1 to E19, wherein the time to tolerance is about 1 to about 24 weeks, about 1 to about 23 weeks, about 1 to about 22 weeks, about 1 to about 21 weeks, about 2 to about 20 weeks, about 2 to about 19 weeks, about 2 to about 18 weeks, about 2 to about 17 weeks, about 3 to about 16 weeks, about 3 to about 15 weeks, about 3 to about 14 weeks, about 3 to about 13 weeks, about 4 to about 12 weeks, about 4 to about 11 weeks, about 4 to about 10 weeks, about 4 to about 9 weeks, about 5 to about 8 weeks, about 5 to about 7 weeks, about 5 to about 6 weeks, about 1 to about 12 weeks, about 1 to about 11 weeks, about 1 to about 10 weeks, about 1 to about 9 weeks, about 1 to about 8 weeks, about 1 to about 7 weeks, about 1 to about 6 weeks, about 1 to about 5 weeks, or about 1 to about 4 weeks.

E21. The method of any one of E1 to E20, wherein the time to tolerance is less than about 24 weeks, less than about 23 weeks, less than about 22 weeks, less than about 21 weeks, less than about 20 weeks, less than about 19 weeks, less than about 18 weeks, less than about 17 weeks, less than about 16 weeks, less than about 15 weeks, less than about 14 weeks, less than about 13 weeks, less than about 12 weeks, less than about 11 weeks, less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, or less than about 1 week.

E22. The method of any one of E1 to E21, wherein the time to tolerance is about 4 to about 12 weeks.

E23. The method of any one of E1 to E22, wherein the time to tolerance is about 4 weeks.

E24. The method of any one of E1 to E23, wherein the human is receiving interferon therapy.

E25. The method of any one of E1 to E24, wherein the human is receiving anti-viral therapy.

E26. The method of any one of E1 to E25, wherein the human has a genetic polymorphism associated with increased TNF-α.

E27. The method of E26, wherein the polymorphism is TNF-308G>A.

E28. The method of any one of E1 to E27, wherein the human has a genetic polymorphism associated with increased IL 10.

E29. The method of E28, wherein the polymorphism is allele 134 of the IL10G microsatellite.

E30. The method of any one of E1 to E29, wherein the human has had less than 150 exposure days (ED) to the clotting factor.

E31. The method of E30, wherein the human has had less than 50 ED.

E32. The method of E31, wherein the human has had less than 20 ED.

E33. The method of any one of E1 to E32, wherein the clotting factor is factor VIII (FVIII).

E34. The method of any one of E1 to E33, wherein the chimeric protein comprises FVIII-Fc.

E35. The method of any one of E1 to E34, wherein the chimeric protein comprises a FVIII portion and a VWF portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other.

E36. The method of any one of E33 to E35, wherein the FVIII polypeptide comprises mature FVIII.

E37. The method of any one of E33 to E35, wherein the FVIII polypeptide comprises a B domain deleted FVIII.

E38. The method of E37, wherein the B domain deleted FVIII comprises a deletion of all or part of the B domain of FVIII.

E39. The method of E37 or E38, wherein the B domain deleted FVIII comprises a deletion of amino acid residues 746 to 1648 of mature FVIII.

E40. The method of any one of E33 to E39, wherein the VWF polypeptide comprises a VWF fragment comprising a D' domain and a D3 domain of VWF.

E41. The method of any one of E1 to E40, wherein the chimeric protein further comprises a half-life extending moiety.

E42. The method of E41, wherein the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof.

E43. The method of E41 or E42, wherein the half-life extending moiety is inserted within the clotting factor.

E44. The method of E41 or E42, wherein the half-life extending moiety is inserted between the clotting factor and the Fc region.

E45. The method of any one of E33 to E44, wherein the effective amount of the chimeric protein comprising FVIII and an Fc region is from about 20 IU/kg to about 300 IU/kg.

E46. The method of E45, wherein the effective amount of the chimeric protein comprising FVIII-Fc is from about 100 IU/kg to about 300 IU/kg, from about 100 IU/kg to about 200 IU/kg, from about 100 IU/kg to about 290 IU/kg, from about 100 IU/kg to about 280 IU/kg, from about 100 IU/kg to about 270 IU/kg, from about 100 IU/kg to about 260 IU/kg, from about 100 IU/kg to about 250 IU/kg, from about 100 IU/kg to about 240 IU/kg, from about 100 IU/kg to about 230 IU/kg, from about 100 IU/kg to about 220 IU/kg, from about 100 IU/kg to about 210 IU/kg, from about 150 IU/kg to about 300 IU/kg, from about 150 IU/kg to about 290 IU/kg, from about 150 IU/kg to about 280 IU/kg, from about 150 IU/kg to about 270 IU/kg, from about 150 IU/kg to about 260 IU/kg, from about 150 IU/kg to about 250 IU/kg, from about 150 IU/kg to about 240 IU/kg, from about 140 IU/kg to about 250 IU/kg, from about 130 IU/kg to about 260 IU/kg, from about 120 IU/kg to about 270 IU/kg, from about 110 IU/kg to about 280 IU/kg, from about 200 IU/kg to about 290 IU/kg, from about 200 IU/kg to about 280 IU/kg, from about 200 IU/kg to about 270 IU/kg, from about 200 IU/kg to about 260 IU/kg, from about 200 IU/kg to about 250 IU/kg, from about 200 IU/kg to about 240 IU/kg, from about 200 IU/kg to about 230 IU/kg, from about 200 IU/kg to about 220 IU/kg, or from about 200 IU/kg to about 210 IU/kg.

E47. The method of E45 or E46, wherein the effective amount of the chimeric protein comprising FVIII-Fc is about 100 IU/kg, about 105 IU/kg, about 110 IU/kg, about 115 IU/kg, about 120 IU/kg, about 125 IU/kg, about 130 IU/kg, about 135 IU/kg, about 140 IU/kg, about 145 IU/kg, about 150 IU/kg, about 155 IU/kg, about 160 IU/kg, about 165 IU/kg, about 170 IU/kg, about 175 IU/kg, about 180 IU/kg, about 185 IU/kg, about 190 IU/kg, about 195 IU/kg, about 200 IU/kg, about 225 IU/kg, about 250 IU/kg, about 275 IU/kg, or about 300 IU/kg.

E48. The method of any one of E33 to E47, wherein the chimeric protein comprising FVIII-Fc is administered at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days.

E49. The method of any one of E33 to E47, wherein the chimeric protein comprising FVIII-Fc is administered at a dosing interval of about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 14 days, about 3 to about 14 days, about 4 to about 14 days, about 5 to about 14 days, about 6 to about 14 days, about 7 to about 14 days, about 8 to about 14 days, about 9 to about 14 days, about 10 to about 14 days, about 11 to about 14 days, about 12 to about 14 days, about 13 to about 14 days, or about 5 to about 10 days.

E50. The method of any one of E33 to E49, wherein the chimeric protein comprising FVIII-Fc is administered at a dosing interval about 3 days to about 5 days.

E51. The method of any one of E1 to E33, wherein the chimeric protein comprises
- a FVIII portion, a VWF portion, a first Fc region, and a second Fc region;
- wherein the FVIII portion comprises a FVIII polypeptide or a fragment thereof;
- wherein the VWF portion comprises a VWF polypeptide or a fragment thereof;
- wherein the FVIII portion is linked to the first Fc region;
- wherein the VWF portion is linked to the second Fc region; and
- wherein the first Fc region and the second Fc region are associated with each other.

E52. The method of any one of E1 to E51, wherein the human previously developed a FVIII inhibitory immune response.

E53. The method of E52, wherein the inhibitory FVIII immune response developed in response to a FVIII product selected from the group consisting of: ADVATE®, RECOMBINATE®, KOGENATE FS®, HELIXATE FS®, XYNTHA/REFACTO AB®, HEMOFIL-M®, MONARC-M®, MONOCLATE-P®, HUMATE-P®, ALPHANATE®, KOATE-DVI®, AFSTYLA®, AND HYATE:C®.

E54. The method of E52, wherein the inhibitory FVIII immune response is developed in response to a recombinant FVIII product.

E55. The method of any one of E1 to E54, wherein the human has a bleeding condition selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intra cranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

E56. The method of E55, wherein the bleeding coagulation disorder is hemophilia A.

E57. The method of any one of E33 to E56, wherein the effective amount of the chimeric protein comprising FVIII and an Fc region is about 50 IU/kg to about 300 IU/kg.

E58. The method of any E57, wherein the effective amount of the chimeric protein comprising FVIII and an Fc region is about 50 IU/kg, about 60 IU/kg, about 70 IU/kg, about 80 IU/kg, about 90 IU/kg, about 100 IU/kg, about 110 IU/kg, about 120 IU/kg, about 130 IU/kg, about 140 IU/kg, about 150 IU/kg, about 160 IU/kg, about 170 IU/kg, about 180 IU/kg, about 190 IU/kg, about 200 IU/kg, about 225 IU/kg, about 250 IU/kg, about 275 IU/kg, or about 300 IU/kg.

E59. The method of E57 or E58, wherein the effective amount of the chimeric protein is about 200 IU/kg and is administered daily.

E60. The method of E57 or E58, wherein the effective amount of the chimeric protein is about 50 IU/kg and is administered about three times a week.

E61. The method of any one of E57 to E60, wherein the effective amount of the chimeric protein is administered in two or more doses throughout a day.

E62. The method of any one of E57 to E61, wherein the chimeric protein is administered until immune tolerance is observed, wherein immune tolerance is observed when the titer of the inhibitory antibodies in the human is less than about 0.6 BU.

E63. The method of E62, wherein following immune tolerance, the human is administered a tapering regimen of the chimeric protein comprising FVIII and an Fc region.

E64. The method of E63, wherein the tapering regimen comprises administering a tapering dose of about 50 IU/kg to about 100 IU/kg of the chimeric protein comprising FVIII and an Fc region.

E65. The method of E63 or E64, wherein the tapering dose is administered once a day or once every other day.

E66. The method of any one of E63 to E65, wherein the tapering dose is administered for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, at least about 20 weeks, at least about 21 weeks, at least about 22 weeks, at least about 23 weeks, at least about 24 weeks, at least about 25 weeks, at least about 26 weeks, at least about 27 weeks, at least about 28 weeks, at least about 29 weeks, at least about 30 weeks, at least about 31 weeks, or at least about 32 weeks.

E67. The method of any one of E63 to E66, wherein the tapering regimen comprises administering a tapering dose of the chimeric protein of about 50 IU/kg or about 100 IU/kg.

E68. The method of any one of E63 to E67, wherein the tapering regimen comprises administering a tapering dose of the chimeric protein of about 50 IU/kg once a day from week 1 to week 6 following immune tolerance.

E69. The method of any one of E63 to E67, wherein the tapering regimen comprises administering a tapering dose of the chimeric protein of about 100 IU/kg once a day from week 1 to week 6 following immune tolerance.

E70. The method of E68 or E69, wherein the tapering regimen further comprises administering a tapering dose of the chimeric protein of about 50 IU/kg or about 100 IU/kg once every other day from week 6 to week 12 following immune tolerance.

E71. The method of E70, wherein the tapering regimen further comprises administering a tapering dose of the chimeric protein of about 50 IU/kg or about 100 IU/kg once every other day from week 12 to week 16.

E72. The method of any one of E66 to E71, further comprising administering a prophylactic dose of the clotting factor following the tapering regimen.

E73. The method of E72, wherein the prophylactic dose comprises from about 50 IU/kg to about 100 IU/kg.

E74. The method of E72 or E73, wherein the prophylactic dose is administered about one time per week, about two times per week, about three times per week, or about one time every three to five days.

E75. A method of inducing immune tolerance in a human with hemophilia, comprising
(1) administering to the human an effective amount of a chimeric protein comprising a clotting factor and an Fc region, wherein the effective amount of the chimeric protein comprising a clotting factor and an Fc region induces immune tolerance in the human; and
(2) following induction of immune tolerance, administering to the human a tapering regimen of the chimeric protein.

E76. The method of E75, wherein induction of immune tolerance occurs when the titer of the inhibitory antibodies in the human is less than about 0.6 BU E77. The method of E75 or E77, further comprising:
(3) following the tapering regimen, administering to the human a prophylactic dose of a clotting factor.

E78. The method of any one of E75 to E77, wherein the human has not been treated with a previous immune tolerance therapy against the clotting factor.

E79. The method of any one of E75 to E78, further comprising measuring the level of an inhibitory immune response before the administration and measuring the level of an inhibitory immune response after the administration.

E80. The method of E79, further comprising comparing the level of the inhibitory immune response before the administration to the level of the inhibitory immune response after the administration.

E81. The method of any one of E75 to E80, wherein the human has developed an inhibitory immune response to the clotting factor.

E82. The method of E81, wherein the inhibitory immune response comprises production of inhibitory antibodies against the clotting factor.

E83. The method of E82, wherein the titer of the inhibitory antibodies prior to the administration is at least about 0.6 Bethesda Units (BU).

E84. The method of E82 or E83, wherein the titer of the inhibitory antibodies prior to the administration is at least about 1 BU, at least about 2 BU, at least about 3 BU, at least about 4 BU, at least about 5 BU, at least about 6 BU, at least about 7 BU, at least about 10 BU, at least about 20 BU, at least about 30 BU, at least about 40 BU, at least about 50 BU, at least about 100 BU, at least about 150 BU, or at least about 200 BU.

E85. The method of any one of E82 to E84, wherein the titer of the inhibitory antibodies prior to the administration is at least about 5 BU.

E86. The method of any one of E82 to E85, wherein the titer of the inhibitory antibodies after the administration is less than about 0.6 BU.

E87. The method of any one of E82 to E86, wherein the titer of the inhibitory antibodies after the administration is 0 BU.

E88. The method of claim any one of E79 to E87, wherein the immune response comprises a cell-mediated immune response.

E89. The method of E88, wherein the cell-mediated immune response comprises the release of a cytokine.

E90. The method of E88, wherein the administration reduces the level of a cytokine in the human compared to the level in the human after a previous treatment with a polypeptide consisting of a FVIII polypeptide.

E91. The method of any one of E75 to E90, wherein an expression of one or more tolerogenic molecules is increased after the administration relative to the expression level of the one or more tolerogenic molecules prior to the administration.

E92. The method of any one of E75 to E91, wherein the human was previously diagnosed as having developed an inhibitory immune response to the clotting factor at least about 3 months, at least about 6 months, at least about 12 months, at least about 18 months, at least about 24 months, at least about 30 months, at least about 36 months, at least about 42 months, at least about 48 years, at least about 54 months, at least about 60 months, at least about 6 years, at least about 7 years, at least about 8 years, or at least about 10 years prior to the administration.

E93. The method of any one of E75 to E92, wherein the human was previously diagnosed as having developed an inhibitory immune response to the clotting factor at least about 5 years prior to the administration.

E94. The method of any one of E75 to E93, wherein the time to tolerance is about 1 to about 24 weeks, about 1 to about 23 weeks, about 1 to about 22 weeks, about 1 to about 21 weeks, about 2 to about 20 weeks, about 2 to about 19 weeks, about 2 to about 18 weeks, about 2 to about 17 weeks, about 3 to about 16 weeks, about 3 to about 15 weeks, about 3 to about 14 weeks, about 3 to about 13 weeks, about 4 to about 12 weeks, about 4 to about 11 weeks, about 4 to about 10 weeks, about 4 to about 9 weeks, about 5 to about 8 weeks, about 5 to about 7 weeks, about 5 to about 6 weeks, about 1 to about 12 weeks, about 1 to about 11 weeks, about 1 to about 10 weeks, about 1 to about 9 weeks, about 1 to about 8 weeks, about 1 to about 7 weeks, about 1 to about 6 weeks, about 1 to about 5 weeks, or about 1 to about 4 weeks.

E95. The method of any one of E75 to E94, wherein the time to tolerance is less than about 24 weeks, less than about 23 weeks, less than about 22 weeks, less than about 21 weeks, less than about 20 weeks, less than about 19 weeks, less than about 18 weeks, less than about 17 weeks, less than about 16 weeks, less than about 15 weeks, less than about 14 weeks, less than about 13 weeks, less than about 12 weeks, less than about 11 weeks, less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, or less than about 1 week.

E96. The method of any one of E75 to E95, wherein the time to tolerance is about 4 to about 12 weeks.

E97. The method of any one of E75 to E96, wherein the time to tolerance is about 4 weeks.

E98. The method of any one of E75 to E97, wherein the human is receiving interferon therapy.

E99. The method of any one of E75 to E98, wherein the human is receiving anti-viral therapy.

E100. The method of any one of E75 to E91, wherein the human has a genetic polymorphism associated with increased TNF-α.

E101. The method of E100, wherein the polymorphism is TNF-308G>A.

E102. The method of any one of E75 to E101, wherein the human has a genetic polymorphism associated with increased IL 10.

E103. The method of E102, wherein the polymorphism is allele 134 of the IL10G microsatellite.

E104. The method of any one of E75 to E103, wherein the human has had less than 150 exposure days (ED) to the clotting factor.

E105. The method of E104, wherein the human has had less than 50 ED.

E106. The method of E105, wherein the human has had less than 20 ED.

E107. The method of any one of E75 to E106, wherein the clotting factor is factor VIII (FVIII).

E108. The method of any one of E75 to E107, wherein the chimeric protein comprises FVIII-Fc.

E109. The method of any one of E75 to E108, wherein the chimeric protein comprises a FVIII portion and a VWF portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other.

E110. The method of any one of E75 to E109, wherein the FVIII polypeptide comprises mature FVIII.

E111. The method of any one of E75 to E109, wherein the FVIII polypeptide comprises a B domain deleted FVIII.

E112. The method of E110, wherein the B domain deleted FVIII comprises a deletion of all or part of the B domain of FVIII.

E113. The method of E110 or E111, wherein the B domain deleted FVIII comprises a deletion of amino acid residues 746 to 1648 of mature FVIII.

E114. The method of any one of E109 to E113, wherein the VWF polypeptide comprises a VWF fragment comprising a D' domain and a D3 domain of VWF.

E115. The method of any one of E75 to E114 wherein the chimeric protein further comprises a half-life extending moiety.

E116. The method of E115, wherein the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof.

E116. The method of E115 or E116, wherein the half-life extending moiety is inserted within the clotting factor.

E117. The method of E115 or E116, wherein the half-life extending moiety is inserted between the clotting factor and the Fc region.

E118. The method of any one of E75 to E118, wherein the effective amount of the chimeric protein comprising FVIII and an Fc region is from about 50 IU/kg to about 300 IU/kg.

E120. The method of E119, wherein the effective amount of the chimeric protein comprising FVIII-Fc is from about 100 IU/kg to about 300 IU/kg, from about 100 IU/kg to about 200 IU/kg, from about 100 IU/kg to about 290 IU/kg, from about 100 IU/kg to about 280 IU/kg, from about 100 IU/kg to about 270 IU/kg, from about 100 IU/kg to about 260 IU/kg, from about 100 IU/kg to about 250 IU/kg, from about 100 IU/kg to about 240 IU/kg, from about 100 IU/kg to about 230 IU/kg, from about 100 IU/kg to about 220 IU/kg, from about 100 IU/kg to about 210 IU/kg, from about 150 IU/kg to about 300 IU/kg, from about 150 IU/kg to about 290 IU/kg, from about 150 IU/kg to about 280 IU/kg, from about 150 IU/kg to about 270 IU/kg, from about 150 IU/kg to about 260 IU/kg, from about 150 IU/kg to about 250 IU/kg, from about 150 IU/kg to about 240 IU/kg, from about 140 IU/kg to about 250 IU/kg, from about 130 IU/kg to about 260 IU/kg, from about 120 IU/kg to about 270 IU/kg, from about 110 IU/kg to about 280 IU/kg, from about 200 IU/kg to about 290 IU/kg, from about 200 IU/kg to about 280 IU/kg, from about 200 IU/kg to about 270 IU/kg, from about 200 IU/kg to about 260 IU/kg, from about 200 IU/kg to about 250 IU/kg, from about 200 IU/kg to about 240 IU/kg, from about 200 IU/kg to about 230 IU/kg, from about 200 IU/kg to about 220 IU/kg, or from about 200 IU/kg to about 210 IU/kg.

E121. The method of E119 or E120, wherein the effective amount of the chimeric protein comprising FVIII-Fc is about 50 IU/kg, about 60 IU/kg, about 70 IU/kg, about 80 IU/kg, about 90 IU/kg, about 100 IU/kg, about 110 IU/kg, about 120 IU/kg, about 130 IU/kg, about 140 IU/kg, about 150 IU/kg, about 160 IU/kg, about 170 IU/kg, about 180 IU/kg, about 190 IU/kg, about 200 IU/kg, about 225 IU/kg, about 250 IU/kg, about 275 IU/kg, or about 300 IU/kg.

E122. The method of any one of E75 to E121, wherein the effective amount of the chimeric protein is about 200 IU/kg and is administered daily.

E123. The method of any one of E75 to E122, wherein the chimeric protein comprising FVIII-Fc is administered at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days.

E124. The method of any one of E75 to E121, wherein the chimeric protein comprising FVIII-Fc is administered at a dosing interval of about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 14 days, about 3 to about 14 days, about 4 to about 14 days, about 5 to about 14 days, about 6 to about 14 days, about 7 to about 14 days, about 8 to about 14 days, about 9 to about 14 days, about 10 to about 14 days, about 11 to about 14 days, about 12 to about 14 days, about 13 to about 14 days, or about 5 to about 10 days.

E125. The method of any one of E75 to E122, wherein the chimeric protein comprising FVIII-Fc is administered at a dosing interval about 3 days to about 5 days.

E126. The method of any one of E75 to E125, wherein the chimeric protein comprises a FVIII portion, a VWF portion, a first Fc region, and a second Fc region;
  wherein the FVIII portion comprises a FVIII polypeptide or a fragment thereof;
  wherein the VWF portion comprises a VWF polypeptide or a fragment thereof;
  wherein the FVIII portion is linked to the first Fc region;
  wherein the VWF portion is linked to the second Fc region; and
  wherein the first Fc region and the second Fc region are associated with each other.

E127. The method of any one of E75 to E126, wherein the human previously developed a FVIII inhibitory immune response.

E128. The method of E127, wherein the inhibitory FVIII immune response developed in response to a FVIII product selected from the group consisting of: ADVATE®, RECOMBINATE®, KOGENATE FS®, HELIXATE FS®, XYNTHA/REFACTO AB®, HEMOFIL-M®, MONARC-M®, MONOCLATE-P®, HUMATE-P®, ALPHANATE®, KOATE-DVI®, AFSTYLA®, AND HYATE:C®.

E129. The method of E128, wherein the inhibitory FVIII immune response is developed in response to a recombinant FVIII product.

E130. The method of any one of E75 to E129, wherein the human has a bleeding condition selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intra cranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

E131. The method of E130, wherein the bleeding coagulation disorder is hemophilia A.

E132. The method of any one of E75 to E131, wherein the effective amount of the chimeric protein is administered in two or more doses throughout a day.

E133. The method of any one of E75 to E132, wherein the tapering regimen comprises administering a tapering dose of about 50 IU/kg to about 100 IU/kg of the chimeric protein.

E134. The method of any one of E75 to E133, wherein the tapering dose is administered once a day, once every other day, or three times every week.

E135. The method of any one of E75 to E134, wherein the tapering dose is administered for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, at least about 20 weeks, at least about 21 weeks, at least about 22 weeks, at least about 23 weeks, at least about 24 weeks, at least about 25 weeks, at least about 26 weeks, at least about 27 weeks, at least about 28 weeks, at least about 29 weeks, at least about 30 weeks, at least about 31 weeks, or at least about 32 weeks.

E136. The method of any one of E74 to E135, wherein the tapering regimen comprises administering a tapering dose of the chimeric protein of about 50 IU/kg or about 100 IU/kg.

E137. The method of any one of E75 to E136, wherein the tapering regimen comprises administering a tapering dose of the chimeric protein of about 50 IU/kg once a day from week 1 to week 6 following immune tolerance.

E138. The method of any one of E75 to E136, wherein the tapering regimen comprises administering a tapering dose of the chimeric protein of about 100 IU/kg once a day from week 1 to week 6 following immune tolerance.

E139. The method of E137 or E138, wherein the tapering regimen further comprises administering a tapering dose of the chimeric protein of about 50 IU/kg or about 100 IU/kg once every other day from week 6 to week 12 following immune tolerance.

E140. The method of E139, wherein the tapering regimen further comprises administering a tapering dose of the chimeric protein of about 50 IU/kg or about 100 IU/kg once every other day from week 12 to week 16.

E141. The method of any one of E77 to E140, wherein the prophylactic dose comprises about 50 IU/kg to about 100 IU/kg.

E142. The method of any one of E77 to E141, wherein the prophylactic dose is administered about one time per week, about two times per week, about three times per week, or about three times per week.

E143. The method of any one of E79 to E91 and 94 to E142, wherein the chimeric protein comprising a clotting factor and an Fc region is administered to the human less than about 1 day, less than about 2 days, less than about 3 days, less than about 4 days, less than about 5 days, less than about 6 days, less than about 7 days, less than about 2 weeks, less than about 3 weeks, less than about 4 weeks, less than about 2 months, less than about 3 months, less than about 4 months, less than about 5 months, less than about 6 months, or less than about 1 year after measuring the level of an inhibitory immune response in the human.

E144. The method of any one of E79 to E91 and 94 to E143, wherein the chimeric protein comprising a clotting factor and an Fc region is administered to the human less than about 1 day after measuring the level of an inhibitory immune response in the human.

E145. The method of any one of E79 to E91 and 94 to E144, wherein the chimeric protein comprising a clotting factor and an Fc region is administered to the human less than about 12 hours after measuring the level of an inhibitory immune response in the human.

E146. The method of any one of E1 to E145, wherein the administration of the chimeric protein results in a lower time to tolerance in the human as compared to the time to tolerance in a human following treatment with a clotting factor alone.

BRIEF DESCRIPTION OF THE FIGURES

FIG. 3A shows signaling, as measured by Syk phosphorylation, in THP-1 monocytic cell line ("THP-1"), monocytes, peripheral blood monocyte-derived macrophages ("macrophage"), and peripheral blood monocyte-derived dendritic cells treated with HRP-IC, IgG1, FFVIII or FFVIIIFc for 15 minutes. FIG. 3B shows relative Syk phosphorylation in macrophages treated with rFVIIIFc ("WT"), mutant rFVIIIFc that is unable to bind to neonatal Fc receptor ("FcRn mutant"), or with mutant rFVIIIFc that is unable to bind to FcγR ("FcgR mutant"). FIG. 3C shows the relative production of the proinflammatory cytokines interleukin 1b (IL-1b), IL-6, IL-8, IL-10, and tumor necrosis factor alpha (TNFa) in macrophages twenty-four hours following treatment with HRP-IC, IgG1, FFVIII or FFVIIIFc.

FIGS. 5A-5B are Venn diagrams, illustrating the distribution of genes that were significantly downregulated (FIG. 5A) and the distribution of genes that were significantly upregulated (FIG. 5B) in monocyte-derived macrophages treated with IgG1, rFVIII, or rFVIIIFc for six hours (n=3). FIGS. 5C-5G are graphs showing the relative expressions of various NRF2 and lipid metabolism pathway genes, such as heme oxygenase 1 (Hmox1; FIG. 5C), peroxisome proliferator-activated receptor gamma (PPARγ; FIG. 5D), lipoprotein lipase (LPL; FIG. 5E), early growth response 2 (EGR2; FIG. 5F), and solute carrier organic anion transporter family member 4A1 (SLCO4A1; FIG. 5G); CD206 at 6 hours (FIG. 5I) and 12 hours (FIG. 5J) post treatment; and arginase 1 (ARG1; FIG. 5L) as measured by quantitative PCR, following treatment with rFVIII or FFVIIIFc. Asterisks (*) indicate degree of significance (n=8; *P≤0.05, P≤0.01, *P≤0.005; FIGS. 5C-5G). FIGS. 5K and 5M are graphs showing the number of cells collected by flow cytometry expressing CD206. In addition, rFVIIIFc-educated macrophages were found to exhibit a characteristic M2-like phenotype (FIGS. 5I-5M). In particular, macrophages treated with rFVIIIFc had higher relative CD206 (also known as mannose receptor C-type 1; MRC1) expression than cells treated with rFVIII after 6 hours (FIG. 5I) and after 24 hours (FIG. 5J), and macrophages treated with IFVIIIFc had higher relative ARG1 expression than cells treated with rFVIII after 24 hours (FIG. 5M).

DETAILED DESCRIPTION

Figure 1:
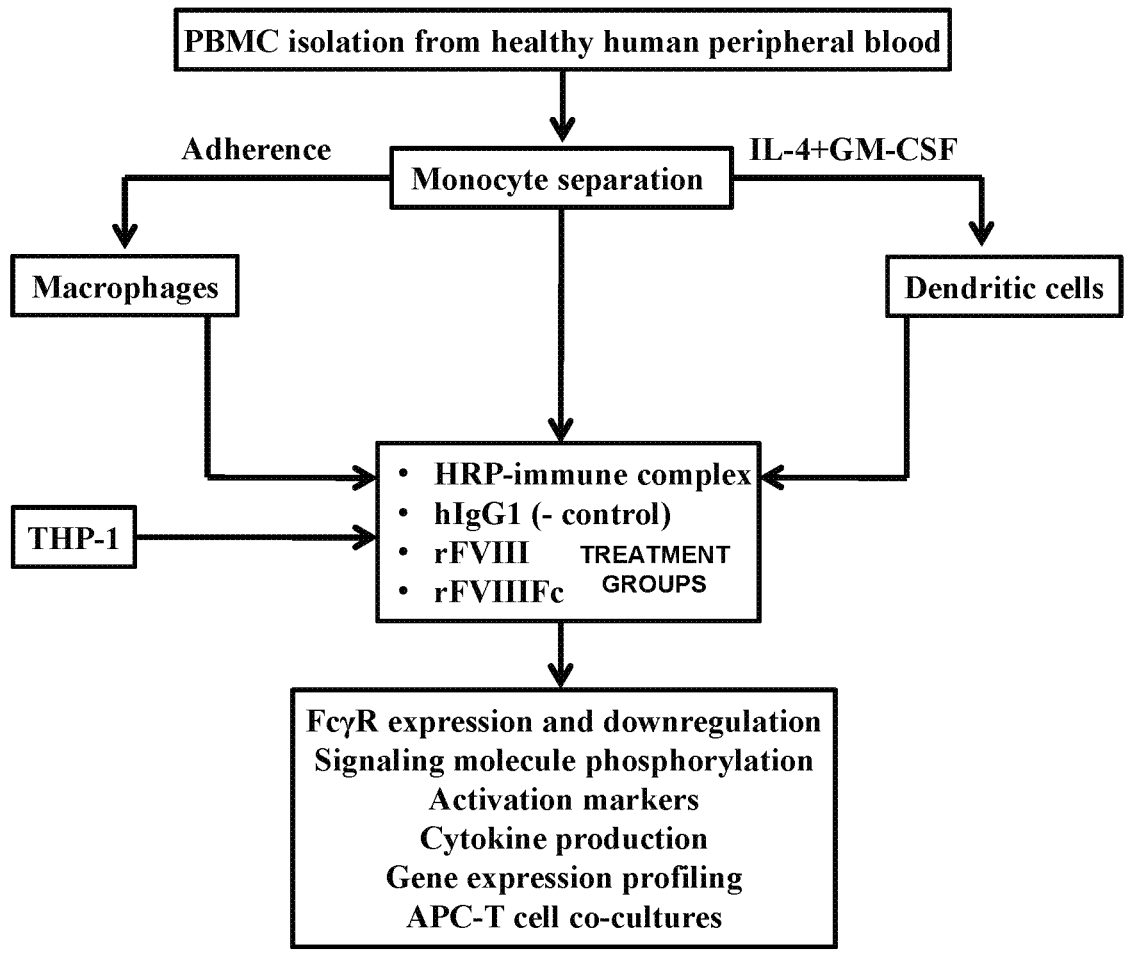
FIG. 1 is a flow diagram, outlining the methods used to investigate the effects of rFVIIIFc on FcγR binding, internalization, signaling and cytokine production, and gene expression changes, as well as subsequent interactions and effects on T cells in vitro.

The present disclosure provides methods of inducing immune tolerance in a human with hemophilia, comprising administering to the human an effective amount of a chimeric protein comprising a clotting factor and an Fc region or a composition comprising a clotting factor and an Fc region, wherein the human has developed an inhibitor against the clotting factor and has failed to respond to one or more previous immune tolerance therapy against the clotting factor. In some embodiments, the clotting factor is selected from the group consisting of factor VII (FVII), factor VIIa (FVIIa), FVIII, FIX, factor X (FX), von Willebrand factor (VWF), and any combination thereof.

I. Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

"Administering," as used herein, means to give a pharmaceutically acceptable composition, e.g., comprising a chimeric protein, disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric protein and hybrid proteins can be administered as part of a pharmaceutical composition comprising at least one excipient. In some embodiments, the clotting factor and/or Fc, e.g., the chimeric protein, are administered to a human through a gene therapy, e.g., wherein one or more polynucleotides encoding the clotting factor and/or Fc, e.g., the chimeric protein, are administered to the human, and the clotting factor and/or Fc, e.g., the chimeric protein, is expressed in the human.

"Treat," "treatment," or "treating," as used herein refers to, e.g., the reduction in severity of a disease or condition; the reduction in the duration of a condition course; the amelioration or elimination of one or more symptoms associated with a disease or condition; the provision of beneficial effects to a subject with a disease or condition, without necessarily curing the disease or condition. In some embodiments, the term "treat" or "treating" means reducing or eliminating an inhibitory immune response to a clotting factor, e.g., FVIII.

The term "induce immune tolerance," as used herein, means to elicit in a subject a condition by which the subject does not have an immune response when administered a particular stimulus, e.g., administration of a clotting factor (e.g., FVIII). This condition, immune tolerance, can be temporary, such that the subject is tolerant to the stimulus for a definite period of time, or prolonged, such that the subject is tolerant to the stimulus indefinitely. In certain embodiments, the subject remains tolerant to the stimulus so long as the stimulus is administered to the subject. For example, in some embodiments, the subject remains tolerant to the clotting factor so long as the chimeric protein comprising the clotting factor and an Fc region is administered to the subject at a given dosing interval. In other embodiments, the subject remains tolerant to the clotting factor even after administration of the chimeric protein comprising the clotting factor and an Fc region is terminated.

In some embodiments, the immune response is an "inhibitory" immune response. An inhibitory immune response is an immune response that blocks or diminishes the effects of the stimulus, e.g., administration of a clotting factor (e.g., FVIII). In certain embodiments, the inhibitory immune response comprises the production of inhibitory antibodies against the stimulus, e.g., inhibitory anti-FVIII antibodies. The term "inhibitory antibody" or "inhibitory antibodies," as used herein, refers to antibodies that block or diminish the function of the antigen recognized by the antibody. For example, an inhibitory antibody against FVIII blocks or diminishes the activity of FVIII. In some embodiments, the inhibitory antibody binds the antigen, e.g., the FVIII, and accelerates the clearance of the antigen from the serum of the human. When the antibody accelerates the clearance of the antigen, the antibody reduces the half-life of the antigen.

Inhibitory immune responses can be determined using laboratory tests such as the Bethesda test or the Nijmegan modification of the Bethesda test. A level of at least 0.6 Bethesda Units (BU) can indicate the presence of an inhibitory immune response. A level of at least 5 BU can indicate the presence of a high titer inhibitor. Measurements of the in vivo recovery and half-life of bolus clotting factor infusion can also be used. In certain embodiments, immune tolerance is observed when the titer of the inhibitory antibodies in the human is less than about 5 BU, less than about 4 BU, less than about 3 BU, less than about 2 BU, less than about 1 BU, less than about 0.9 BU, less than about 0.8 BU, less than about 0.7 BU, less than about 0.6 BU, less than about 0.5 BU, less than about 0.4 BU, less than about 0.3 BU, less than about 0.2 BU, less than about 0.1 BU, or about 0 BU. In one particular embodiment, immune tolerance is observed when the titer of the inhibitory antibodies in the human is less than about 0.6 BU.

In other embodiments, the immune response comprises a cell-mediated immune response. In some embodiments, the cell-mediated immune response comprises the release of a cytokine. In certain embodiments, the cytokines released as part of a cell-mediated immune response can be selected from the group consisting of IL-12, IL-4, IL-17, TNF-α, and any combination thereof.

In other embodiments, the immune response comprises a clinical symptom selected from the group consisting of: increased bleeding tendency, high clotting factor consumption, lack of response to clotting factor therapy, decreased efficacy of clotting factor therapy, shortened half-life of the clotting factor, and any combination thereof.

In other embodiments, immune tolerance is measured by an increase in the half-life of the clotting factor following administration to the human. In some embodiments, immune tolerance is induced once the half-life of the clotting factor is increased by at least about 10%, at least about 15%, at least about 20%, at least about 25%, at least about 30%, at least about 35%, at least about 40%, at least about 45%, at least about 50%, at least about 75%, at least about 100%, at least about 150%, at least about 200%, at least about 300%, at least about 400%, at least about 500%, or at least about 1000% as compared to the half-life of the clotting factor administered to the human before immune tolerance induction. In certain embodiments, the half-life of the clotting factor is at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, or at least about 15 hours following immune tolerance induction.

The term "comparable" as used herein means a compared rate or level resulted from using, e.g., the chimeric protein is equal to, substantially equal to, or similar to the reference rate or level. The term "similar" as used herein means a compared rate or level has a difference of no more than 10% or no more than 15% from the reference rate or level (e.g., FXa generation rate by a chimeric protein consisting essentially of or consisting of two Fc portions and processed FVIII, wherein the processed FVIII is fused to one Fc of the two Fc portions). The term "substantially equal" means a compared rate or level has a difference of no more than 0.01%, 0.5% or 1% from the reference rate or level.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., Von Willebrand disease, factor XI deficiency (PTA deficiency), factor XII deficiency, deficiencies or structural abnormalities in fibrinogen, prothrombin, factor V, factor VII, factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

"Area under the plasma concentration versus time curve (AUC)," as used herein, is the same as the term of art in pharmacology, and is based upon the rate and extent of absorption of FVIII following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC can be carried out in a single subject, or in a population of subjects for which the average is calculated.

The term "procoagulant activity" is meant the ability of the coagulation factor, e.g., a FVIII, of the invention to participate in the clotting cascade in blood, substituting for the native coagulation factor, e.g., native FVIII. Several assays are available for measuring FVIII activity, including the one stage clotting assay (activated partial thromboplastin time; aPTT), thrombin generation time (TGA) and rotational thromboelastometry (ROTEM®).

References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., *J. Exp. Med.* 180:2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

"Hybrid" polypeptides and proteins, as used herein, means a combination of a chimeric protein with a second polypeptide. The chimeric protein and the second polypeptide in a hybrid can be associated with each other via protein-protein interactions, such as charge-charge or hydrophobic interactions. The chimeric protein and the second polypeptide in a hybrid can be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide can be a second copy of the same chimeric protein or it can be a non-identical chimeric protein.

As used herein, an "amino acid corresponding to," "site corresponding to," or "equivalent amino acid" in a protein sequence is identified by alignment to maximize the identity or similarity between a first protein sequence, e.g., a FVIII sequence, and a second protein sequence, e.g., a second FVIII sequence. The number used to identify an equivalent amino acid in a second protein sequence is based on the number used to identify the corresponding amino acid in the first protein sequence.

As used herein, the term "insertion site" refers to an amino acid residue number in a polypeptide (typically a mature polypeptide; e.g., a mature FVIII polypeptide), or fragment, variant, or derivative thereof, which is immediately upstream of the position at which a heterologous moiety can be inserted. An "insertion site" is specified as a number, the number being the number of the amino acid specified protein sequence to which the insertion site corresponds, which is immediately N-terminal to the position of the insertion. For example, the phrase "the FVIII comprises heterologous moiety at an insertion site which corresponds to amino acid 745 of" a given sequence indicates that the heterologous moiety is located between two amino acids corresponding to amino acid 745 and amino acid 746 of the sequence. However, one of skill in the art would readily be able to identify a corresponding position in any variant of the indicated protein, and the present disclosure is not limited to insertions made solely in the variants specifically disclosed herein. Rather, the insertions disclosed herein can be made in any related variants or fragments thereof having activity at a position corresponding to a position of the variants disclosed herein.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which a heterologous moiety (e.g., a half-life extending moiety) is inserted between two adjacent amino acids.

The terms "inserted," "is inserted," "inserted into," or grammatically related terms, as used herein refers to the position of a heterologous moiety (e.g., a half-life extending moiety) in a fusion polypeptide relative to the analogous position in specified protein (e.g., a FVIII protein). Those of skill in the field will understand how to identify corresponding insertion positions with respect to other polypeptide sequences, e.g., other FVIII variants. As used herein the terms refer to the characteristics of the recombinant polypeptide disclosed herein, and do not indicate, imply or infer any methods or process by which the fusion polypeptide was made. For example, in reference to a fusion polypeptide provided herein, the phrase "a heterologous moiety is inserted immediately downstream of residue 745 of the FVIII polypeptide" means that the fusion polypeptide comprises a heterologous moiety immediately downstream of an amino acid which corresponds to amino acid 745 in a particular FVIII variant, e.g., bounded by amino acids corresponding to amino acids 745 and 746 of the FVIII variant.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a FVIII domain of the invention with an Ig Fc domain. A fusion protein is created, for example, by chemical synthesis, or by creating and translating a polynucleotide in which the peptide regions are encoded in the desired relationship. A fusion protein can further comprise a second amino acid sequence associated with the first amino acid sequence by a covalent, non-peptide bond or a non-covalent bond.

The terms "heterologous" and "heterologous moiety" mean that a polynucleotide, polypeptide, or other moiety is derived from a distinct entity from that of the entity to which it is being compared. For instance, a heterologous polypeptide can be synthetic, or derived from a different species, different cell type of an individual, or the same or different type of cell of distinct individuals. In one aspect, a heterologous moiety is a polypeptide fused to another polypeptide to produce a fusion polypeptide or protein. In another aspect, a heterologous moiety is a non-polypeptide such as PEG conjugated to a polypeptide or protein.

The terms "linked" and "fused" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence is linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, factor XIa or factor Xa. Other enzymatic cleavage sites are known in the art.

As used herein, the term "processing site" or "intracellular processing site" refers to a type of enzymatic cleavage site in a polypeptide which is a target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., PCSK1 (also known as PC1/PC3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

A "processable linker" as used herein refers to a linker comprising at least one intracellular processing site, which is described elsewhere herein.

"Baseline," as used herein, is the lowest measured plasma level of a given analyte, e.g., a clotting factor (e.g., FVIII) or an antibody (e.g., an anti-FVIII antibody), in a subject prior to administering a dose. The plasma levels can be measured at two time points prior to dosing: at a screening visit and immediately prior to dosing.

"Equivalent dose," as used herein, means the same dose of clotting factor activity, e.g., FVIII activity, as expressed in International Units, which is independent of molecular weight of the polypeptide in question. For example, one International Unit (IU) of FVIII activity corresponds approximately to the quantity of FVIII in one milliliter of normal human plasma. Several assays are available for measuring clotting factor activity, including the European Pharmacopoeia chromogenic substrate assay and a one stage clotting assay.

"Dosing interval," as used herein, means the dose of time that elapses between multiple doses being administered to a subject. The comparison of dosing interval can be carried out in a single subject or in a population of subjects and then the average obtained in the population can be calculated.

"Subject," as used herein means a human individual. Subject can be a patient who is currently suffering from a bleeding disorder or is expected to be in need of such a treatment. In some embodiments, the subject has never been previously treated with the clotting factor (i.e., the subject is a previously untreated subject or previously untreated patient). In some embodiments, the subject is a fetus and the methods comprise administering the composition or the chimeric protein to the mother of the fetus and the administration to the subject occurs from the mother across the placenta. In some embodiments, the subject is a child or an adult. In some embodiments, the subject is a child less than one-year-old, less than two-year-old, less than three-year-old, less than four-year-old, less than five-year-old, less than six-year-old, less than seven-year-old, less than eight-year-old, less than nine-year-old, less than ten-year-old, less than eleven-year-old, or less than twelve-year-old. In some embodiments, the child is less than one-year old. In some embodiments, the child or adult subject develops a bleeding disorder, wherein the onset of the symptoms of the bleeding disorder is after the one-year-old age. In some embodiments, the administration of the composition or the chimeric protein to the subject is sufficient to prevent, inhibit, or reduce development of an immune response selected from a humoral immune response, a cell-mediated immune response, or both a humoral immune response and a cell-mediated immune response against the clotting factor. In some embodiments, the subject is a human, and the subject has previously developed an immune response to a clotting factor. In some embodiments, the human previously failed to respond to an immune tolerance therapy. In some embodiments, the previous immune tolerance therapy comprises administration of a high dose of a clotting factor. In other embodiments, the previous immune tolerance therapy comprises administration of one or more immunosuppressant. In one embodiment, the previous immune tolerance therapy was a Malmo Regimen. In another embodiment, the previous immune tolerance therapy was a Bonn Protocol.

A "therapeutic dose," "dose," "effective dose," or "dosing amount" as used (interchangeably) herein, means a dose that achieves a therapeutic goal, as described herein. In some embodiments, a "therapeutic dose" means a dose that induces an immune tolerance in a subject. In certain embodiments, a "therapeutic dose" means a dose that induces an immune tolerance in a subject within a specified time to tolerance period, e.g., within 12 weeks of administration of the first dose.

Also included in the present invention are fragments or variants of polypeptides, and any combination thereof. The term "fragment" or "variant" when referring to polypeptides used in the methods of the present disclosure include any polypeptides which retain at least some of the properties (e.g., FcRn binding affinity for an FcRn binding domain or Fc variant, or coagulation activity for a FVIII) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules used in the methods of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity may be curated either automatically or manually.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268:2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-la. They used random mutagenesis to generate over 3,500 individual IL-la mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, FVIII is modified, e.g., pegylated, at any convenient location. In some embodiments, FVIII is pegylated at a surface exposed amino acid of FVIII, e.g., a surface exposed cysteine, which can be an engineered cysteine. Id. In some embodiments, modified FVIII, e.g., pegylated FVIII, is a chimeric or fusion FVIII.

The term "downstream" refers to a nucleotide sequence that is located 3' to a reference nucleotide sequence. "Downstream" can also refer to a peptide sequence that is located C-terminal to a reference peptide sequence.

The term "upstream" refers to a nucleotide sequence that is located 5' to a reference nucleotide sequence. "Upstream" can also refer to a peptide sequence that is located N-terminal to a reference peptide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide, which encodes a gene product, e.g., a polypeptide, can include a promoter and/or other transcription or translation control elements operably associated with one or more coding regions. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, micro-injection, transduction, cell fusion, DEAE dextran, calcium phosphate precipitation, lipofection (lysosome fusion), use of a gene gun, or a DNA vector transporter.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

As used herein, the term "host cell" refers to a cell or a population of cells harboring or capable of harboring a recombinant nucleic acid. Host cells can be a prokaryotic cells (e.g., *E. coli*), or alternatively, the host cells can be eukaryotic, for example, fungal cells (e.g., yeast cells such as *Saccharomyces cerevisiae, Pichia pastoris,* or *Schizosaccharomyces pombe*), and various animal cells, such as insect cells (e.g., Sf-9) or mammalian cells (e.g., HEK293F, CHO, COS-7, NIH-3T3).

"Volume of distribution at steady state (Vss)," as used herein, has the same meaning as the term used in pharmacology, which is the apparent space (volume) into which a drug distributes. Vss=the amount of drug in the body divided by the plasma concentration at steady state.

II. Methods of the Invention

The present disclosure is based on the discovery that a clotting factor fused to an Fc region can be used to induce immune tolerance in a human with hemophilia, wherein the human has developed an inhibitor against a clotting factor and has failed one or more previous immune tolerance therapies. Though it was previously believed that treatment with a FVIII-Fc chimeric protein could prevent an immune response to the FVIII treatment, it was surprisingly discovered in the present disclosure that treatment with a clotting factor-Fc chimeric protein can reduce a previously developed immune response in a human that had not responded to previous immune tolerance therapies. Thus, the present disclosure provides methods for inducing immune tolerance in a human, comprising administering to the human an effective amount of a composition comprising a clotting factor and an Fc or a chimeric protein comprising a clotting factor and an Fc region or a polynucleotide encoding the same.

Another aspect of the present disclosure is directed to a method of inducing immune tolerance in a human with hemophilia, comprising (1) administering to the human an effective amount of a composition comprising a clotting factor and an Fc or a chimeric protein comprising a clotting factor and an Fc region, wherein the effective amount of the composition or chimeric protein induces immune tolerance in the human; and (2) following induction of immune tolerance, administering to the human a tapering regimen of the composition or the chimeric chimeric protein. In certain embodiments, induction of immune tolerance occurs when the titer of the inhibitory antibodies in the human is less than about 0.6 BU. In certain embodiments, induction of immune tolerance occurs when the titer of the inhibitory antibodies in the human is less than about 0.6 BU, and 60% recovery of clotting factor activity as monitored in plasma. In some embodiments of the present disclosure, the method further comprises (3) following the tapering regimen, administering to the human a prophylactic dose of the clotting factor. In certain aspects, the human has not been treated with a previous immune tolerance therapy against the clotting factor. The composition or the chimeric protein comprising a clotting factor and an Fc region can be administered to the human at any time it has been determined that the human has developed an inhibitor immune response, e.g., after measuring the level of an inhibitory immune response in the human. In other embodiments, the composition or the chimeric protein can be administered to the human who has not yet developed one or more inhibitor immune response to prevent development of an inhibitor immune response. In some embodiments, the composition or the chimeric protein is administered to the human who has a high likelihood (e.g., family history, genetic predisposition, or showing of a biomarker) of developing an inhibitor immune response. In some embodiments, the method further comprises measuring the level of an inhibitory immune response or the likelihood of developing an inhibitor immune response before the administration. In some embodiments, the composition or the chimeric protein comprising a clotting factor and an Fc region is administered to the human less than about 1 day, less than about 2 days, less than about 3 days, less than about 4 days, less than about 5 days, less than about 6 days, less than about 7 days, less than about 2 weeks, less than about 3 weeks, less than about 4 weeks, less than about 2 months, less than about 3 months, less than about 4 months, less than about 5 months, less than about 6 months, less than about 1 year, less than about 2 years, less than about 3 years, less than about 4 years, or less than about 5 years after it has been determined that the human has developed an inhibitor immune response or that the human has a likelihood of developing an inhibitor immune response, e.g., after measuring the level of an inhibitory immune response or the likelihood of developing an inhibitor immune response in the human. In certain embodiments, the composition or the chimeric protein comprising a clotting factor and an Fc region is administered to the human immediately after it has been determined that the human has developed an inhibitor immune response or that the human has a likelihood of developing an inhibitor immune response, e.g., after measuring the level of an inhibitory immune response or the likelihood of developing an inhibitor immune response in the human. In particular embodiments, the composition or the chimeric protein comprising a clotting factor and an Fc region is administered to the human less than about 5 minutes, less than about 10 minutes, less than about 15 minutes, less than about 20 minutes, less than about 30 minutes, less than about 45 minutes, less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, about 18 hours, or less than about 24 hours after it has been determined that the human has developed an inhibitor immune response or that the human has a likelihood of developing an inhibitor immune response, e.g., after measuring the level of an inhibitory immune response or the likelihood of developing an inhibitor immune response in the human. In particular embodiments, the composition or the chimeric protein comprising a clotting factor and an Fc region is administered to the human about 5 minutes, about 10 minutes, about 15 minutes, about 20 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, or about 24 hours after it has been determined that the human has developed an inhibitor immune response or that the human has a likelihood of developing an inhibitor immune response, e.g., after measuring the level of an inhibitory immune response or the likelihood of developing an inhibitor immune response in the human. In certain embodiments, the composition or the chimeric protein comprising a clotting factor and an Fc region is administered to the human less than about 1 day after it has been determined that the human has developed an inhibitor immune response or that the human has a likelihood of developing an inhibitor immune response, e.g., after measuring the level of an inhibitory immune response or the likelihood of developing an inhibitor immune response in the human.

Induction of an immune response can be continued until the level of inhibitor is lower than a certain level or until inhibitors are not detectable. In certain embodiments, the induction period can continue for at least about 24 weeks, at least about 26 weeks, at least about 28 weeks, at least about 30 weeks, at least about 32 weeks, at least about 34 weeks, at least about 36 weeks, at least about 38 weeks, at least about 40 weeks, at least about 42 weeks, at least about 44 weeks, at least about 46 weeks, at least about 48 weeks, at least about 50 weeks, at least about 52 weeks, at least about 54 weeks, at least about 56 weeks, at least about 58 weeks, at least about 60 weeks, at least about 62 weeks, at least about 64 weeks, at least about 66 weeks, at least about 68 weeks, at least about 70 weeks. In a particular embodiment, the induction period is less than 60 weeks.

The inhibitory immune response treated by the methods of the present invention can include any response within the human that negatively impacts one or more effects of a clotting factor treatment. In some embodiments, the inhibitory immune response comprises production of inhibitory antibodies against the clotting factor, e.g., inhibitory anti-FVIII antibodies. In certain embodiments, the method of the present disclosure further comprises measuring the titer of one or more inhibitory antibodies in the human before (e.g., at baseline) and after administering an effective amount of a composition or a chimeric protein comprising a clotting factor and an Fc region or a polynucleotide encoding the same. In some embodiments, titer of the inhibitory antibodies prior to the administration (e.g., at baseline) is at least about 0.6 Bethesda Units (BU). In certain embodiments, the titer of the inhibitory antibodies prior to the administration (e.g., at baseline) is at least about 1 BU, at least about 2 BU, at least about 3 BU, at least about 4 BU, at least about 5 BU, at least about 6 BU, at least about 7 BU, at least about 10 BU, at least about 20 BU, at least about 30 BU, at least about 40 BU, at least about 50 BU, at least about 100 BU, at least about 150 BU, or at least about 200 BU. In one particular embodiment, the titer of the inhibitory antibodies prior to the administration (e.g., at baseline) is at least about 5 BU.

In some embodiments, the methods of the present invention reduce the titer of inhibitory antibodies in a human subject relative to the titer of the inhibitory antibodies prior to the administration. In certain embodiments, the titer of the inhibitory antibodies after the administration is less than about 0.6 BU. In some embodiments, the titer of the inhibitory antibodies after the administration is less than about 0.5 BU, less than about 0.4 BU, less than about 0.3 BU, less than about 0.2 BU, or less than about 0.1 BU. In one particular embodiment, the titer of the inhibitory antibodies after the administration is 0 BU. In other embodiments, the titer of the inhibitory antibodies after the administration is less than 5 BU, less than 4 BU, less than 3 BU, less than 2 BU, less than 1 BU, less than 0.9 BU, less than 0.8 BU, less than 0.7 BU, or less than 0.6 BU.

In some embodiments, the administration increases the differentiation of macrophages in the human towards an M2-like phenotype, as compared to macrophage differentiation in untreated controls and humans treated with the clotting factor alone. In some embodiments, the M2-like phenotype comprises upregulation of the NRF2 pathway, the PPAR gamma pathway, or both the NRF2 pathway and the PPAR gamma pathway. In some embodiments, the M2-like phenotype comprises upregulation of CD206 (MRC1). In some embodiments, the M2-like phenotype comprises upregulation of ARG1. In some embodiments, the M2-like phenotype comprises upregulation of CD206 (MRC1) and ARG1.

In some embodiments, the administration results in greater expression of one or more genes in the human, relative to the expression of the one or more genes in an untreated subject or in a subject treated with the clotting factor alone. In some embodiments, the administration results in greater expression of one or more genes selected from the group consisting of Hmox1, PPAR gamma, LPL, EGR2, SLCO4A1, heme oxygenase 1 (HO-1), oxidative stress induced growth inhibitor 1 (OSGIN1), superoxide dismutase 1 (SOD1), glutathione-disulfide reductase (GSR), glutamate-cysteine ligase catalytic subunit (GCLC), glutamate-cysteine ligase modifier subunit (GCLM), NAD (P) H quinone dehydrogenase 1 (NQO1), fatty acid binding protein 5 (FABP5), B7-H3 (CD276), SLAM family member 3 (SLAMF3; lymphocyte antigen 9; LY9), SLAM family member 7 (SLAMF7), mannose receptor C-type 1 (MRC1), solute carrier family 12 member 4 (SLC12A), neuropilin 1 (NRP1), and any combination thereof. In some embodiments, the administration results in greater expression of one or more genes of the NRF2 pathway. In certain embodiments, the one or more genes of the NRF2 pathway are selected from the group consisting of HO-1, OSGIN1, SOD1, GSR, GCLC, GCLM, NQO1, and any combination thereof. In some embodiments, the administration results in greater expression of one or more genes of the PPAR gamma pathway. In some embodiments, the one or more genes of the PPAR gamma pathway are selected from the group consisting of PPAR gamma, LPL, FABP5, EGR2, and any combination thereof. In some embodiments, the administration results in greater expression of one or more genes selected from the group consisting of B7-H3 (CD276), SLAMF3, SLAMF7, MRC1, SLC12A, NRP1, and any combination thereof. In particular embodiments, the administration results in greater expression of the one or more genes relative to the expression of the one or more genes in an untreated human or a human administered the clotting factor alone, wherein the expression is at least about 1.5 fold greater, at least about 2 fold greater, at least about 2.5 fold greater, at least about 3 fold greater, at least about 3.5 fold greater, at least about 4 fold greater, at least about 4.5 fold greater, or at least about 5 fold greater.

In some embodiments, the differential expression of the one or more genes is observed less than 6 hours after the administration. In some embodiments, the differential expression is observed less than 12 hours after administration. In some embodiments, the differential expression is observed less than 18 hours after administration. In some embodiments, the differential expression is observed less than 24 hours after administration.

In some embodiments, the inhibitory immune response comprises a cell-mediated immune response. In certain embodiments, the cell-mediated immune response comprises the release of a cytokine. In some embodiments, the cytokine is any cytokine associated with an increased immune response. In some embodiments, the cytokine selected from the group consisting of IL-1, IL-6, IL-16, IL-12, IL-4, IL-17, tumor necrosis factor α (TNF-α), interferon α, interferon γ and any combination thereof. In one embodiment, the cell-mediated immune response comprises increased serum levels of IL-12. In another embodiment, the cell-mediated immune response comprises increased serum levels of IL-4. In another embodiment, the cell-mediated immune response comprises increased serum levels of IL-17. In another embodiment, the cell-mediated immune response comprises increased serum levels of TNF-α.

Various gene mutations have been linked with an increased risk of developing an inhibitory immune response. For example, the TNF-α-308G>A polymorphism within Hap2, which is associated with increased constitutive and inducible transcription levels of TNF has been linked with an increased risk of developing an inhibitory immune response. See Astermark et al., Blood 108:3739-3745 (2006), which is herein incorporated by reference in its entirety. Thus, in some embodiments, the human has a genetic polymorphism associated with increased TNF-α. In some embodiments, the polymorphism is the TNF-α-308G>A polymorphism. In some embodiments, the human has a polymorphism in an IL10 gene, e.g. a polymorphism associated with increased secretion of IL 10. In some embodiments, FVIII-Fc is administered to a subject with the allele 134 of the IL 10G microsatellite in the promote region of the IL10 gene. See Astermark et al. Hemostatis, Thrombosis, and Vascular Biology 108:3739-3745 (2006), which is herein incorporated by reference in its entirety.

In some embodiments, the human has a genetic polymorphism associated with decreased CTLA-4 (Cytotoxic T-Lymphocyte Antigen 4) expression. In some embodiments, the human has a mutation in DR15 (HLA-DR15) or DQB0602 MHC (major histocompatibility complex) class II molecules. Other MHC class II molecules associated with the development of an inhibitory immune response in subjects with hemophilia are A3, B7, C7, DQA0102, C2, DQA0103, DQB0603, and DR13 (see Inhibitors in Patients with Hemophilia, E. C. Rodriguez-Merchan & C. A. Lee, Eds., Blackwell Science, Ltd., 2002).

In some embodiments, the methods of the present disclosure reduce the level of one or more cytokine in the subject compared to the level of the one or more cytokines in the subject after a previous treatment with a polypeptide consisting of a FVIII polypeptide. In another embodiment, the methods of the present disclosure reduce the level of one or more cytokine in the subject compared to the level of the one or more cytokines in the subject prior to the administration. In other embodiments, the expression of one or more tolerogenic molecules is increased after the administration of the methods of the present disclosure relative to the expression level of the one or more tolerogenic molecules prior to the administration. In certain embodiments, the one or more tolerogenic molecules is selected from IL-10, TGF-β, IL-35, IDO-1, and any combination thereof.

In other embodiments, the immune response comprises a clinical symptom selected from the group consisting of: increased bleeding tendency, high clotting factor consumption, lack of response to clotting factor therapy, decreased efficacy of clotting factor therapy, shortened half-life of the clotting factor, and any combination thereof. In certain embodiments, the immune response comprises a clinical symptom selected from the group consisting of: increased bleeding tendency, high clotting factor consumption, lack of response to clotting factor therapy, decreased efficacy of clotting factor therapy, decreased recovery of clotting factor activity as monitored in the plasma, shortened half-life of the clotting factor, and any combination thereof.

In certain embodiments, the human was previously diagnosed as having an inhibitory immune response. Such a diagnosis can be made using any methods known in the art. For example, a human can be characterized as having an immune response to a clotting factor, e.g., a FVIII, if the human has one or more of the following: (a) a titer of inhibitory antibodies to the clotting factor greater than or equal to 0.6 BU; (b) increased serum levels of one or more cytokine selected from the group consisting of IL-12, IL-4, IL-17, and TNF-α; (c) increased bleeding tendency; (d) high clotting factor consumption; (e) a lack of response to clotting factor therapy; (f) decreased efficacy of clotting factor therapy; (g) shortened half-life of the clotting factor, and any combination thereof. In one particular embodiment, the human is characterized as having an immune response to a clotting factor if the human has a titer of inhibitory antibodies to the clotting factor greater than or equal to 0.6 BU.

In some embodiments, the human was previously diagnosed as having developed an inhibitory immune response to the clotting factor at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 27 months, at least about 30 months, at least about 33 months, at least about 36 months, at least about 39 months, at least about 42 months, at least about 45 months, at least about 48 years, at least about 51 months, at least about 54 months, at least about 57 months, at least about 60 months, at least about 6 years, at least about 7 years, at least about 8 years, at least about 10 years, at least about 15 years, or at least about 20 years prior to the administration. In one embodiment, the human was previously diagnosed as having developed an inhibitory immune response to the clotting factor at least about 5 years prior to the administration.

In some embodiments, the methods of the present disclosure provide an improved time to tolerance as compared to standard of care methods of inducing immune tolerance. The term "time to tolerance," as used herein refers to the amount of time between the administration of the first dose of the composition or the chimeric protein comprising a clotting factor and an Fc region and the development of immune tolerance in the human. Decreasing the time to tolerance can have significant benefits for the human, including but not limited to reducing the total financial burden required to achieve tolerance. In some embodiments, the time to tolerance is about 1 to about 24 weeks, about 1 to about 23 weeks, about 1 to about 22 weeks, about 1 to about 21 weeks, about 2 to about 20 weeks, about 2 to about 19 weeks, about 2 to about 18 weeks, about 2 to about 17 weeks, about 3 to about 16 weeks, about 3 to about 15 weeks, about 3 to about 14 weeks, about 3 to about 13 weeks, about 4 to about 12 weeks, about 4 to about 11 weeks, about 4 to about 10 weeks, about 4 to about 9 weeks, about 5 to about 8 weeks, about 5 to about 7 weeks, about 5 to about 6 weeks, about 1 to about 12 weeks, about 1 to about 11 weeks, about 1 to about 10 weeks, about 1 to about 9 weeks, about 1 to about 8 weeks, about 1 to about 7 weeks, about 1 to about 6 weeks, about 1 to about 5 weeks, or about 1 to about 4 weeks. In some embodiments, the time to tolerance is less than about 70 weeks, less than about 65 weeks, less than about 60 weeks, less than about 58 weeks, less than about 56 weeks, less than about 54 weeks, less than about 52 weeks, less than about 50 weeks, less than about 48 weeks, less than about 46 weeks, less than about 44 weeks, less than about 42 weeks, less than about 40 weeks, less than about 38 weeks, less than about 36 weeks, less than about 34 weeks, less than about 32 weeks, less than about 30 weeks, less than about 28 weeks, less than about 26 weeks, less than about 24 weeks, less than about 23 weeks, less than about 22 weeks, less than about 21 weeks, less than about 20 weeks, less than about 19 weeks, less than about 18 weeks, less than about 17 weeks, less than about 16 weeks, less than about 15 weeks, less than about 14 weeks, less than about 13 weeks, less than about 12 weeks, less than about 11 weeks, less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, or less than about 1 week. In certain embodiments, the time to tolerance is about 4 to about 12 weeks. In one embodiment, the time to tolerance is about 4 weeks. In another embodiment, the time to tolerance is about 12 weeks. In some embodiments, the time to tolerance is less than about 10 months. In some embodiments, the time to tolerance is less than about 9 months. In some embodiments, the time to tolerance is less than about 8 months. In some embodiments, the time to tolerance is less than about 7 months. In some embodiments, the time to tolerance is less than about 6 months. In some embodiments, the time to tolerance is less than about 5 months. In some embodiments, the time to tolerance is less than about 4 months. In some embodiments, the methods of the present disclosure result in a shorter time to tolerance in the human following treatment with a composition or the chimeric protein comprising a clotting factor and an Fc region as compared to the time to tolerance following treatment with the clotting factor alone.

In some embodiments, development of immune tolerance is characterized by a titer of an inhibitory antibody to the clotting factor of less than about 0.6 BU. In some embodiments, development of immune tolerance is characterized by a titer of an inhibitory antibody to the clotting factor of than about 0.5 BU. In some embodiments, development of immune tolerance is characterized by a titer of an inhibitory antibody to the clotting factor of less than about 0.4 BU. In some embodiments, development of immune tolerance is characterized by a titer of an inhibitory antibody to the clotting factor of less than about 0.3 BU. In some embodiments, development of immune tolerance is characterized by a titer of an inhibitory antibody to the clotting factor of less than about 0.2 BU. In some embodiments, development of immune tolerance is characterized by a titer of an inhibitory antibody to the clotting factor of less than about 0.1 BU. In some embodiments, development of immune tolerance is characterized by a titer of an inhibitory antibody to the clotting factor of 0.0 BU. In certain embodiments, the titer of inhibitory immune antibodies is observed at two consecutive measurements, e.g., in two consecutive weeks within a four-week period.

In some embodiments, the development of immune tolerance is characterized by incremental recovery >66% (e.g., incremental recovery of about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%). As used herein, "incremental recovery" refers to peak FVIII levels 15-30 minutes after infusion.

After the induction period and tapering period are completed, the subject can then be on prophylactic treatment of the chimeric protein. An exemplary prophylactic dosing regimen can be about 50 IU/kg of a chimeric protein every four days or about 25 IU/kg to about 65 IU/kg of a chimeric protein at three to five day intervals. For children less than 6 years of age, about 50 IU/kg of a chimeric protein twice weekly or about 25 IU/kg to about 65 IU/kg of a chimeric protein at three to five day intervals can be given. See ELOCTATE® Package Insert available at worldwideweb.eloctate.com/_assets/pdf/ELOCTATE_PI_January2017.pdf.

In some embodiments, the human treated using the methods of the present disclosure is receiving or has recently received an immunostimulatory therapy. For example, inhibitors have also been reported in HCV positive hemophilia A patients undergoing treatment with interferon as well as in HIV positive hemophilia A patients having an immune reconstitution inflammatory syndrome associated with anti-retroviral therapy. See Report of Expert Meeting on FVIII Products and Inhibitor Development, European Medicines Agency (Feb. 28, 2006-Mar. 2, 2006). Thus, in some embodiments, the human is receiving interferon therapy. In some embodiments, the human is receiving anti-viral therapy. In some embodiments, the human is receiving an anti-retroviral therapy and having an immune reconstitution inflammatory syndrome.

In certain embodiments, the human has had less than 150 exposure days (ED) to the clotting factor, e.g. FVIII. In one embodiment, the human has had less than 50 ED. In another embodiment, the human has had less than 20 ED.

Some aspects of the present disclosure are directed to methods of reducing the severity or occurrence of an allergic or anaphylactic reaction to a clotting factor in a subject in need thereof, comprising administering to the subject a composition or a chimeric protein comprising the clotting factor and an Fc region. In some embodiments, the administration of the composition or the chimeric protein reduces the severity of an anaphylactoid reaction to the clotting factor. In some embodiments, the administration of the composition or the chimeric protein reduces the severity of an allergic reaction to the clotting factor.

II.A. Chimeric Proteins

The methods of inducing immune tolerance disclosed herein are generally applicable to compositions or chimeric proteins comprising a clotting factor and an Fc region, wherein the clotting factor can be any known clotting factor, fragment thereof, or variant thereof, and wherein the Fc region can be any known Fc region, fragment thereof, or variant thereof. In some embodiments, the clotting factor is selected from the group consisting of factor VII (FVII), factor VIIa (FVIIa), factor VIII (FVIII), factor IX (FIX), factor X (FX), von Willebrand factor (VWF), or any combination thereof. Accordingly, the present disclosures regarding FVIIIFc chimeric proteins, and their uses, are equally applicable to other chimeric proteins comprising a clotting factor portion and an Fc portion. Any clotting factor or any fragment thereof or any variant thereof can be used in the methods of the present disclosure. Similarly, any Fc or any fragment thereof or any variant thereof can be used in the methods of the present disclosure. In some specific examples, the clotting factor portion of the chimeric protein is FVIII.

In some embodiments, the clotting factor and the Fc are present on separate polypeptide chains. In some embodiments, the clotting factor and the Fc are not linked or associated with each other by a covalent bond.

In other embodiments, the clotting factor can be a clotting factor mimic. Clotting factor mimics can manifest one or more clotting factor activities. For example, an antibody or antibody binding portion thereof can act like FVIII by binding to both factor IX and factor X. Such antibodies or antigen binding portions thereof can be used for the present methods if the antibodies or antigen biding portions thereof contains an Fc region. In another embodiment, the clotting factor is a peptide that has a FVIII activity.

In this respect, the present disclosure provides in general a method of inducing immune tolerance in a human comprising administering to the subject a composition or a chimeric protein comprises a clotting factor portion and an Fc portion.

II.A.1. FACTOR VIII

"Factor VIII," abbreviated throughout the instant application as "FVIII," as used herein, means functional FVIII polypeptide in its normal role in coagulation, unless otherwise specified. Thus, the term FVIII includes variant polypeptides that are functional. "A FVIII protein" is used interchangeably with FVIII polypeptide (or protein) or FVIII. Examples of the FVIII functions include, but are not limited to, an ability to activate coagulation, an ability to act as a cofactor for factor IX, or an ability to form a tenase complex with factor IX in the presence of $Ca^{2+}$ and phospholipids, which then converts factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632). The full length polypeptide and polynucleotide sequences are known, as are many functional fragments, mutants and modified versions. Various FVIII amino acid and nucleotide sequences are disclosed in, e.g., US Publication Nos. 2015/0158929 A1, 2014/0308280 A1, and 2014/0370035 A1 and International Publication No. WO 2015/106052 A1. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. FVIII variants include B domain deletions, whether partial or full deletions.

The FVIII portion in the clotting factor or the chimeric protein used herein has FVIII activity. FVIII activity can be measured by any known methods in the art. A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The chromogenic assay mechanism is based on the principles of the blood coagulation cascade, where activated FVIII accelerates the conversion of factor X into factor Xa in the presence of activated factor IX, phospholipids and calcium ions. The factor Xa activity is assessed by hydrolysis of a p-nitroanilide (pNA) substrate specific to factor Xa. The initial rate of release of p-nitroaniline measured at 405 nM is directly proportional to the factor Xa activity and thus to the FVIII activity in the sample.

The chromogenic assay is recommended by the FVIII and factor IX Subcommittee of the Scientific and Standardization Committee (SSC) of the International Society on Thrombosis and Hemostatsis (ISTH). Since 1994, the chromogenic assay has also been the reference method of the European Pharmacopoeia for the assignment of FVIII concentrate potency. Thus, in one embodiment, the chimeric protein comprising FVIII has FVIII activity comparable to a chimeric protein comprising mature FVIII or a BDD FVIII (e.g., ADVATE®, REFACTO®, or ELOCTATE®).

In another embodiment, the chimeric protein comprising FVIII of this disclosure has a factor Xa generation rate comparable to a chimeric protein comprising mature FVIII or a BDD FVIII (e.g., ADVATE®, REFACTO®, or ELOCTATE®).

In order to activate factor X to factor Xa, activated factor IX (factor IXa) hydrolyzes one arginine-isoleucine bond in factor X to form factor Xa in the presence of $Ca^{2+}$, membrane phospholipids, and a FVIII cofactor. Therefore, the interaction of FVIII with factor IX is critical in coagulation pathway. In certain embodiments, the chimeric protein comprising FVIII can interact with factor IXa at a rate comparable to a chimeric protein comprising mature FVIII sequence or a BDD FVIII (e.g., ADVATE®, REFACTO®, or ELOCTATE®).

In addition, FVIII is bound to von Willebrand factor while inactive in circulation. FVIII degrades rapidly when not bound to VWF and is released from VWF by the action of thrombin. In some embodiments, the chimeric protein comprising FVIII binds to von Willebrand factor at a level comparable to a chimeric protein comprising mature FVIII sequence or a BDD FVIII (e.g., ADVATE®, REFACTO®, or ELOCTATE®).

FVIII can be inactivated by activated protein C in the presence of calcium and phospholipids. Activated protein C cleaves FVIII heavy chain after Arginine 336 in the A1 domain, which disrupts a factor X substrate interaction site, and cleaves after Arginine 562 in the A2 domain, which enhances the dissociation of the A2 domain as well as disrupts an interaction site with the factor IXa. This cleavage also bisects the A2 domain (43 kDa) and generates A2-N (18 kDa) and A2-C (25 kDa) domains. Thus, activated protein C can catalyze multiple cleavage sites in the heavy chain. In one embodiment, the chimeric protein comprising FVIII is inactivated by activated Protein C at a level comparable to a chimeric protein comprising mature FVIII sequence or a BDD FVIII (e.g., ADVATE®, REFACTO®, or ELOCTATE®).

In other embodiments, the chimeric protein comprising FVIII has FVIII activity in vivo comparable to a chimeric protein comprising mature FVIII sequence or a BDD FVIII (e.g., ADVATE®, REFACTO®, or ELOCTATE®). In a particular embodiment, the chimeric protein comprising FVIII is capable of protecting a HemA mouse at a level comparable to a chimeric protein comprising mature FVIII sequence or a BDD FVIII (e.g., ADVATE®, REFACTO®, or ELOCTATE®) in a HemA mouse tail vein transection model.

A "B domain" of FVIII, as used herein, is the same as the B domain known in the art that is defined by internal amino acid sequence identity and sites of proteolytic cleavage by thrombin, e.g., residues Ser741-Arg1648 of mature human FVIII. The other human FVIII domains are defined by the following amino acid residues, relative to mature human FVIII: A1, residues Ala1-Arg372; A2, residues Ser373-Arg740; A3, residues Ser1690-Ile2032; C1, residues Arg2033-Asn2172; C2, residues Ser2173-Tyr2332 of mature FVIII. The sequence residue numbers used herein without referring to any SEQ ID Numbers correspond to the FVIII sequence without the signal peptide sequence (19 amino acids) unless otherwise indicated. The A3-C1-C2 sequence, also known as the FVIII heavy chain, includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art.

In one embodiment, the B domain of FVIII is deleted ("B-domain-deleted FVIII" or "BDD FVIII"). An example of a BDD FVIII is REFACTO® (recombinant BDD FVIII). In one particular embodiment the B domain deleted FVIII variant comprises a deletion of amino acid residues 746 to 1648 of mature FVIII.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563 and Int'l Publ. No. WO 2015106052 A1 (PCT/US2015/010738). In some embodiments, a B-domain-deleted FVIII sequence used in the methods of the present disclosure comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted factor VIII is the S743/Q1638 B-domain deleted factor VIII (SQ BDD FVIII) (e.g., factor VIII having a deletion from amino acid 744 to amino acid 1637, e.g., factor VIII having amino acids 1-743 and amino acids 1638-2332 of mature FVIII). In some embodiments, a B-domain-deleted FVIII used in the methods of the present disclosure has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted factor VIII may also contain a deletion of amino acids 771-1666 or amino acids 868-1562 of FVIII. Meulien P., et al. *Protein Eng.* 2 (4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In one particular embodiment, the B-domain-deleted FVIII comprises a deletion of amino acid residues 746 to 1648 of mature FVIII. In another embodiment, the B-domain-deleted FVIII comprises a deletion of amino acid residues 745 to 1648 of mature FVIII.

In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103 (a): 3412-3419 (2004), Kasuda, A, et al., *J. Thromb. Haemost.* 6:1352-1359 (2008), and Pipe, S. W., et al., *J. Thromb. Haemost.* 9:2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103 (a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9:2235-2242 (2011). In some embodiments, the BDD FVIII comprises single chain FVIII that contains a deletion in amino acids 765 to 1652 corresponding to the mature full length FVIII (also known as rVIII-SingleChain and AFSTYLA®). See U.S. Pat. No. 7,041, 635. Each of the foregoing deletions may be made in any FVIII sequence.

A great many functional FVIII variants are known, as is discussed above and below. In addition, hundreds of non-functional mutations in FVIII have been identified in hemophilia patients, and it has been determined that the effect of these mutations on FVIII function is due more to where they lie within the 3-dimensional structure of FVIII than on the nature of the substitution (Cutler et al., *Hum. Mutat.* 19:274-8 (2002)), incorporated herein by reference in its entirety. In addition, comparisons between FVIII from humans and other species have identified conserved residues that are likely to be required for function (Cameron et al., Thromb. Haemost. 79:317-22 (1998); U.S. Pat. No. 6,251, 632), incorporated herein by reference in its entirety.

In some embodiments, an effective amount of the chimeric protein comprising a FVIII and an Fc region is equivalent to an effective amount of the FVIII without the Fc region. In certain embodiments, the effective amount is from about 20 IU/Kg to about 400 IU/kg. In certain embodiments, the effective amount is from about 20 IU/Kg to about 300 IU/kg. In some embodiments, the effective amount is from about 50 IU/Kg to about 300 IU/kg. In some embodiments, the effective amount is from about 50 IU/kg to about 200 IU/kg. In some embodiments, the effective amount is about 100 IU/kg to about 300 IU/kg, about 100 IU/kg to about 200 IU/kg, about 100 IU/kg to about 290 IU/kg, about 100 IU/kg to about 280 IU/kg, about 100 IU/kg to about 270 IU/kg, about 100 IU/kg to about 260 IU/kg, about 100 IU/kg to about 250 IU/kg, about 100 IU/kg to about 240 IU/kg, about 100 IU/kg to about 230 IU/kg, from about 100 IU/kg to about 220 IU/kg, from about 100 IU/kg to about 210 IU/kg, from about 150 IU/kg to about 300 IU/kg, from about 150 IU/kg to about 290 IU/kg, from about 150 IU/kg to about 280 IU/kg, from about 150 IU/kg to about 270 IU/kg, from about 150 IU/kg to about 260 IU/kg, from about 150 IU/kg to about 250 IU/kg, from about 150 IU/kg to about 240 IU/kg, from about 140 IU/kg to about 250 IU/kg, from about 130 IU/kg to about 260 IU/kg, from about 120 IU/kg to about 270 IU/kg, from about 110 IU/kg to about 280 IU/kg. In one particular embodiment, the effective amount is from about 200 IU/kg to about 300 IU/kg. In another embodiment, the effective amount is from about 200 IU/kg to about 290 IU/kg. In other embodiments, the effective amount is from about 200 IU/kg to about 280 IU/kg, from about 200 IU/kg to about 270 IU/kg, from about 200 IU/kg to about 260 IU/kg, from about 200 IU/kg to about 250 IU/kg, from about 200 IU/kg to about 240 IU/kg, from about 200 IU/kg to about 230 IU/kg, from about 200 IU/kg to about 220 IU/kg, or from about 200 IU/kg to about 210 IU/kg.

In some embodiments, the effective amount is about 50 IU/kg, about 60 IU/kg, about 70 IU/kg, about 80 IU/kg, about 90 IU/kg, about 100 IU/kg, about 105 IU/kg, about 110 IU/kg, about 115 IU/kg, about 120 IU/kg, about 125 IU/kg, about 130 IU/kg, about 135 IU/kg, about 140 IU/kg, about 145 IU/kg, about 150 IU/kg, about 155 IU/kg, about 160 IU/kg, about 165 IU/kg, about 170 IU/kg, about 175 IU/kg, about 180 IU/kg, about 185 IU/kg, about 190 IU/kg, about 195 IU/kg, about 200 IU/kg, about 225 IU/kg, about 250 IU/kg, about 275 IU/kg, or about 300 IU/kg. In one particular embodiment, the effective amount is about 150 IU/kg. In another embodiment, the effective amount is about 200 IU/kg. In another embodiment, the effective amount is about 250 IU/kg. In another embodiment, the effective amount is about 50 IU/kg. In another embodiment, the effective amount is about 100 IU/kg.

The dosing interval when administering the chimeric protein comprising FVIII and an Fc region or a fragment thereof can be at least about one and one-half times longer than the dosing interval required for an equivalent dose of the clotting factor without the Fc domain. The dosing interval can be at least about one and one-half to six times longer, one and one-half to five times longer, one and one-half to four times longer, one and one-half to three times longer, or one and one-half to two times longer, than the dosing interval required for an equivalent dose of the FVIII without the Fc domain.

In some embodiments, the effective dose of the chimeric protein comprising a FVIII and an Fc region is administered to the human at a dosing interval of about a day, about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days. In some embodiments, the effective dose of the chimeric protein comprising a FVIII and an Fc region is administered to the human at a dosing interval of about 25 days, about 26 days, about 27 days, about 28 days, about 29 days, about 30 days, about 45 days, or about 60 days.

In some embodiments, the composition or the chimeric protein comprising a FVIII and an Fc region is administered at a dosing interval of about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 14 days, about 3 to about 14 days, about 4 to about 14 days, about 5 to about 14 days, about 6 to about 14 days, about 7 to about 14 days, about 8 to about 14 days, about 9 to about 14 days, about 10 to about 14 days, about 11 to about 14 days, about 12 to about 14 days, about 13 to about 14 days, or about 5 to about 10 days. In other embodiments, the composition or the chimeric protein comprising a FVIII and an Fc region is administered at a dosing interval of about 1 to about 21 days, about 1 to about 20 days, about 1 to about 19 days, about 1 to about 18 days, about 1 to about 17 days, about 1 to about 16 days, about 1 to about 15 days, about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 21 days, about 3 to about 21 days, about 4 to about 21 days, about 5 to about 21 days, about 6 to about 21 days, about 7 to about 21 days, about 8 to about 21 days, about 9 to about 21 days, about 10 to about 21 days, about 11 to about 21 days, about 12 to about 21 days, about 13 to about 21 days, about 14 to about 21 days, about 15 to about 21 days, about 16 to about 21 days, about 17 to about 21 days, about 18 to about 21 days, about 19 to about 21 days, about 20 to about 21 days, about 5 to about 10 days, about 10 to about 15 days, about 15 to about 20 days. In certain embodiments, the composition or the chimeric protein comprising a FVIII and an Fc region is administered at a dosing interval of about 2 to about 6 days. In another embodiment, the composition or the chimeric protein comprising a FVIII and an Fc region is administered at a dosing interval of about 3 to about 5 days.

In one embodiment, the effective dose is 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 64, or 65 IU/kg) and the dosing interval is once every 3-5, 3-6, 3-7, 3, 4, 5, 6, 7, or 8 or more days, or three times per week, or no more than three times per week. In another embodiment, the effective dose is 65 IU/kg and the dosing interval is once weekly, or once every 6-7 days. The doses can be administered repeatedly as long as they are necessary (e.g., at least 10, 20, 28, 30, 40, 50, 52, or 57 weeks, at least 1, 2, 3, 4, 5, 6, 7, 8, 9, or 10 years). In one particular embodiment, the effective dose is about 25-65 IU/kg and the dosing interval is once every 3-5 days.

In one embodiment, the effective amount is about 200 IU/kg and the effective amount is administered daily. In another embodiment, the effective amount is about 50 IU/kg, and the effective amount is administered about three times a week.

In certain embodiments, the effective amount or the effective dose is administered as a single dose. In some embodiments, the effective amount or the effective dose is administered in two or more doses throughout a day.

In some embodiments, the composition or the chimeric protein comprising a FVIII and an Fc region is administered to the human at a dose of about 200 IU/kg once daily until tolerization is observed. In some embodiments, the tolerization period extends for about 4 weeks to about 36 months. In some embodiments, the tolerization period extends for about 4 weeks, about 5 weeks, about 6 weeks, about 7 weeks, about 8 weeks, about 9 weeks, about 10 weeks, about 11 weeks, about 12 weeks, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 25 months, about 26 months, about 27 months, about 28 months, about 29 months, about 30 months, about 31 months, about 32 months, about 33 months, about 34 months, about 35 months, or about 36 months.

In certain embodiments, once immune tolerance is achieved, the human will be subjected to a tapering period. As used herein, the terms "tapering period" and "tapering regimen" are used interchangeably to refer to a dosing regimen wherein one or more tapering dose is administered. In some embodiments, the tapering period comprises administration of from about 20 IU/Kg to about 400 IU/kg. In certain embodiments, the tapering period comprises administration of from about 20 IU/Kg to about 300 IU/kg. In some embodiments, the tapering period comprises administration of from about 50 IU/Kg to about 300 IU/kg. In some embodiments, the tapering period comprises administration of from about 50 IU/Kg to about 100 IU/kg. In some embodiments, the tapering period comprises administration of from about 100 IU/kg to about 300 IU/kg, about 100 IU/kg to about 200 IU/kg, about 100 IU/kg to about 290 IU/kg, about 100 IU/kg to about 280 IU/kg, about 100 IU/kg to about 270 IU/kg, about 100 IU/kg to about 260 IU/kg, about 100 IU/kg to about 250 IU/kg, about 100 IU/kg to about 240 IU/kg, about 100 IU/kg to about 230 IU/kg, from about 100 IU/kg to about 220 IU/kg, from about 100 IU/kg to about 210 IU/kg, from about 150 IU/kg to about 300 IU/kg, from about 150 IU/kg to about 290 IU/kg, from about 150 IU/kg to about 280 IU/kg, from about 150 IU/kg to about 270 IU/kg, from about 150 IU/kg to about 260 IU/kg, from about 150 IU/kg to about 250 IU/kg, from about 150 IU/kg to about 240 IU/kg, from about 140 IU/kg to about 250 IU/kg, from about 130 IU/kg to about 260 IU/kg, from about 120 IU/kg to about 270 IU/kg, from about 110 IU/kg to about 280 IU/kg. In one particular embodiment, the tapering period comprises administration of from about 200 IU/kg to about 300 IU/kg. In another embodiment, the tapering period comprises administration of from about 200 IU/kg to about 290 IU/kg. In other embodiments, the tapering period comprises administration of from about 200 IU/kg to about 280 IU/kg, from about 200 IU/kg to about 270 IU/kg, from about 200 IU/kg to about 260 IU/kg, from about 200 IU/kg to about 250 IU/kg, from about 200 IU/kg to about 240 IU/kg, from about 200 IU/kg to about 230 IU/kg, from about 200 IU/kg to about 220 IU/kg, or from about 200 IU/kg to about 210 IU/kg. In another embodiment, the tapering regimen comprises administering a tapering dose of about 50 IU/kg to about 100 IU/kg of the composition or the chimeric protein. In one particular embodiment, the tapering regimen comprises administering a tapering dose of about 50 IU/kg of the composition or, the chimeric protein. In another embodiment, the tapering regimen comprises administering a tapering dose of about 150 IU/kg of the composition or the chimeric protein. In another embodiment, the tapering regimen comprises administering a tapering dose of about 125 IU/kg of the composition or the chimeric protein. In another particular embodiment, the tapering regimen comprises administering a tapering dose of about 100 IU/kg of the composition or the chimeric protein. In another embodiment, the tapering regimen comprises administering a tapering dose of about 90 IU/kg of the composition or the chimeric protein. In another embodiment, the tapering regimen comprises administering a tapering dose of about 80 IU/kg of the composition or the chimeric protein. In another embodiment, the tapering regimen comprises administering a tapering dose of about 75 IU/kg of the composition or the chimeric protein. In another embodiment, the tapering regimen comprises administering a tapering dose of about 70 IU/kg of the composition or the chimeric protein. In another embodiment, the tapering regimen comprises administering a tapering dose of about 60 IU/kg of the composition or the chimeric protein. In another embodiment, the tapering regimen comprises administering a tapering dose of about 40 IU/kg of the composition or the chimeric protein. In another embodiment, the tapering regimen comprises administering a tapering dose of about 30 IU/kg of the composition or the chimeric protein. In another embodiment, the tapering regimen comprises administering a tapering dose of about 25 IU/kg of the composition or the chimeric protein. In another embodiment, the tapering regimen comprises administering a tapering dose of about 20 IU/kg of the composition or the chimeric protein. In another embodiment, the tapering regimen comprises administering a tapering dose of about 10 IU/kg of the composition or the chimeric protein.

In some embodiments, the tapering period comprises administration of the composition or the chimeric protein every day. In other embodiments, the tapering period comprises administration of the composition or the chimeric protein once about every two days, once about every three days, once about every four days, once about every five days, once about every six days, once about every seven days, once about every eight days, once about every nine days, once about every ten days, once about every eleven days, once about every twelve days, once about every thirteen days, or one about every fourteen days.

In certain embodiments, the tapering dose is administered once a day, once every other day, or three times every week. In some embodiments, the tapering dose is administered for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, at least about 20 weeks, at least about 21 weeks, at least about 22 weeks, at least about 23 weeks, at least about 24 weeks, at least about 25 weeks, at least about 26 weeks, at least about 27 weeks, at least about 28 weeks, at least about 29 weeks, at least about 30 weeks, at least about 31 weeks, or at least about 32 weeks. In a particular embodiment, the tapering dose is administered for about 16 weeks or less.

In certain embodiments, the dose of the composition or the chimeric protein is gradually reduced during the tapering period and the dosing interval remains the same. In other embodiments, the dosing interval is increased during the tapering period and the dose of the composition or the chimeric protein remains the same. In some embodiments, the dose of the composition or the chimeric protein is gradually reduced during the tapering period and the dosing interval is gradually increased.

In one particular embodiment, the tapering period comprises administration of about 200 IU/kg of the chimeric clotting factor every other day, followed by further reduction in dosage and dosing interval. In other embodiments, the doses of the chimeric protein required for a day can be divided up into two doses, three doses, or more. For example, about 200 IU/kg of the chimeric protein can be divided up to about 100 IU/kg twice a day, about 70 IU/kg three times a day, or about 50 IU/kg four times a day.

In some embodiments, the tapering period extends from about 1 month to about 6 months. In certain embodiments, the tapering period extends for about 1 month, about 2 months, about 3 months, about 4 months, about 5 months, or about 6 months. In one particular embodiment, the tapering period extends for about 4 months.

In certain embodiments, the tapering regimen comprises administering a tapering dose of the chimeric protein of about 100 IU/kg once a day from week 1 to week 6 following immune tolerance. In certain embodiments, the tapering regimen further comprises administering a tapering dose of the chimeric protein of about 100 IU/kg once every other day from week 6 to week 12 following immune tolerance. In certain embodiments, the tapering regimen further comprises administering a tapering dose of the chimeric protein of about 50 IU/kg once every other day from week 12 to week 16.

In some embodiments, the tapering period is followed by a follow-up period. In some embodiments, the follow-up period comprises prophylactic treatment with composition or the chimeric protein. In some embodiments, the follow-up period comprises prophylactic treatment with the clotting factor. The clotting factor used in the follow-up period can be selected from the clotting factor used in the tolerization and tapering periods, with or without the Fc region, and any variants thereof. The clotting factor can include, but is not limited to, a native clotting factor, any variant described herein (e.g., B domain deleted variants of FVIII), and any chimeric clotting factor described herein (e.g., FVIII-Fc, FVIII-albumin, etc.). In certain embodiments, the prophylactic treatment comprises administration of the approved prophylactic dose of, e.g., recombinant FVIIIFc. In some embodiments, the prophylactic treatment comprises 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, or 65 IU/kg) and the dosing interval is once every 3-5, 3-6, 3-7, 3, 4, 5, 6, 7, or 8 or more days, or three times per week, or no more than three times per week. In another embodiment, the prophylactic treatment comprises is 65 IU/kg and the dosing interval is once weekly, or once every 6-7 days. In another embodiment, the prophylactic treatment comprises administering a dose of the clotting factor of 50 IU/kg. In another embodiment, the prophylactic treatment comprises administering a dose of the clotting factor of 50 IU/kg and the dosing interval is about three times per week. In one particular embodiment, the prophylactic treatment comprises about 25-65 IU/kg and the dosing interval is once every 3-5 days. In certain embodiments, the follow-up period extends for about 8 months.

In one particular embodiment, the chimeric protein, e.g., FVIIIFc, is administered at about 200 IU/kg/day until immune tolerance is observed, e.g., when the titer of the inhibitory antibodies in the human is less than about 0.6 BU; then, following immune tolerance, a tapering regimen is administered, wherein the tapering regimen comprises administering a tapering dose of the chimeric protein, e.g., FVIIIFc, of about 100 IU/kg once a day from week 1 to week 6 following immune tolerance, administering a tapering dose of the chimeric protein, e.g., FVIIIFc, of about 100 IU/kg once every other day from week 6 to week 12 following immune tolerance, and administering a tapering dose of the chimeric protein, e.g., FVIIIFc, of about 50 IU/kg once every other day from week 12 to week 16; and then, following the tapering regimen, a prophylactic dose of the clotting factor of about 50 IU/kg is administered about three times per week.

The composition or the chimeric protein comprising a FVIII and an Fc region, can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. The composition can be also for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate.

In some embodiments, the chimeric protein comprising a FVIII and an Fc region used in the methods of the present invention is formulated in a pharmaceutical composition comprising: (a) the chimeric protein; (b) one or more stabilizing agents selected from sucrose, trehalose, raffinose, arginine, or mixture thereof; (c) sodium chloride (NaCl); (d) L-histidine; (e) calcium chloride; and (f) polysorbate 20 or polysorbate 80. In certain embodiments, the pharmaceutical composition comprises: (a) 50 IU/ml to 2500 IU/ml of the chimeric protein; (b) 10 mg/ml to 25 mg/ml of sucrose; (c) 8.8 mg/ml to 14.6 mg/ml sodium chloride (NaCl); (d) 0.75 mg/ml to 2.25 mg/ml L-histidine; (e) 0.75 mg/ml to 1.5 mg/ml calcium chloride dihydrate; and (f) 0.08 mg/ml to 0.25 mg/ml polysorbate 20 or polysorbate 80. In some examples, the pharmaceutical composition used in the methods of the present disclosure is lyophilized.

In some embodiments, the pharmaceutical composition does not comprise an immune cell. In some embodiments, the pharmaceutical composition does not comprise a cell.

In certain embodiments, the human treated using the methods of the present disclosure previously developed a FVIII inhibitory immune response. In some embodiments, the previously developed FVIII inhibitory response developed in response to a recombinant FVIII. In some embodiments, the previously developed FVIII inhibitory response developed in response to a FVIII product selected from the group consisting of ADVATE®, RECOMBINATE®, KOGENATE FS®, HELIXATE FS®, XYNTHA/REFACTO AB®, HEMOFIL-M®, MONARC-M®, MONOCLATE-P®, HUMATE-P®, ALPHANATE®, KOATE-DVI®, AFSTYLA®, AND HYATE:C®.

In some embodiments, once tolerization is reached according to decreased titers of inhibitory antibodies, the serum level of the clotting factor is maintained from about 100 IU/dL to about 200 IU/dL. In some embodiments, the effective amount of the composition or the chimeric protein is reduced prior to the start of the tapering regimen to maintain a serum level of the clotting factor from about 100 IU/dL to about 200 IU/dL. In certain embodiments, the effective amount of the composition or the chimeric protein is reduced to about 175 IU/kg/day if the serum level of the clotting factor is greater than or equal to 200 IU/dL. In certain embodiments, the effective amount of composition or the chimeric protein is reduced to about 150 IU/kg/day if the serum level of the clotting factor is greater than or equal to 200 IU/dL. In certain embodiments, the effective amount of the composition or the chimeric protein is reduced to about 125 IU/kg/day if the serum level of the clotting factor is greater than or equal to 200 IU/dL. In certain embodiments, the effective amount of the composition or the chimeric protein is reduced to about 100 IU/kg/day if the serum level of the clotting factor is greater than or equal to 200 IU/dL. In certain embodiments, the effective amount of the composition or the chimeric protein is reduced to about 75 IU/kg/day if the serum level of the clotting factor is greater than or equal to 200 IU/dL. In certain embodiments, the effective amount of the composition or the chimeric protein is reduced to about 50 IU/kg/day if the serum level of the clotting factor is greater than or equal to 200 IU/dL. In certain embodiments, the effective amount of the composition or the chimeric protein is reduced to about 25 IU/kg/day if the serum level of the clotting factor is greater than or equal to 200 IU/dL.

Certain aspects of the present disclosure are directed to methods of inducing immune tolerance in a human with hemophilia, comprising administering to the human about 200 IU/kg of a composition or a chimeric protein comprising a clotting factor and an Fc region. In certain embodiments, the composition or the chimeric protein is administered every other day. In other embodiments, the composition or the chimeric protein is administered daily.

In other aspects, the present disclosure is directed to methods of inducing immune tolerance in a human with hemophilia, comprising administering to the human about 202 IU/kg of a composition or a chimeric protein comprising a clotting factor and an Fc region. In certain embodiments, the composition or the chimeric protein is administered daily.

In other aspects, the present disclosure is directed to methods of inducing immune tolerance in a human with hemophilia, comprising administering to the human about 150 IU/kg of a composition or the chimeric protein comprising a clotting factor and an Fc region. In certain embodiments, the composition or the chimeric protein is administered daily.

In other aspects, the present disclosure is directed to methods of inducing immune tolerance in a human with hemophilia, comprising administering to the human about 130 IU/kg of a composition or a chimeric protein comprising a clotting factor and an Fc region. In certain embodiments, the composition or the chimeric protein is administered daily.

In other aspects, the present disclosure is directed to methods of inducing immune tolerance in a human with hemophilia, comprising administering to the human about 115 IU/kg of a composition or a chimeric protein comprising a clotting factor and an Fc region. In certain embodiments, the composition or the chimeric protein is administered every other day.

In other aspects, the present disclosure is directed to methods of inducing immune tolerance in a human with hemophilia, comprising administering to the human about 100 IU/kg of a composition or a chimeric protein comprising a clotting factor and an Fc region. In certain embodiments, the composition or the chimeric protein is administered daily. In other embodiments, the composition or the chimeric protein is administered three times per week.

In other aspects, the present disclosure is directed to methods of inducing immune tolerance in a human with hemophilia, comprising administering to the human about 102 IU/kg of a composition or a chimeric protein comprising a clotting factor and an Fc region. In certain embodiments, the composition or the chimeric protein is administered every other day.

In other aspects, the present disclosure is directed to methods of inducing immune tolerance in a human with hemophilia, comprising administering to the human about 96 IU/kg of a composition or a chimeric protein comprising a clotting factor and an Fc region. In certain embodiments, the composition or the chimeric protein is administered daily.

In other aspects, the present disclosure is directed to methods of inducing immune tolerance in a human with hemophilia, comprising administering to the human about 85 IU/kg of a composition or a chimeric protein comprising a clotting factor and an Fc region. In certain embodiments, the composition or the chimeric protein is administered daily.

In other aspects, the present disclosure is directed to methods of inducing immune tolerance in a human with hemophilia, comprising administering to the human about 50 IU/kg of a composition or a chimeric protein comprising a clotting factor and an Fc region. In certain embodiments, the composition or the chimeric protein is administered three times per week.

Certain aspects of the present disclosure are directed to methods of inducing immune tolerance in a human with hemophilia, comprising (1) administering to the human about 200 IU/kg of a composition or a chimeric protein comprising a clotting factor and an Fc region, wherein the composition or the chimeric protein induces immune tolerance in the human; and (2) following induction of immune tolerance, administering to the human a tapering regimen of the composition or the chimeric protein.

II.A.2 Fc

In some embodiments, the compositions, chimeric proteins, and/or the clotting factors of the disclosure include an Fc domain or a portion thereof that binds to an Fc receptor (FcR; e.g., FcRn). In some embodiments, the Fc domain is fused to the clotting factor, e.g., as part of a chimeric protein comprising a clotting factor and an Fc region. In other embodiments, the Fc domain is fused to a polypeptide other than the clotting factor, wherein the composition comprises a (1) clotting factor and (2) a chimeric protein comprising an Fc domain and an additional polypeptide. The Fc domain or a portion thereof can improve pharmacokinetic or pharmacodynamic properties of the chimeric protein. In certain embodiments, the Fc domain or a portion thereof extends a half-life of a molecule fused to the Fc domain or a portion thereof.

As used herein, the term "Fc domain" of "Fc region" as used herein, means functional FcR (e.g., FcRn) binding partners, unless otherwise specified. The Fc domain is the portion of a polypeptide which corresponds to the Fc domain of native Ig, i.e., as formed by the dimeric association of the respective Fc domains of its two heavy chains. A native Fc domain forms a homodimer with another Fc domain. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

Fc regions useful in the present invention encompass molecules that can specifically bind an FcR, including whole IgG, the Fc fragment of IgG, and other fragments that include the complete binding region of an FcR. The region of the Fc portion of IgG that binds to, e.g., the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The Fc regions include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of Igs or Ig fragments, or regions, are all based on Kabat et al. 1991, Sequences of Proteins of Immunological Interest, U.S. Department of Public Health, Bethesda, Md.

Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer FcR binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion.

FcR binding portions may be derived from heavy chains of any isotype, including IgG1, IgG2, IgG3 and IgG4. In one embodiment, an FcR binding portion from an antibody of the human isotype IgG1 is used. In another embodiment, an FcR binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising the wild-type Fc domain (e.g., an improvement or reduction in the ability of the Fc region to bind to Fc receptors (e.g., improvement or reduction in binding to FcγRI, FcγRII, or FcγRIII), complement proteins (e.g. C1q), or other Fc binding partners (e.g., DC-SIGN), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US2007/0248603, US2007/0286859, US2008/0057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region can be modified according to well recognized procedures such as site directed mutagenesis and the like to yield modified Fc fragments or portions thereof that will be bound by FcγRIIB and/or DC-SIGN. Such modifications include modifications remote from the FcγRIIB and/or DC-SIGN contact sites as well as modifications within the contact sites that preserve or even enhance binding to the FcγRIIB and/or DC-SIGN. For example, the following single amino acid residues in human IgG1 Fc (Fc γ1) can be substituted without significant loss of Fc binding affinity for FcγRIIB and/or DC-SIGN: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

Certain of the above mutations may confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 to the corresponding sequence from IgG2 "PVA" (with one amino acid deletion). It has been shown that FcγRI, FcγRII, and FcγRIII, which mediate various effector functions, will not bind to IgG1 when such mutations have been introduced. Ward and Ghetie 1995, Therapeutic Immunology 2:77 and Armour et al. 1999, Eur. J. Immunol. 29:2613.

In one embodiment, the Fc domain or a portion thereof is a polypeptide including SEQ ID NO: 3 of U.S. Pat. No. 5,739,277 and optionally further including a sequence selected from SEQ ID NOs: 11, 1, 2, and 31 of U.S. Pat. No. 5,739,277.

In certain embodiments, the Fc domain or a portion thereof is hemi-glycosylated. For example, the chimeric protein comprising two Fc regions may contain a first, glycosylated, Fc region (e.g., a glycosylated CH2 region) and a second, aglycosylated, Fc region (e.g., an aglycosylated CH2 region). In one embodiment, a linker may be interposed between the glycosylated and aglycosylated Fc regions. In another embodiment, the Fc region is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an Fc domain or a portion thereof (e.g., Fc variants), which alters the antigen-independent effector functions of Fc domain, in particular the circulating half-life of the protein.

Such proteins exhibit either increased or decreased binding to FcR when compared to proteins lacking these substitutions and, therefore, have an increased or decreased half-life in serum, respectively. Fc variants with improved affinity for FcR are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcR binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibits reduced transport across the blood brain barrier (BBB) from the brain, into the vascular space. In one embodiment, a protein with altered FcR binding comprises at least one Fc region (e.g., one or two Fc regions) having one or more amino acid substitutions within the "FcR binding loop" of an Ig constant region. The FcR binding loop is, in one embodiment, comprised of amino acid residues 280-299 (according to EU numbering) of a wild-type, full-length, Fc region. In other embodiments, an Ig constant region or a portion thereof in a chimeric protein of the invention having altered FcR binding affinity comprises at least one Fc region having one or more amino acid substitutions within the 15 Å FcR "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, an Fc domain or a portion thereof of the invention having altered FcR binding affinity comprises at least one Fc region having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcR binding activity are disclosed in International PCT Publication No. WO05/047327 which is incorporated by reference herein.

An Fc region used in the invention may also comprise an art recognized amino acid substitution which alters the glycosylation of the chimeric protein. For example, the Fc region of the chimeric protein linked to a FVIII protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions of the protein of the invention may differ in sequence at one or more amino acid positions. For example, at least two of the Fc regions may differ at about 5 amino acid positions (e.g., 1, 2, 3, 4, or 5 amino acid positions), about 10 positions, about 15 positions, about 20 positions, about 30 positions, about 40 positions, or about 50 positions).

In some embodiments, a chimeric protein used in the methods of the present disclosure comprises more than one polypeptide chain. In some embodiments, the chimeric protein comprises two polypeptide chains. In certain embodiments, the first polypeptide chain comprises a clotting factor and a first Fc region, and the second polypeptide chain comprises a second Fc region. In certain embodiments, the first Fc region and the second Fc region are associated by a covalent bond. In one embodiment, the first Fc region and the second Fc region are associated by a peptide bond. In another embodiment, the first Fc region and the second Fc region are associated by a disulfide bond.

In one particular embodiment, the chimeric protein comprises a factor VIII portion and a von Willebrand factor (VWF) portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other. In certain embodiments, the VWF portion comprises the D' and D3 domains of VWF. In one embodiment, the first polypeptide, the second polypeptide, or both the first polypeptide and the second polypeptide further comprise one or more half-life extending moieties.

An Fc region or a portion thereof for producing a chimeric protein used in the methods of the present disclosure may be obtained from a number of different sources. In some embodiments, an Fc region or a portion thereof is derived from a human Ig. It is understood, however, that the Fc region or a portion thereof may be derived from an Ig of another mammalian species, including for example, a rodent (e.g. a mouse, rat, rabbit, guinea pig) or non-human primate (e.g. chimpanzee, macaque) species. Moreover, the Fc region or a portion thereof may be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Fc region gene sequences (e.g., human Fc gene sequences) are available in the form of publicly accessible deposits. Fc sequences can be selected having a particular effector function (or lacking a particular effector function) or with a particular modification to reduce immunogenicity. Many sequences of antibodies and antibody-encoding genes have been published and suitable Fc region sequences can be derived from these sequences using art recognized techniques. The genetic material obtained using any of the foregoing methods may then be altered or synthesized to obtain chimeric proteins used in the methods of the present disclosure. It will further be appreciated that the scope of this invention encompasses alleles, variants and mutations of constant region DNA sequences.

The sequences of the Fc or a portion thereof can be cloned, e.g., using the polymerase chain reaction and primers which are selected to amplify the domain of interest. To clone a sequence of the Fc region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

II.B. Half-Life Extending Moieties

In some embodiments, a chimeric protein used in the methods of the present disclosure further comprises one or more half-life extending moieties. Half-life of a clotting factor can be determined by any method known to those of skill in the art, e.g., FVIII activity assays (chromogenic assay or one stage clotting aPTT assay) to detect plasma FVIII activity levels or FVIII ELISA to detect plasma FVIII antigen level. In a particular embodiment, half-life of the clotting activity of a clotting factor is determined by one stage clotting assay. In a more particular embodiment, half-life of the clotting activity of a clotting factor is determined in mice, either HemA mice or FVIII and von Willebrand factor double knockout (DKO) mice.

In certain aspects, a heterologous moiety which increases half-life of the clotting factor of the invention comprises, without limitation, a heterologous polypeptide such as albumin, an immunoglobulin Fc region, an XTEN sequence, the C-terminal peptide (CTP) of the β subunit of human chorionic gonadotropin, a PAS sequence, a HAP sequence, a transferrin, albumin-binding moieties, or any fragments, derivatives, variants, or combinations of these polypeptides. In other related aspects a half-life extending moiety can include an attachment site for a non-polypeptide moiety such as polyethylene glycol (PEG), hydroxyethyl starch (HES), polysialic acid, or any derivatives, variants, or combinations of these moieties. In certain embodiments, the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof. In some embodiments, the half-life extending moiety does not comprise an XTEN. In other embodiments, the half-life extending moiety comprises an XTEN.

In other embodiments, a chimeric protein of the invention is conjugated to one or more polymers. The polymer can be water-soluble or non-water-soluble. The polymer can be covalently or non-covalently attached to the clotting factor, the Fc, or to other moieties conjugated to either the clotting factor or the Fc. Non-limiting examples of the polymer can be poly(alkylene oxide), poly(vinyl pyrrolidone), poly(vinyl alcohol), polyoxazoline, or poly(acryloylmorpholine). Additional types of, e.g., polymer-conjugated FVIII are disclosed in U.S. Pat. No. 7,199,223, which is disclosed by reference in its entirety.

In certain aspects, a chimeric protein of the invention can comprise one, two, three or more half-life extending moieties, which can each be the same or different molecules.

In some embodiments, the half-life extending moiety is fused to the N-terminus or the C-terminus of the chimeric protein. In some embodiments, the half-life extending moiety is fused to the N-terminus or the C-terminus of the clotting factor. In some embodiments, the half-life extending moiety is fused to the N-terminus or the C-terminus of the Fc. In certain embodiments, the half-life extending moiety is inserted within the clotting factor of the chimeric protein.

In some embodiments, the chimeric protein comprises FVIII or a portion thereof, and the half-life extending moiety is inserted within the FVIII at one or more positions disclosed in U.S. Patent Publ. No. 2015-0158929 A1 and/or Int'l Publication No. WO 2015106052 A1, which are incorporated by reference herein in their entirety. In one particular embodiment, the half-life extending moiety is inserted within the B domain (or a fragment thereof) of the FVIII. In one particular embodiment, the half-life extending moiety is inserted within the FVIII immediately downstream of amino acid residue 745 of mature FVIII.

II.B.1. Albumins

In certain aspects, a chimeric protein used in the methods of the present disclosure comprises at least one albumin polypeptide or fragment, variant, or derivative thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

The albumin-binding polypeptides (ABPs) can compromise, without limitation, bacterial albumin-binding domains, albumin-binding peptides, or albumin-binding antibody fragments that can bind to albumin. Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides are disclosed in Dennis et al., J. Biol. Chem. 2002, 277:35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties.

In certain aspects, a chimeric protein used in the methods of the present disclosure comprises at least one attachment site for a non-polypeptide small molecule, variant, or derivative that can bind to albumin thereof. For example, the chimeric protein can include one or more organic albumin-binding moieties. An example of such albumin-binding moieties is 2-(3-maleimidopropanamido)-6-(4-(4-iodophenyl) butanamido) hexanoate ("Albu" tag) as disclosed by Trussel et al., Bioconjugate Chem. 20:2286-2292 (2009).

II.B.2. XTENS

In certain aspects, a chimeric protein used in the methods of the present disclosure comprises at least one XTEN polypeptide or fragment, variant, or derivative thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties, e.g., when fused with or inserted into the clotting factor of the chimeric protein. Such desirable properties include but are not limited to enhanced pharmacokinetic parameters and solubility characteristics.

An XTEN sequence fused with or inserted into the clotting factor of the chimeric protein used in the methods of the present disclosure can confer to the chimeric protein one or more of the following advantageous properties: conformational flexibility, enhanced aqueous solubility, high degree of protease resistance, low immunogenicity, low binding to mammalian receptors, or increased hydrodynamic (or Stokes) radii. In certain aspects, an XTEN sequence can increase pharmacokinetic properties such as longer half-life (e.g., in vivo half-life) or increased area under the curve (AUC), so that the chimeric protein stays in vivo and has procoagulant activity for an increased period of time compared to the chimeric protein without the XTEN.

Examples of XTEN sequences that can be inserted into recombinant FVIII proteins of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, or WO 2015106052 A1, each of which is incorporated by reference herein in its entirety.

II.B.3. VWF or a Fragment Thereof

In certain aspects, a chimeric protein used in the methods of the present disclosure comprises at least one VWF polypeptide or fragment, variant, or derivative thereof. VWF (also known as F8VWF) is a large, multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D'/D3 domain (which binds to factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (BHCG)).

In one embodiment, the VWF polypeptide is a VWF fragment. The term "a VWF fragment" as used herein includes, but is not limited to, functional VWF fragments comprising a D' domain and a D3 domain, which are capable of inhibiting binding of endogenous VWF to FVIII. In one embodiment, the chimeric protein used in the methods of the present disclosure comprises a clotting factor, an Fc region, and a VWF fragment, wherein the clotting factor comprises FVIII, and wherein the VWF fragment binds to the FVIII protein. In another embodiment, the VWF fragment blocks the VWF binding site on the FVIII protein, thereby inhibiting interaction of the FVIII protein with endogenous VWF. The VWF fragments include derivatives, variants, mutants, or analogues that retain these activities of VWF. In certain embodiments, the VWF fragment comprises the D' domain and D3 domain of VWF.

The 2813 monomer amino acid sequence for human VWF is reported as Accession Number _NP_000543.2_ in Genbank. The nucleotide sequence encoding the human VWF is reported as Accession Number_NM_000552.3_ in Genbank.

In certain embodiments, the VWF protein useful herein can be further modified to improve its interaction with FVIII, e.g., to improve binding affinity to FVIII. In other embodiments, The VWF proteins useful for the invention can have other modifications, e.g., the protein can be pegylated, glycosylated, hesylated, or polysialylated. Example VWF sequences useful in the methods of the present disclosure are provided, e.g., in U.S. Publication Nos. US 2015/0023959 A1, US 2015/0266943 A1, and US 2015/0158929. In certain embodiments, the VWF protein or a fragment thereof is fused to or co-administered with an FcRn binding partner. In some embodiments, the VWF protein or a fragment thereof is fused to an Fc or co-administered with an Fc or a polypeptide comprising an Fc. In some embodiments, the VWF protein or a fragment thereof is fused to an albumin or co-administered with an albumin or a polypeptide comprising an albumin.

II.B.4. CTP

In certain aspects, a chimeric protein used in the methods of the present disclosure comprises at least one C-terminal peptide (CTP) of the β subunit of human chorionic gonadotropin or fragment, variant, or derivative thereof. CTP peptides are known to increase the half-life of that protein. See, e.g., U.S. Pat. No. 5,712,122, incorporated by reference herein in its entirety. Non-limiting exemplary CTP peptides are disclosed in U.S. Patent Application Publication No. US 2009/0087411 A1, incorporated by reference.

II.B.5. PAS

In certain aspects, a chimeric protein used in the methods of the present disclosure comprises at least one PAS peptide or fragment, variant, or derivative thereof. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline cab be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides are disclosed in, e.g., US Pat. Publ. No. 2010/0292130 A1; PCT Appl. Publ. No. WO 2008/155134 A1; and European issued patent EP2173890.

II.B.6. HAP

In certain aspects, a chimeric protein used in the methods of the present disclosure comprises at least one homo-amino acid polymer (HAP) peptide or fragment, variant, or derivative thereof. A HAP peptide can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. A HAP sequence is capable of extending half-life of a moiety fused to or linked to the HAP sequence. Non-limiting examples of the HAP sequence includes, but are not limited to (Gly)$_n$, (Gly$_4$Ser)$_n$ or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et al., Protein Eng. Design Selection, 20:273-284 (2007).

II.B.7. Transferrin

In certain aspects, a chimeric protein used in the methods of the present disclosure comprises at least one transferrin peptide or fragment, variant, or derivative thereof. Any transferrin can fused with the chimeric protein used in the methods of the present disclosure. As an example, wild-type human Tf (Tf) is a 679 amino acid protein, of approximately 75 kDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., Trends Pharmacol. Sci. 23:206-209 (2002)). Transferrin fusion proteins have been studied for half-life extension, targeted deliver for cancer therapies, oral delivery and sustained activation of proinsulin (Brandsma et al., Biotechnol. Adv., 29:230-238 (2011); Bai et al., Proc. Natl. Acad. Sci. USA 102:7292-7296 (2005); Kim et al., J. Pharmacol. Exp. Ther., 334:682-692 (2010); Wang et al., J. Controlled Release 155:386-392 (2011)).

II.B.8. PEG

In certain aspects, a chimeric protein used in the methods of the present disclosure comprises at least one attachment site for a non-polypeptide heterologous moiety or fragment, variant, or derivative thereof. For example, a chimeric protein used in the methods of the present disclosure can include one or more polyethylene glycol (PEG) moieties attached to one or more amino acid residues in the clotting factor and/or the Fc region.

PEGylation of a protein can refer to a conjugate formed between the protein and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 Daltons. These average molecular weights are provided merely as examples and are not meant to be limiting in any way.

A chimeric protein used in the methods of the present disclosure can be PEGylated to include mono- or poly (e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., Exp. Hematol. 20:1028-35 (1992); Francis, Focus on Growth Factors 3 (2): 4-10 (1992); European Pat. Pub. Nos. EP0401384, EP0154316, and EP0401384; and International Pat. Appl. Pub. Nos. WO92/16221 and WO95/34326. As a non-limiting example, FVIII variants can contain cysteine substitutions, and the cysteines can be further conjugated to PEG polymer. See Mei et al., *Blood* 116:270-279 (2010) and U.S. Pat. No. 7,632,921, which are incorporated herein by reference in their entireties.

II.B.9. HES

In certain aspects, a chimeric protein used in the methods of the present disclosure comprises at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung Drug Res.* 41:494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

II.B.10. PSA

In certain aspects, a chimeric protein used in the methods of the present disclosure comprises at least one polysialic acid (PSA) polymer. PSAs are naturally occurring unbranched polymers of sialic acid produced by certain bacterial strains and in mammals in certain cells. See, e.g., Roth J. et al. (1993) in *Polysialic Acid: From Microbes to Man*, eds. Roth J., Rutishauser U., Troy F. A. (Birkhäuser Verlag, Basel, Switzerland), pp. 335-348. PSAs can be produced in various degrees of polymerization from n=about 80 or more sialic acid residues down to n=2 by limited acid hydrolysis or by digestion with neuraminidases, or by fractionation of the natural, bacterially derived forms of the polymer. There are a number of PSA attachment methods available to those skilled in the art, e.g., the same PEG attachment methods described above. In certain aspects, an activated PSA can also be attached to a cysteine amino acid residue within the clotting factor, e.g., on FVIII, or within the Fc region. See, e.g., U.S. Pat. No. 5,846,951.

II.B.11. Clearance Receptors

In certain aspects, the half-life of a chimeric protein used in the methods of the present disclosure can be extended where the clotting factor of the chimeric protein comprises FVIII and at least one fragment of a FVIII clearance receptor or FVIII-binding fragment, variant, or derivative thereof. Insertion of soluble forms of clearance receptors, such as the low density lipoprotein-related protein receptor LRP1, or fragments thereof, can block binding of FVIII to clearance receptors and thereby extend its half-life, e.g., in vivo half-life. LRP1 is a 600 kDa integral membrane protein that is implicated in the receptor-mediate clearance of a variety of proteins, including FVIII. See, e.g., Lenting et al., Haemophilia 16:6-16 (2010). Other suitable FVIII clearance receptors are, e.g., LDLR (low-density lipoprotein receptor), VLDLR (very low-density lipoprotein receptor), and megalin (LRP-2), or fragments thereof. See, e.g., Bovenschen et al., Blood 106:906-912 (2005); Bovenschen, Blood 116: 5439-5440 (2010); Martinelli et al., Blood 116:5688-5697 (2010).

III. Polynucleotides, Vectors, and Host Cells

In some aspects, the present disclosure provides a method of immune tolerance in a human, comprising administering to the human an effective amount of a polynucleotide or a set of polynucleotides encoding a clotting factor and/or a Fc region, e.g., encoding a chimeric protein comprising a clotting factor and an Fc region, wherein the human failed to respond to one or more previous immune tolerance therapy. In some embodiments, the polynucleotide or the set of polynucleotides is within an expression vector or a set of expression vectors. In certain embodiments, the expression vector or the set of expression vectors is within one or more host cells.

The polynucleotide encoding a clotting factor and/or a Fc region, e.g., encoding a chimeric protein comprising a clotting factor and an Fc region, used in the methods of the present disclosure can be a single nucleotide sequence, two nucleotide sequences, three nucleotide sequences, or more. In one embodiment, a single nucleotide sequence encodes a chimeric protein comprising a clotting factor (e.g., a FVIII polypeptide) and an Fc region. In another embodiment, the polynucleotide comprises two nucleotide sequences, the first nucleotide sequence encoding a clotting factor (e.g., a FVIII) and the second nucleotide sequence encoding an Fc region. In another embodiment, the polynucleotide comprises two nucleotide sequences, the first nucleotide sequence encoding a clotting factor (e.g., a FVIII) and an Fc region and the second nucleotide sequence encoding a second Fc region. In certain embodiments, the encoded Fc domains form a covalent bond after expression.

In some embodiments, the polynucleotide is codon-optimized.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for optimized expression of the chimeric proteins used in the methods of the present disclosure is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the instant invention are expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate for the production of the chimeric protein, and assayed for chimeric protein synthesis. Exemplary assay techniques include enzyme-linked immunosorbent assay (ELISA), radioimmunoassay (RIA), or flourescence-activated cell sorter analysis (FACS), immunohistochemistry, and the like.

Having now described the present invention in detail, the same will be more clearly understood by reference to the following examples, which are included herewith for purposes of illustration only and are not intended to be limiting of the invention.

EXAMPLES

Example 1

Hemophilia A ("factor VIII [FVIII] deficiency") is a rare bleeding disorder and the most common type of hemophilia. The most serious treatment complication for patients with hemophilia A is the development of inhibitory IgG antibodies to FVIII. Inhibitors result in rapid clearance of infused FVIII and marked reduction or absence of efficacy. FVIII inhibitor bypassing agents are used to treat acute bleeding in patients with inhibitors, but inhibitor eradication is the goal of long-term management.

Immune Tolerance Induction ("ITI") therapy using frequent administration of high doses of FVIII is the only strategy that has been shown to achieve antigen-specific tolerance. ITI is usually attempted to eliminate high-responding FVIII inhibitors (≥5BU titer). Several studies have investigated the efficacy of different FVIII products in achieving successful ITI with different doses and injection frequencies and international consensus recommendations have been issued to support ITI approaches in the clinical practice. In an International ITI Study, patients in the High Dose arm ("HD") (200 IU/Kg/day) achieved a negative titer and a normal recovery significantly more rapidly than patients in the Low Dose arm ("LD"). Hay and DiMichele, *Blood* 119 (6): 1335-44 (2012). HD patients also experienced significantly less bleeds than LD patients, and for this reason, the data safety monitoring board ("DSMB") recommended study termination because they identified bleeding as a safety issue. The high dose of 200 IU/Kg/day is the recommended dose in the "high-risk" patients (defined as those with peak historical titer >200BU, pre ITI titer >10 BU and/or >5 years since inhibitor diagnosis). There is increasing interest in the investigation of the use of the extended half-life ("EHL") rFVIIIFc in ITI. rFVIIIFc has been approved in the USA in 2014 with the name of ELOCTATE® and in Europe in 2015 with the name of ELOCTAR rFVIIIFc is produced in a human cell line ("HEK293") as a recombinant B-domain deleted ("BDD") factor VIII fused to the Fc domain of human IgG. HEK-produced proteins have similar post-translational modifications as native human proteins, in contrast to proteins produced in cell lines from other species, such as hamsters (e.g., CHO cells). In such proteins, non-human glycans (such as N-glycolylneuraminic acid, NGNA and galactose-alpha-1,3-galactose, allpha-Gal) resulting from the post-translational modifications can be potentially immunogenic. Neither NGNA, nor alpha-Gal is found in rFVIIIFc. Mice models have also shown that rFVIIIFc induces regulatory T cell responses to FVIII (See Batsuli Hemophilia (2016), 22 (Suppl. 5), 31-35), suggesting to some investigators that rFVIIIFc could provide more effective ITI, specifically shortening ITI, than rFVIII.

Objectives

The primary objective of the present study is to describe the time to tolerance with IFVIIIFc in patients after ITI treatment. The study also aims to describe the outcome of ITI treatment; to describe the relapse rate over a period of time after successful ITI performed with rFVIIIFc; to describe the intercurrent bleeding during ITI and during the period after successful ITI performed with rFVIIIFc; to describe safety and tolerability of rFVIIIFc when used for ITI; to describe specific quality of life (QoL) questions; and to demonstrate rFVIIIFc consumption.

Example 2

The present study aims to describe the use of rFVIIIFc for ITI in patients with severe heamophilia A with inhibitors who have failed previous ITI therapies. Specifically, primary objective of this study is to describe the outcome of ITI treatment performed with rFVIIIFc in patients who failed previous attempts of tolerization, including use of immunosuppressants, after ITI treatment. Secondary objectives and their endpoints include: (1) to describe time to tolerization of ITI performed with rFVIIIFc in patients who failed previous attempts of tolerization, including use of immunosuppressants, with an endpoint of time to ITI success; (2) to describe the relapse rate after successful ITI performed with rFVIIIFc, with an endpoint of occurrence of relapse; (3) to describe the intercurrent bleeding during ITI and during the period after successful ITI performed with rFVIIIFc, with an endpoint of bleeding rate; (4) to describe safety and tolerability of rFVIIIFc when used for ITI, with endpoints of adverse events and/or injection site reactions; and (5) to describe the consumption of rFVIIIFc in ITI performed with ELOCTA®, with an endpoint of rFVIIIFc.

Example 3

In this study, male subjects of all ages with severe hemophilia A and high titer inhibitors (historical peak ≥5 Bethesda Unit [BU]/mL) will receive recombinant coagulation factor VIII Fc fusion protein (rFVIIIFc) for undergoing first time immune tolerance induction (ITI) therapy, for eradicating and neutralizing anti-coagulation factor VIII (FVIII) alloantibodies.

Participants will receive rFVIIIFc at a dose of 200 international units (IU)/kilogram (kg) as once daily injections or divided on several injections per day at the discretion of the Investigator, starting at baseline visit up to maximum of 48 Weeks in ITI Period. Participants who meet the criteria for immune tolerance induction (ITI) success will enter the tapering period and will receive rFVIIIFc (as powder for injection administered Intravenously) at a dose adjusted according to Investigator judgment (50 or 100 IU/kg) once a day from Week 1 to 6 and every other day thereafter through Week 16.

The primary outcome measure of this study is to describe the time to tolerization with rFVIIIFc during a time frame of up to 12 months. Tolerization is defined as inhibitor titer <0.6BU/ml, FVIII recovery >66%, and $t_{1/2}$ of ≥7 hrs.

A secondary outcome measurement is the number of participants with immune tolerance induction (ITI) success. ITI Success will be defined as: negative titer for inhibitor less than (<) 0.6 BU/mL by the Nijmegen-modified Bethesda assay; FVIII incremental recovery (IR)>1.3 international units per deciliter (IU/dL) per IU/kg in 2 consecutive determinations representing 66% of the expected IR 2 IU/dL per IU/kg; half-life ($t_{1/2}$)≥7 hours. ITI success will be monitored over a time frame of up to 48 weeks.

Another secondary outcome measurement is the number of participants who experience relapse. The percentage of participants with ITI success that reach the criteria for relapse (defined as inhibitor titer >0.6 BU/mL or abnormal recovery after tolerance is achieved) will be evaluated. Relapse will be monitored over a time frame of up to 48 weeks.

Another secondary outcome measurement is the number of bleeding episodes. A bleeding episode started form the first sign of a bleed and ended no more than 72 hours after the last treatment for the bleed, within which any symptoms of bleeding at the same location or injections less than or equal to 72 hours apart, was considered the same bleeding episode. Bleeding episodes will be monitored over a time frame of up to week 104.

Another secondary outcome measurement is the number of participants with treatment-emergent adverse events (AEs) and treatment-emergent serious adverse events (SAEs). An AE is any untoward medical occurrence that does not necessarily have a causal relationship with this treatment. An SAE is any untoward medical occurrence that at any dose: results in death; in the view of the Investigator, places the participant at immediate risk of death (a life-threatening event); requires inpatient hospitalization or prolongation of existing hospitalization; results in persistent or significant disability/incapacity; results in a congenital anomaly/birth defect; any other medically important event that, in the opinion of the Investigator, may jeopardize the participant or may require intervention to prevent one of the other outcomes listed in the definition. AEs and SAEs will be measured for a time frame of about 2 years.

Another secondary outcome measurement is the number of days away from work or school. Number of days missed from school or work will be summarized descriptively, over a time frame of up to week 104.

Another secondary outcome measurement is the number of hospitalization days. The number of hospitalization days will be summarized descriptively and monitored over a time frame of up to week 104.

Another secondary outcome measurement is the adherence to treatment regimen, which is defined as percentage of administered doses versus planned doses, and which is monitored over a time frame of up to week 104.

Another secondary outcome measurement is consumption of rFVIIIFc. Consumption will be assessed based on amount of administered study treatment, and consumption will be monitored over a time frame of up to week 104.

The present study will be directed to male participants of any age diagnosed with severe hemophilia A (as confirmed from the medical record). Subject will have been diagnosed with high titer inhibitors (historical peak greater than or equal to (>) 5 biological units per milliliter (BU/mL), according to medical records), and subjects will have been previously treated with any plasma-derived or recombinant conventional or extended half-life FVIII. Exclusion criteria includes subjects that have any other coagulation disorder(s) in addition to hemophilia A; any previous ITI therapy; a history of hypersensitivity or anaphylaxis associated with any recombinant coagulation factor VIII Fc (rFVIIIFc) administration; any abnormal renal function (serum creatinine greater than 2.0 milligrams per deciliter [mg/dL]) as assessed by local laboratory; and/or serum alanine aminotransferase or aspartate aminotransferase >5×upper limit of normal (ULN) as assessed by local laboratory.

Example 4

A noninterventional retrospective chart review of ITI with rFVIIIFc in patients with severe haemophilia A and high-titre inhibitors (HTI; ≥5 BU) was conducted across 10 sites in the United States and Canada between Jul. 1, 2014, and Jun. 1, 2017. Male patients of all ages with severe haemophilia A with HTI who had initiated treatment with rFVIIIFc for ITI, either as primary or rescue therapy, regardless of response, were included.

After institutional regulatory approval, de-identified clinical information was collected via an electronic survey. Patients treated for the first time with ITI were considered at high risk for ITI failure according to the criteria listed earlier. Negative Bethesda titre was defined as ≤0.6 BU. Tolerization was defined as negative Bethesda titre and normal FVIII recovery (≥66%) and half-life (≥6 hours). The primary objective of this study was to report the clinical characteristics and outcomes of ITI using rFVIIIFc. Results are summarized using descriptive statistics; no inferential statistical analysis was conducted.

Results

Study Population

Nineteen patients were identified. Of these, seven were receiving ITI for the first time and 12 were undergoing rescue ITI (Tables 1 and 2). Median age at initiation of rFVIIIFc ITI was 1.3 years (range: 0.8-4.3 years) for first-time ITI and 6.4 years (range: 1.6-12.6 years) for rescue ITI patients.

First-time ITI patients had a median peak historical inhibitor (pre-ITI) titre of 151 BU (range: 11-1126 BU); the median inhibitor titre at start of rFVIIIFc ITI was 52 BU (range: 3-1126 BU). At the start of ITI, six of seven first-time ITI patients had titres >10 BU; four of these six had titres >50 BU. The median time from inhibitor diagnosis to start of rFVIIIFc ITI was 4.4 weeks (range: 0-41 weeks).

For rescue ITI patients, the mean number of prior ITI courses with other FVIII products was 2.6 (range: 1-5) and the median time from inhibitor diagnosis to the start of rFVIIIFc ITI was 5.5 years (range: 0.8-12 years). FVIII genotypes for 18 of the 19 patients are shown in Tables 1 and 2.

First-Time ITI Patient Outcomes

At the time of data collection, four of seven patients undergoing first-time ITI (Table 1) were tolerized and had transitioned to prophylaxis with rFVIIIFc. Three of these four patients achieved a negative Bethesda titre and normal FVIII recovery and half-life; as such, they met the standard definition of tolerization at 5, 7, and 9 months. The fourth patient was considered tolerized by the treating physician at 14.8 months based on a negative inhibitor titre and having been transitioned to prophylaxis; at the time of data collection that patient was 13 months post completion of rFVIIIFc ITI and he continued to have a negative inhibitor on rFVIIIFc prophylaxis. A normal half-life was also reported at that time.

TABLE 1

Patients receiving ITI for the first time.

| Patient | Genotype | Historical peak inhibitor titer (BU/mL) | Inhibitor titer pre-rFVIIIFc ITI (BU/mL) | Time from positive Bethesda titer to start of ITI (weeks) | rFVIIIFc ITI regimen | Current titer (BU/mL) | Time to negative Bethesda titer (weeks) | Time to Tolerization (weeks) | Current status |
|---|---|---|---|---|---|---|---|---|---|
| 1 | missense | 51.7 | 51.7 | 10.9 | 85 IU/kg daily | <0.6 | 4 | 21 | rFVIIIFc Prophylaxis |
| 2 | Frameshift | 150.9 | 106.9 | 13.0 | 100 IU/Kg daily | <0.6 | 24 | 29 | rFVIIIFc Prophylaxis |
| 3 | NR | 1126 | 1126 | 1.1 | 200 IU/kg daily | <0.6 | 31 | 38 | rFVIIIFc Prophylaxis |
| 4 | I-22 | 11 | 11 | 4.4 | 50 IU/kg 3x/wk | <0.6 | 64 | 64 | rFVIIIFc Prophylaxis |
| 5 | I-22 | 388 | 32 | 41.0 | 102 IU/kg EOD | 18 | NA | N/A | rFVIIIFc ITI |
| 6 | I-22 | 378.7 | 378.1 | 1.0 | 96 IU/kg daily | 23 | NA | N/A | rFVIIIFc ITI |
| 7[a] | I-22 | 30 | 3 | 0.0 | 83 IU/kg daily | 16 | NA | N/A | rFVIIIFc ITI |

BU, Bethesda units; EOD, every other day; I-22, intron 22 inversion; ITI, immune tolerance induction; NR, not reported; N/A, not applicable; rFVIIIFc, recombinant factor VIII Fc fusion protein. Time to tolerization based on physician report, resolved Bethesda titer, normal recovery and half-life. Patient 4 did not have recovery and half-life information available but was reported as tolerized by physician and switched to rFVIIIFc prophylaxis.
[a]Received rituximab.

Among the four patients, the median time to attain a negative Bethesda titre was 27.7 weeks (range: 4.1-64 weeks). The ITI regimen for three of the four tolerized patients consisted of daily rFVIIIFc (85-200 IU/kg) compared with three-times-per-week dosing (50 IU/kg) for the fourth patient (Table 1). Median time to reported tolerization was 33.9 weeks (7.8 months; range: 21-64 weeks) for all four patients. For the three patients treated with daily rFVIIIFc (85-200 IU/kg), tolerization took 29 weeks (6.7 months; range: 20.6-38 weeks), however the fourth patient treated with 50 IU/kg three times per week tolerized in 64 weeks (14.8 months).

Of the remaining patients (n=3), two had a decrease in Bethesda titre (from 32 to 18 BU and 378 to 23 BU after 18 and 58 weeks of ITI, respectively). At the time of this review, one patient had an increase in Bethesda titre (from 3 to 16 BU after 15 weeks of ITI); this patient has been on and off ITI and has had rFVIIIFc interruptions and poor compliance per treating physician report (Table 1). All seven first-time ITI patients continue on rFVIIIFc ITI or prophylaxis.

Rescue ITI Patient Outcomes

Seven of 12 patients undergoing rescue ITI (Table 2) initially achieved Bethesda negativity with rFVIIIFc ITI. Median time to attain a negative titre was 14.1 weeks (range: 3-67.6 weeks). Three of these seven patients remain Bethesda negative and continue on rFVIIIFc ITI or rFVIIIFc wean to prophylaxis. The other four patients who initially achieved a negative titre later developed a titre >0.6 BU. Of these, two continue on rFVIIIFc ITI and two were transitioned to ITI with other factors (Table 2).

concurrently with rFVIIIFc ITI; fourteen were primarily on prophylaxis (9 with aPCCs and 5 with rFVIIa) and four were treated on demand with rFVIIa.

Overall, 16 of 19 patients remained on rFVIIIFc (prophylaxis or ITI) at the time of data collection (Tables 1 and 2).

Safety

No adverse events, including no thromboembolisms, were reported. Six surgeries were performed, all of them without interruption of rFVIIIFc ITI (knee synovectomy, intracranial neurosurgical evacuation, and four Port-A-Cath replacements). Bypass therapy was used in all. Inhibitor titres during surgeries were not collected for this study.

TABLE 2

Patients receiving rescue ITI.

| Patient | Geno-type | Number of prior ITI treatments | Historical peak inhibitor titer (BU/mL) | Inhibitor titer before rFVIIIFc ITI (BU/mL) | rFVIIIFc ITI regimen | Current titer (BU/mL) | Time to negative Bethesda titer[b] (weeks) | Current status |
|---|---|---|---|---|---|---|---|---|
| 8 | I-22 | 5 | 250 | 9 | 202 IU/kg daily | <0.6 | 28 | rFVIIIFc ITI wean |
| 9 | I-22 | 2 | 67 | 4 | 150 IU/kg daily | <0.6 | 3 | Other ITI |
| 10 | Large deletion | 2 | 70 | 35 | 200 IU/kg EOD | <0.6 | 31 | rFVIIIFc ITI |
| 11 | I-22 | 1 | 178 | 1 | 100 IU/kg 3x/wk | <0.6 | 14 | rFVIIIFc ITI |
| 12[a] | I-22 | 2 | 460 | 200 | 150 IU/kg daily | 2 | 13 | Other ITI |
| 13 | I-22 | 3 | 41.8 | 22 | 130 IU/kg daily | 16 | 68 | rFVIIIFc ITI |
| 14[a] | Non-sense | 2 | 306 | 129 | 100 IU/kg daily | 23 | 13 | rFVIIIFc ITI |
| 15 | I-22 | 1 | 35 | 36 | 200 IU/kg EOD | 22 | NA | rFVIIIFc ITI |
| 16 | I-22 | 3 | 11 | 1 | 100 IU/kg EOD | 0.9 | NA | rFVIIIFc ITI |
| 17 | I-22 | 2 | 8 | 0.6 | 115 IU/kg EOD | 1.2 | NA | rFVIIIFc ITI |
| 18 | Large deletion | 4 | 1024 | 237 | 100 IU/kg daily | 1024 | NA | rFVIIIFc ITI |
| 19 | Non-sense | 4 | 409 | 26 | 100 IU/kg daily | 166 | NA | Bypass therapy |

BU, Bethesda units; EOD, every other day; I-22, intron 22 inversion; ITI, immune tolerance induction; rFVIIIFc, recombinant factor VIII Fc fusion protein; wk, week.
[a]Received rituximab;
[b]Time to negative Bethesda titer represents time from start of rFVIIIFc ITI to first report of negative titer; current titer >0.6 BU/mL may represent recurrence.

Of the seven patients achieving Bethesda negativity, three also achieved normal FVIII recovery at 3, 14, and 65 weeks and a fourth patient reached normal FVIII half-life at 27 weeks. Recovery and half-life were not available in others (Table 2). Of the remaining five patients, one had a decrease in Bethesda titre (from 36 to 22 BU after 10 weeks) and four had the Bethesda titre either remain unchanged or increased while on ITI (Table 2). Of these five patients, four continue on rFVIIIFc ITI and one was removed from ITI and placed on bypass therapy alone.

Dosing Outcomes, Bypass Agent Use, and Current Treatment Status

The patient population assessed in this study received a wide range/timing of doses (Tables 1 and 2). A trend toward rapid negative inhibitor titres was seen with higher doses administered daily. Five of five patients (one first-time ITI and four rescue ITI) who received a daily rFVIIIFc dose of ≥130 IU/kg achieved a negative Bethesda titre at a median of 28 weeks. Eighteen of 19 patients used bypass agents Conclusions Collectively, these results show that ITI with rFVIIIFc is possible and can result in inhibitor eradication and successful ITI in many (high risk for ITI failure) patients undergoing first-time ITI and in some patients undergoing rescue ITI. Furthermore, FFVIIIFc ITI demonstrated a rapid decrease in Bethesda titres and rapid time to tolerization in the majority of patients receiving first-time ITI despite their risk profile. For rescue ITI, it is more difficult to make conclusions as most of these patients were still undergoing ITI with rFVIIIFc at the time of data collection. However, some patients receiving rescue treatment did appear to derive therapeutic benefit in that they either achieved Bethesda negativity or showed significant drops in inhibitor titres. This was particularly the case when higher rFVIIIFc dosing (≥130 IU/kg) was administered daily.

Example 5

The main complication of replacement therapy with factor in hemophilia A is the formation of inhibitors (neutralizing anti-factor VIII antibodies) in ~30% of patients with severe hemophilia A. Inhibitor development impacts treatment efficacy as well as the quality of life of affected individuals. Further understanding of how the immune system responds to recombinant factor III (rFVIII) is an ongoing effort in hemophilia research to effectively eradicate inhibitors. The extended half-life rFVIII Fc fusion protein (rFVIIIFc) is an efficacious and well-tolerated therapy to prevent and control bleeding episodes. The Fc region of this molecule is not only responsible for increasing rFVIII half-life but may promote antigen-specific tolerance, as shown in a preclinical animal model (Krishnamoorthy S, et al., *Cell Immunol.* 301:30-39 (2016)) and as suggested by immune tolerance induction case reports (Groomes C L, et al., *Pediatr Blood Cancer* 63 (5): 922-24 (2016); Malec L M, et al., *Haemophilia* 22 (6): e552-e554 (2016); Ragni M V, et al., *Haemophilia* 22 (5): e462-e464 (2016)).

Methods

Peripheral blood-derived human APCs or THP-1 monocytic cells were used to investigate the effects of rFVIIIFc on FcγR binding, internalization, signaling and cytokine production, and gene expression changes, as well as subsequent interactions and effects on T cells in vitro (FIG. 1).

Figure 2A:
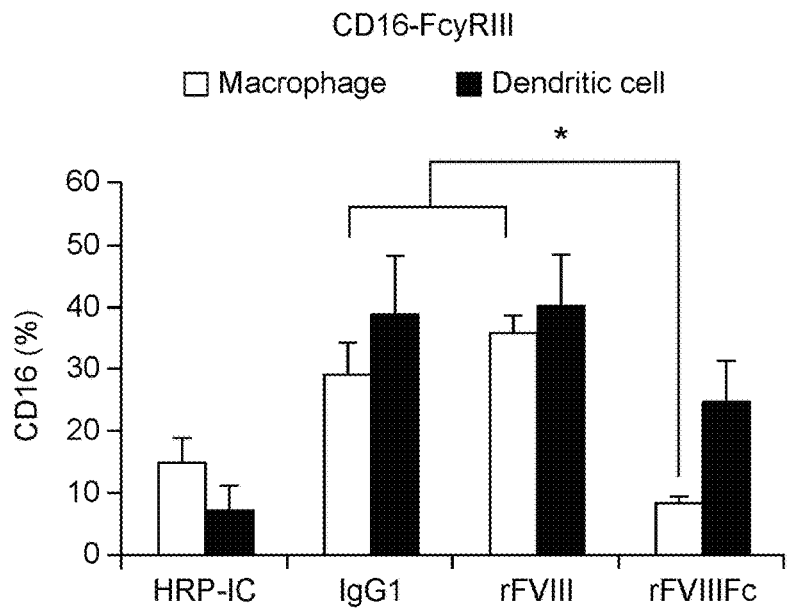
FIGS. 2A-2C are graphical representations of the relative macrophage and dendritic cell surface expression levels of the Fcγ receptors CD16 (FIG. 2A), CD32 (FIG. 2B), and CD64 (FIG. 2C) following treatment with horseradish peroxidase immune complexes (HRP-IC; positive control), IgG1, recombinant FVIII (rFVIII), or a rFVIII Fc fusion protein (rFVIIIFc). Asterisks (*) indicate degree of significance (n=3; =P≤0.01, *=P≤0.005, significance for HRP-IC as compared with the other treatments is not shown).
Figure 2B:
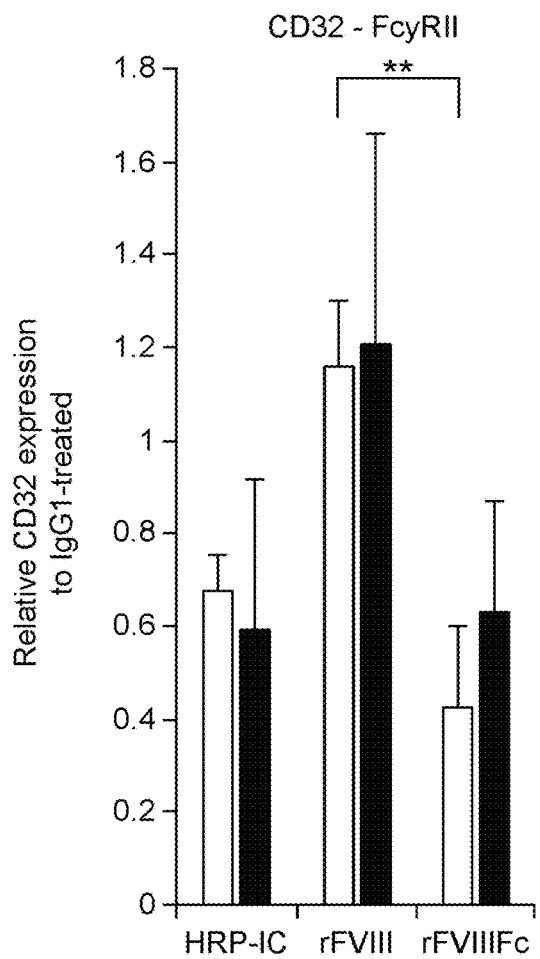
Figure 2C:
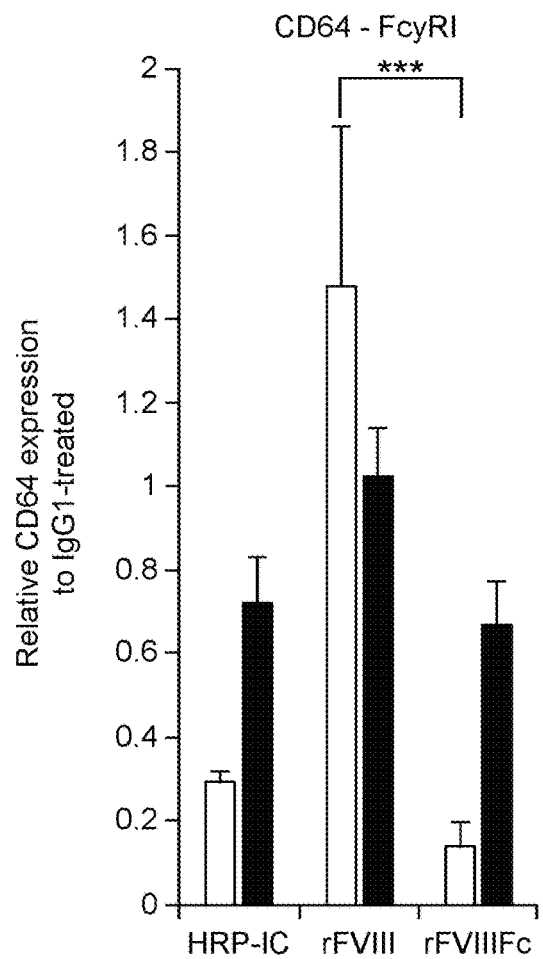
Figure 3A:
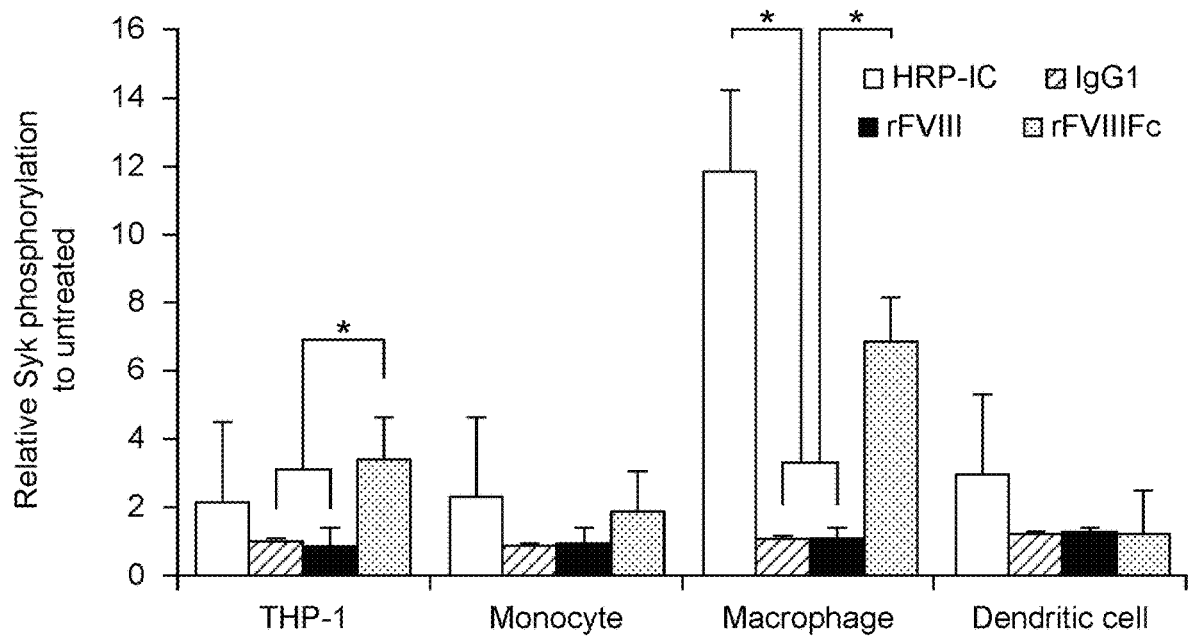
FIGS. 3A-3C are graphical representations illustrating relative signaling following treatment with rFVIII or FFVIIIFc.
Figure 3B:
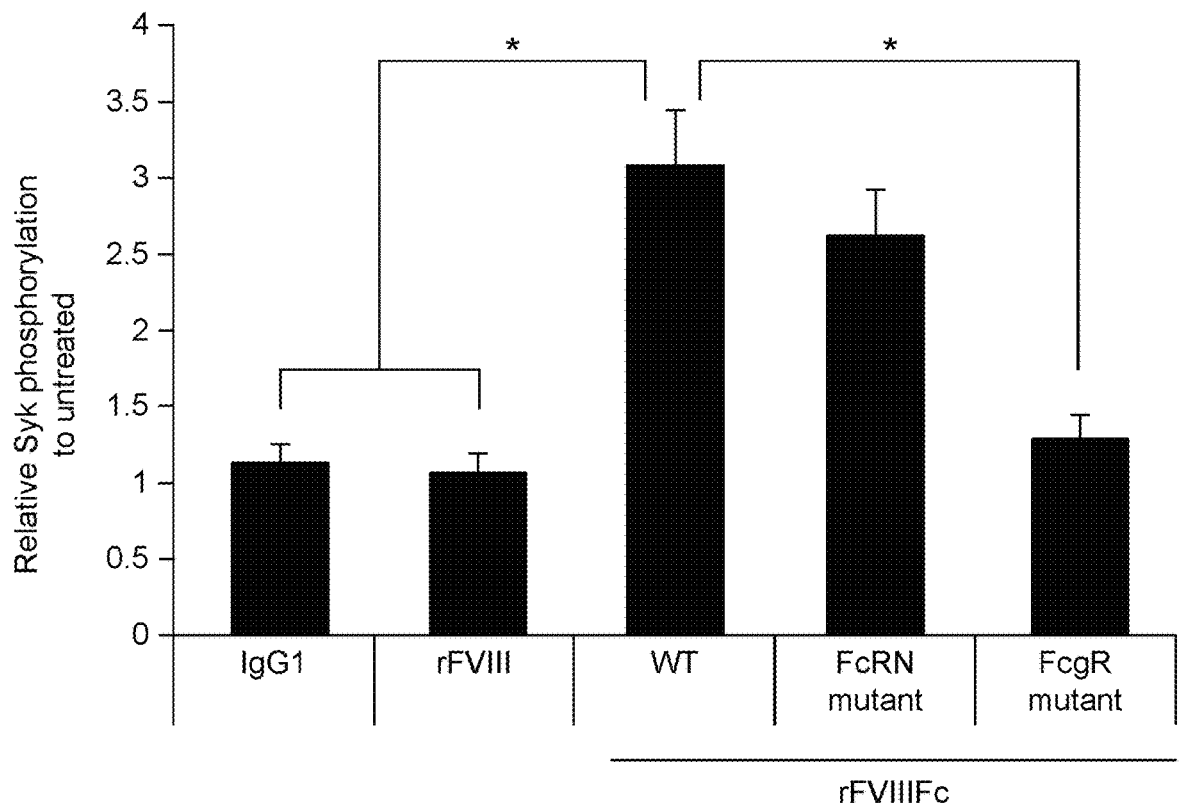
Figure 3C:
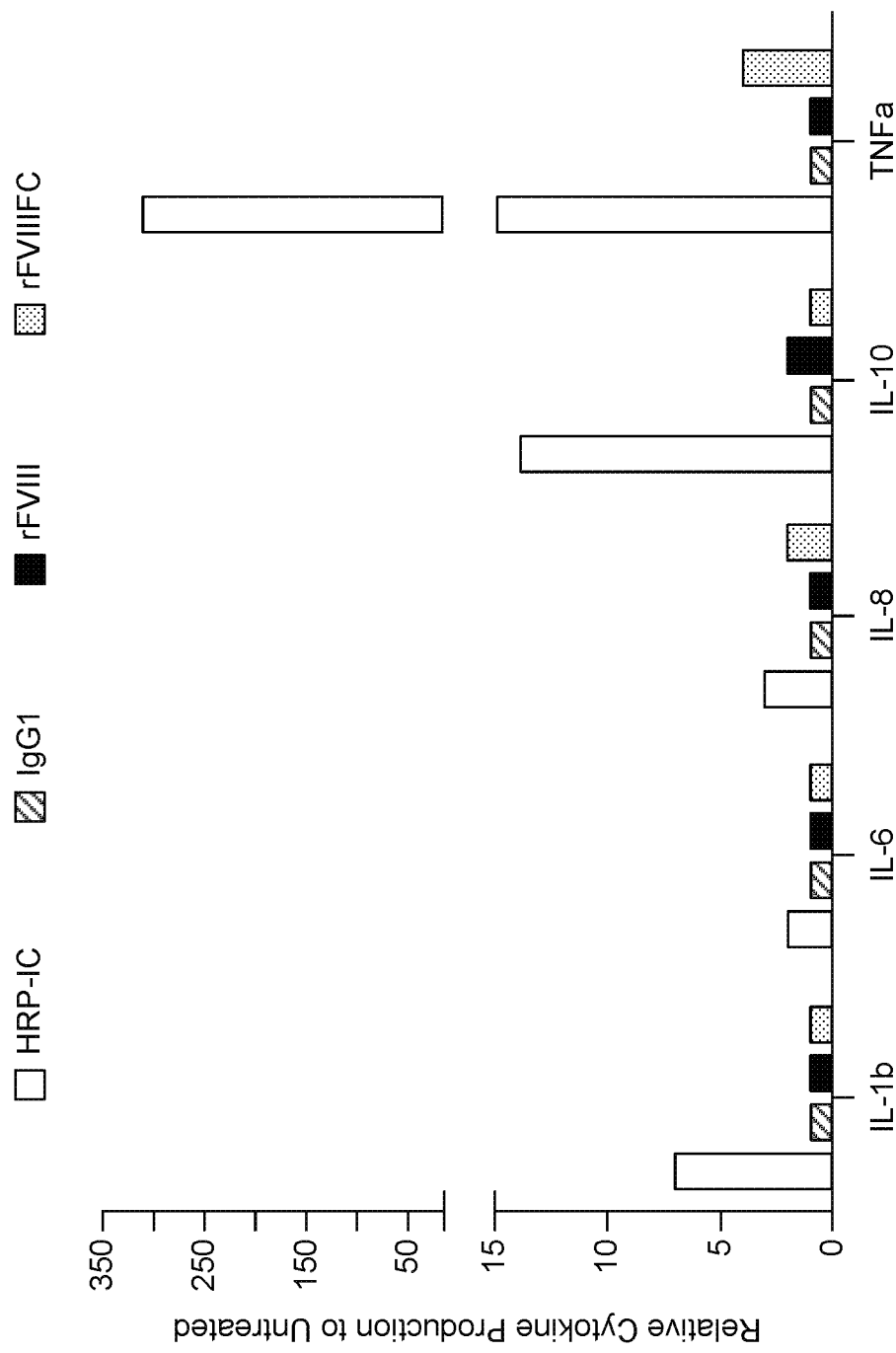
Figure 4:
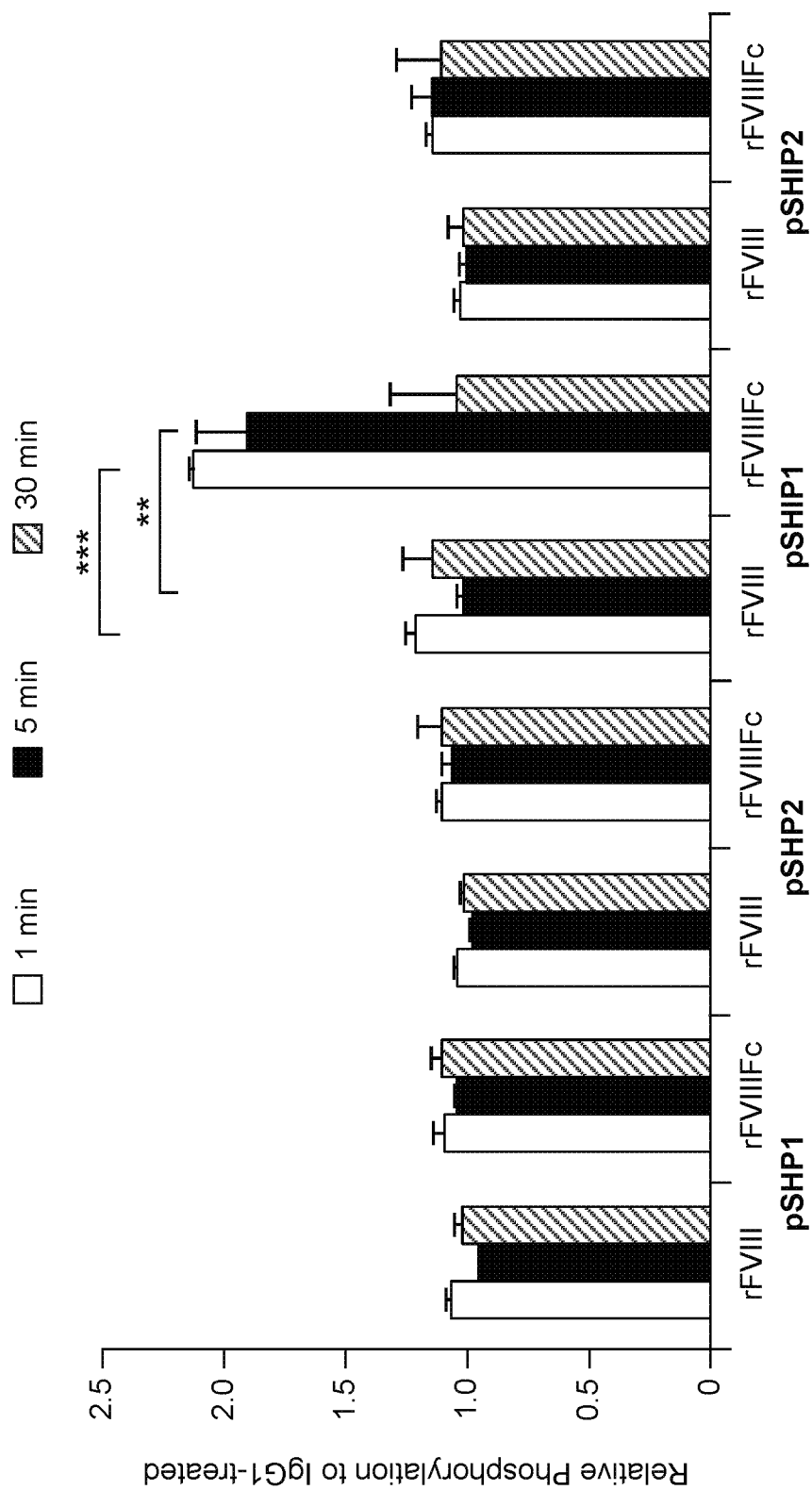
FIG. 4 shows the relative phosphorylation status of Src homology region 2 domain-containing phosphatase-1 (SHP1), pSHP2, phosphatidylinositol-3,4,5-trisphosphate 5-phosphatase 1 (SHIP1), and pSHIP2 one minute, five minutes, and thirty minutes after treatment with rFVIII or rFVIIIFc. Asterisks (*) indicate degree of significance (n=3; P≤0.01, *P≤0.005).

Results Decreased cell surface expression of FcγR indicates internalization upon rFVIIIFc treatment (FIGS. 2A-2C). Monocyte-derived macrophages and dendritic cells were treated with horseradish peroxidase immune complexes (HRP-IC) as positive control, human immunoglobulin G1 (IgG1) as negative control, and with recombinant factor VIII (rFVIII) or rFVIII Fc fusion protein (rFVIIIFc) at equimolar concentrations (200 nM) for 24 hours. The cell surface expression of the Fcγ receptors (FcγR) CD16 (FIG. 2A), CD32 (FIG. 2B), and CD64 (FIG. 2C) was measured by flow cytometry (n=3; $P \leq 0.01$, *$P \leq 0.005$, significance for HRP-IC to other treatments not shown). Treatment with rFVIIIFc correlated with decreased cell surface expression of CD16 (FIG. 2A), CD32 (FIG. 2B), and CD64 (FIG. 2C), as compared to surface expression following treatment with rFVIII.

rFVIIIFc engages FcγR and induces signaling in monocytes and macrophages, without subsequent proinflammatory cytokine production (FIGS. 3A-3C). THP-1 monocytic cell line, monocytes, peripheral blood monocyte-derived macrophages, and peripheral blood monocyte-derived dendritic cells were treated with HRP-IC, IgG1, FFVIII or FFVIIIFc for 15 minutes (FIG. 3A). Syk phosphorylation was measured in cell lysates using the MSD platform (n=3-7, *$P<0.05$). Syk phosphorylation was measured after treating macrophages with rFVIIIFc (WT), with mutant rFVIIIFc that is unable to bind to neonatal Fc receptor (FcRn mutant), or with mutant rFVIIIFc that is unable to bind to FcγR (FcγR mutant) (n=4, *$P<0.05$) (FIG. 3B). Proinflammatory cytokine production of the twenty-four-hour treated macrophages were measured by MSD ELISA (n=4, significance not shown) (FIG. 3C).

rFVIIIFc phosphorylates molecules taking part in immunoregulation, rather than molecules playing role in activation and proinflammatory cytokine production (Table 3 and FIG. 4). Phosphorylated proteins in lysates from monocyte-derived macrophages treated with IFVIIIFc for fifteen minutes were queried using the Proteome Profiler phosphokinase and phospho-immunoreceptor arrays. A list of phosphorylated molecules in rFVIIIFc-treated macrophages identified by the Proteome Profiler assays is shown in Table 3. Phosphorylation of phosphatases responsible for inhibitory signaling were measured using the MSD platform (n=3; $P \leq 0.01$, *$P \leq 0.005$) (FIG. 4).

TABLE 3

Phosphorylated molecules in rFVIIIFc-treated macrophages identified by a Proteome Profiler assays.
Phosphorylated Proteins

Figure 5A:
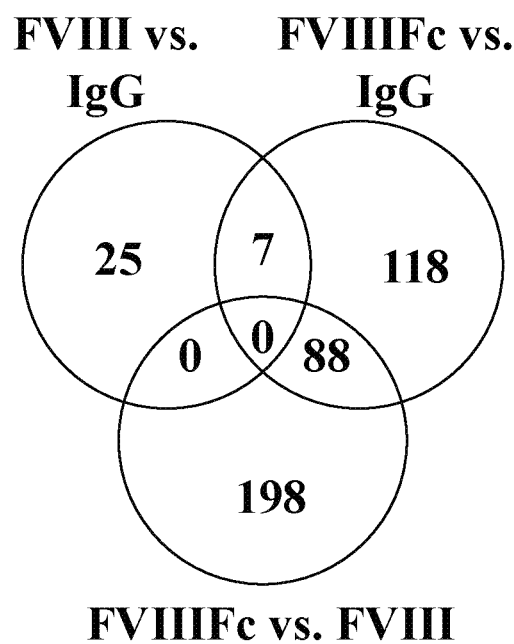
FIGS. 5A-5M are graphical representations of gene expression patterns of tolerogenic macrophages following treatment with rFVIII or FFVIIIFc.
Figure 5B:
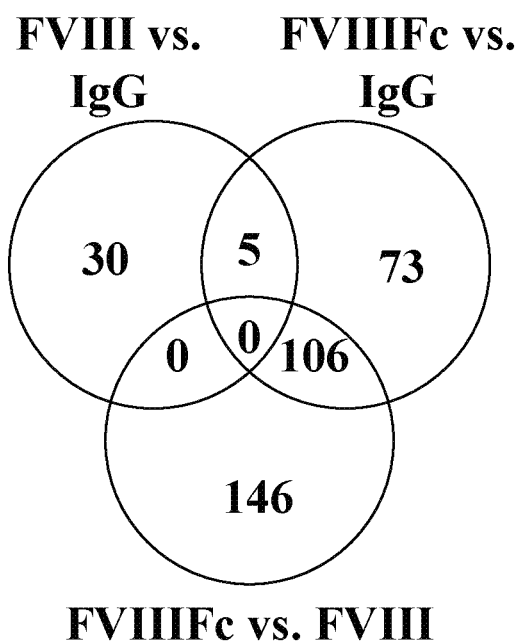
Figure 5C:
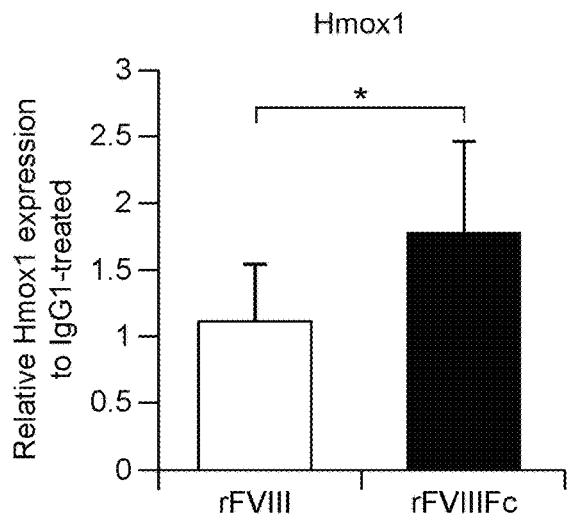
Figure 5D:
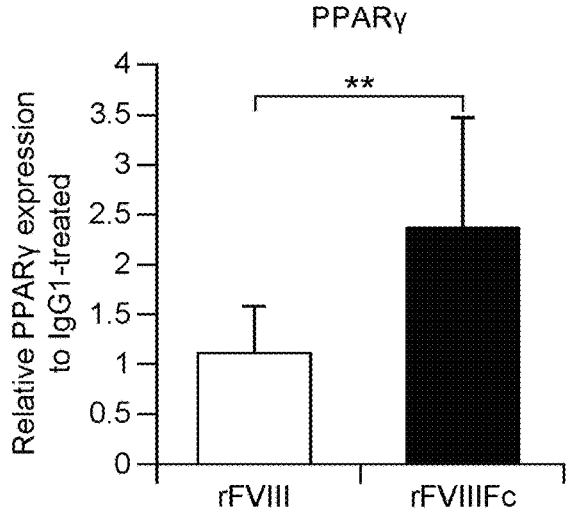
Figure 5E:
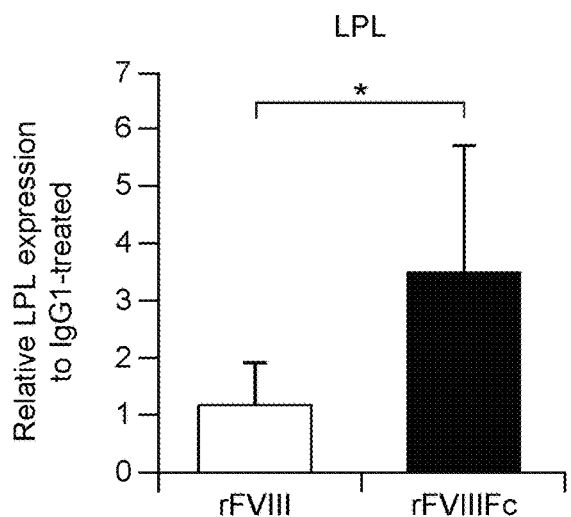
Figure 5F:
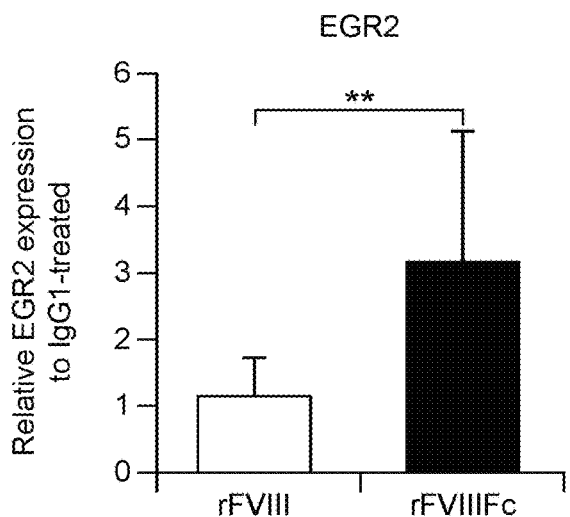
Figure 5G:
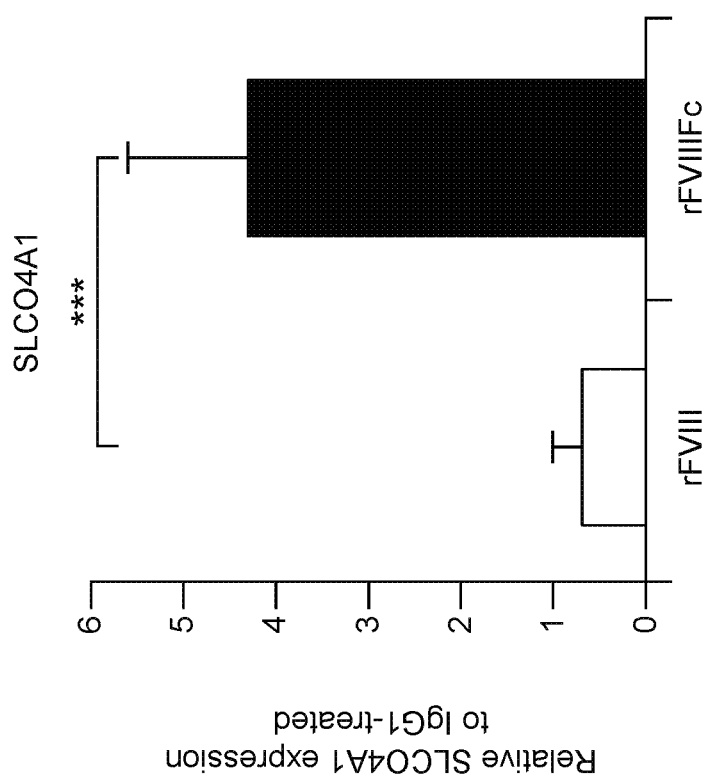
Figure 5H:
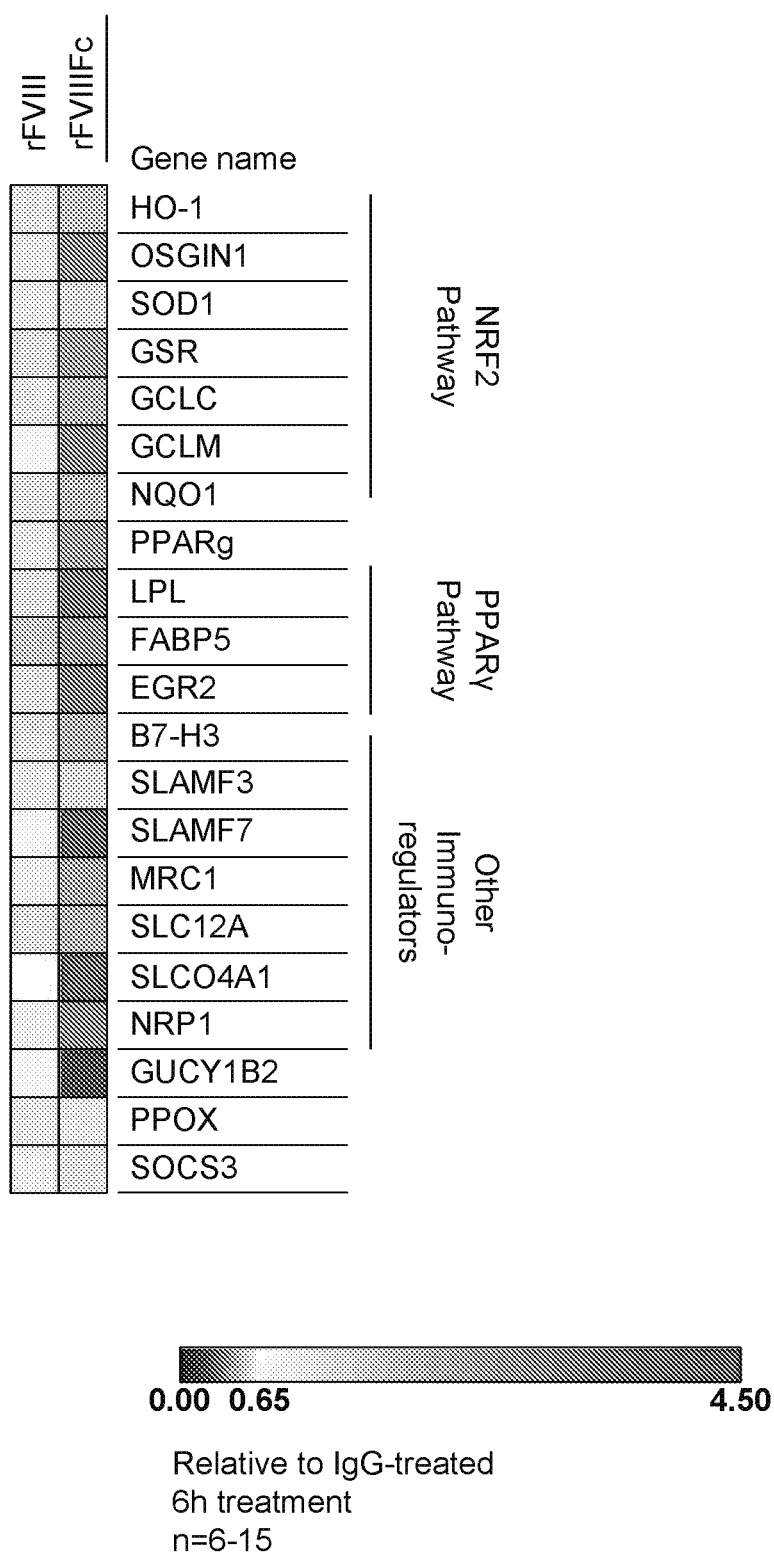
Figure 5I:
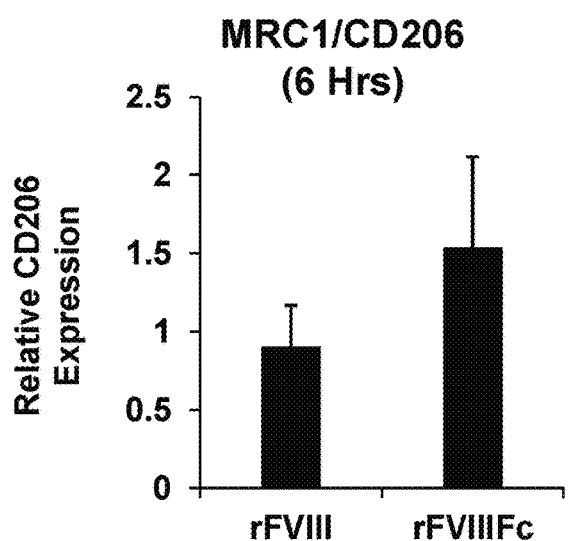
Figure 5J:
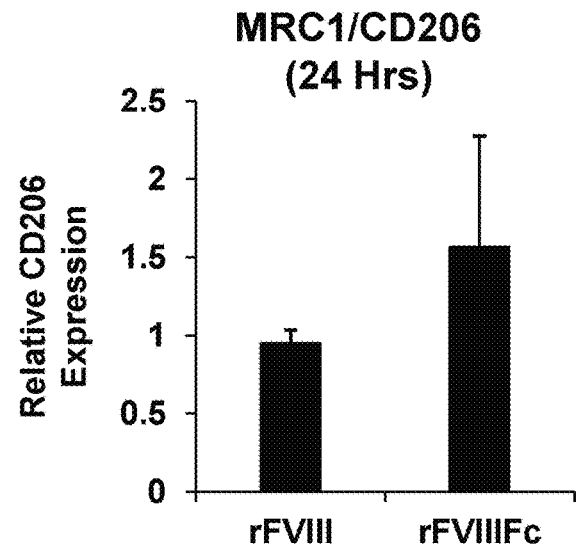
Figure 5K:
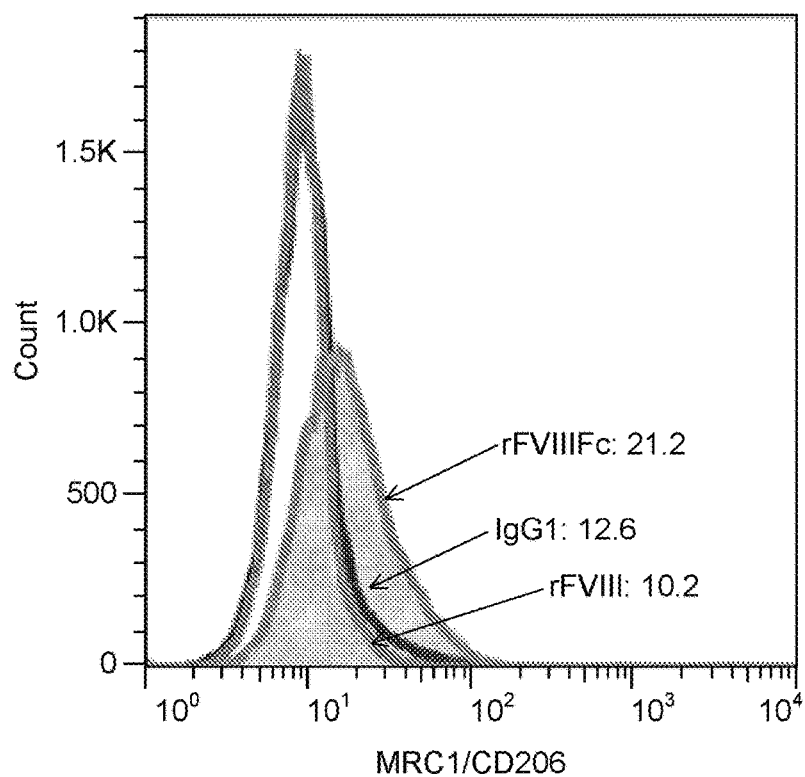
Figure 5L:
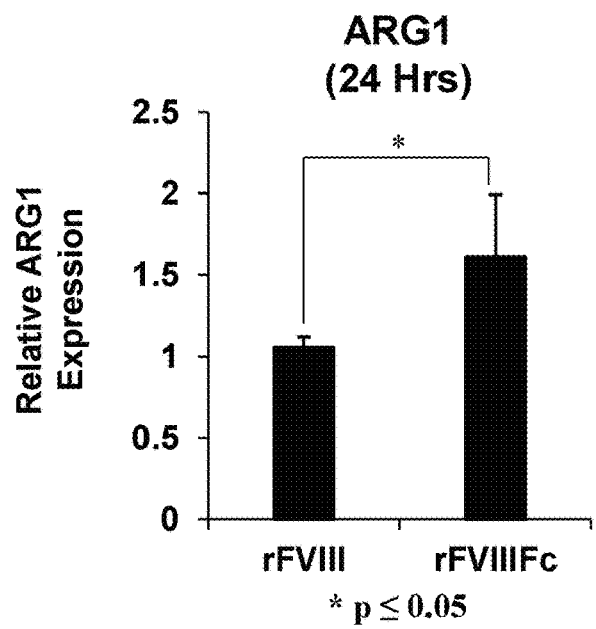
Figure 5M:
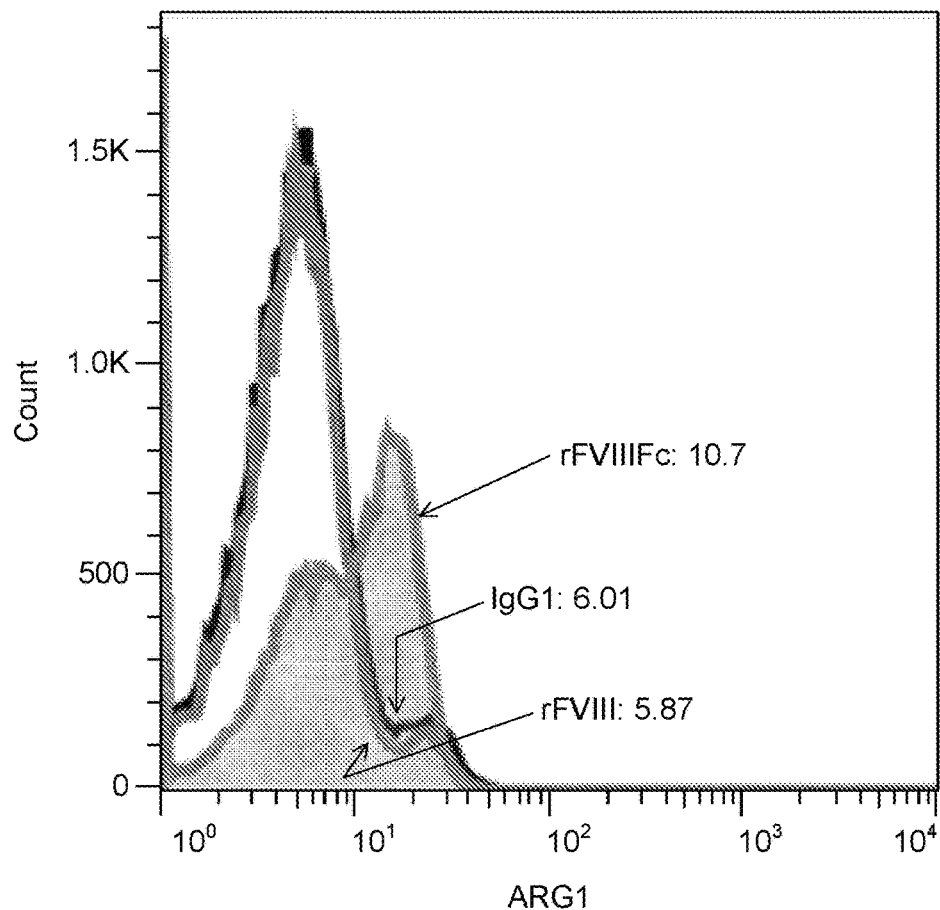

| Immunoreceptors | ILT6/CD85e | NKp46/NCR1 | FcH5/IRTA2 | Kinases | SRC | STAT5 |
|---|---|---|---|---|---|---|
| | KIR2DL4 | Siglec9 | Siglec2/CD22 | | CREB | cJun |
| | SLAMF8 | SLAMF4 | CDCIR/CLEC4α | | pRAS40 | p53 |
| | FcγRIIIA/B | FcγRIIA | DECTIN-1/CLEC7α | | ERK1/2 | WNK1 |
| | PECAM/CD31 | FcRH4/IRTA1 | KNKp44/NCR2 | | HSP27 | p70S6 |
| | CLEC-2 | SHP2 | Siglec7 | | JNK1/2/3 | FAK |
| | TREM2 | ILT2/CD85j | SLAMF5 | | AMPKα2 | GSK-3α/β |
| | SHP1 | ILT3/CD85k | Siglec3/CD33 | | STAT2 | RSK1/2/3 |
| | TREML1/TLT-1 | ILT4/CD85d | Siglec5 | | STAT6 | p53 | rFVIIIFc induces gene expression pattern characteristic of tolerogenic macrophages (FIGS. 5A-5G). Exploratory RNA sequencing was performed on monocyte-derived macrophages treated with IgG1, FFVIII, or FFVIIIFc for six hours (n=3) for genes that were significantly downregulated (FIG. 5A) and for genes that were significantly upregulated (FIG. 5B), and a pathway analysis was run on the rFVIIIFc-upregulated genes to investigate the molecular pathways represented selectively in these cells, compared to rFVIII-treated cells (Table 4). Various genes of the NRF2 and PPAR-gamma pathways were found to be upregulated, as well as various other immunoregulators (FIG. 5H). Selected genes of the NRF2 and lipid metabolism pathways were validated by Q-PCR (n=8; *$P \leq 0.05$, $P \leq 0.01$, *$P \leq 0.005$) (FIGS. 5C-5G). In addition, rFVIIIFc-educated macrophages were found to exhibit a characteristic M2-like phenotype (FIGS. 5I-5M). In particular, macrophages treated with rFVIIIFc had higher relative CD206 expression than cells treated with rFVIII after 6 hours (FIG. 5I) and after 24 hours (FIG. 5J), and macrophages treated with rFVIIIFc had higher relative ARG1 expression than cells treated with rFVIII after 24 hours (FIG. 5M).

TABLE 4

Run pathway analysis on the rFVIIIFc-upregulated genes to investigate the molecular pathways represented selectively in these cells, compared to rFVIII-treated cells.

| Pathway Name | Set Size | Candidates Contained | P-value | q-value |
|---|---|---|---|---|
| NRF2 pathway | 142 | 10 (7.0%) | 4.07e−06 | 0.000273 |
| Liproprotein metabolism | 68 | 7 (10.3%) | 1.01e−05 | 0.000338 |
| Lipid digestion, mobilization, and transport | 110 | 8 (7.3%) | 3.06e−05 | 0.000684 |

TABLE 4-continued

Run pathway analysis on the rFVIIIFc-upregulated genes to investigate the molecular pathways represented selectively in these cells, compared to rFVIII-treated cells.

Figure 6A:
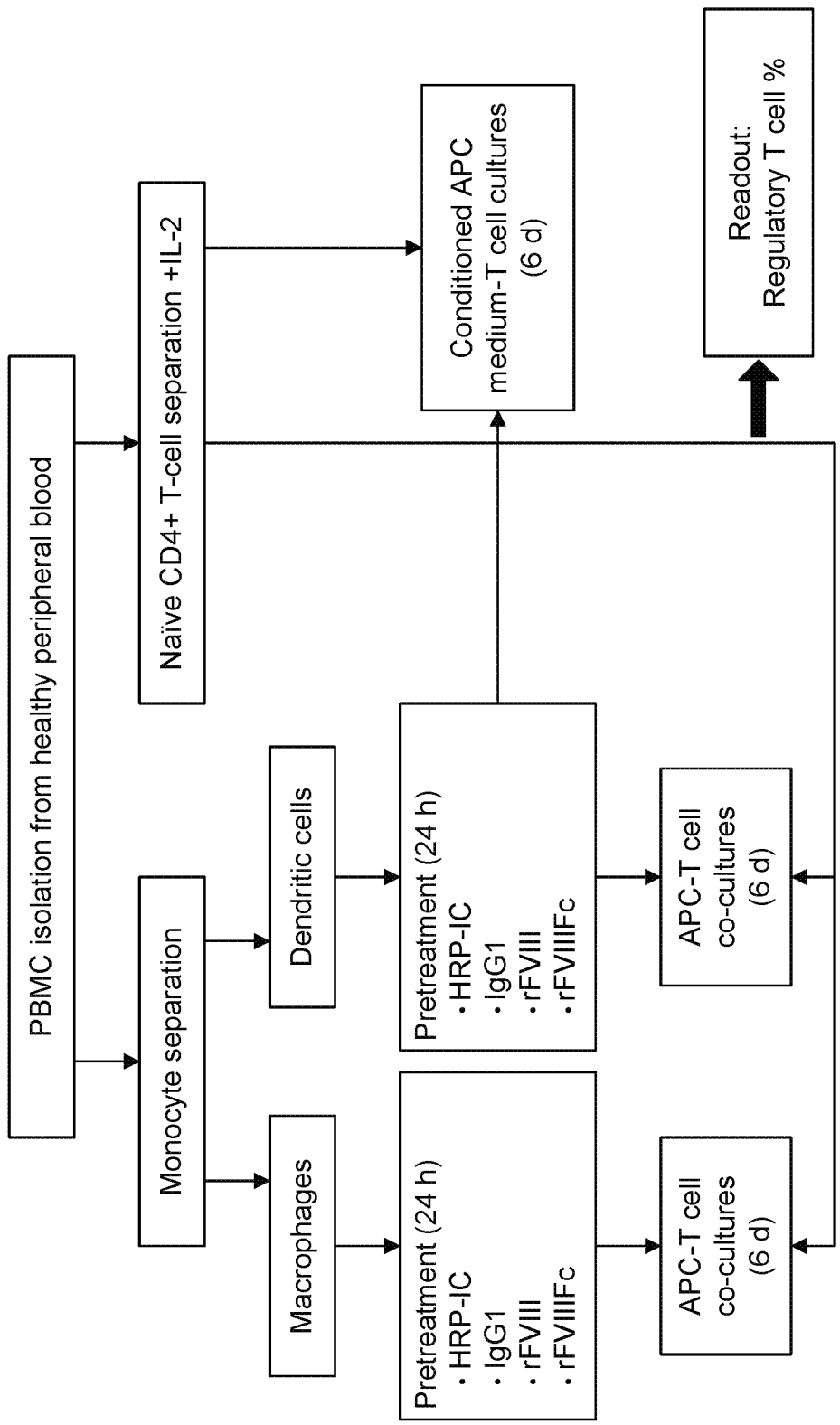
FIG. 6A is a flow chart diagraming the methods used to determine the effects of rFVIIIFc treatment on T-cell differentiation.
Figure 6B:
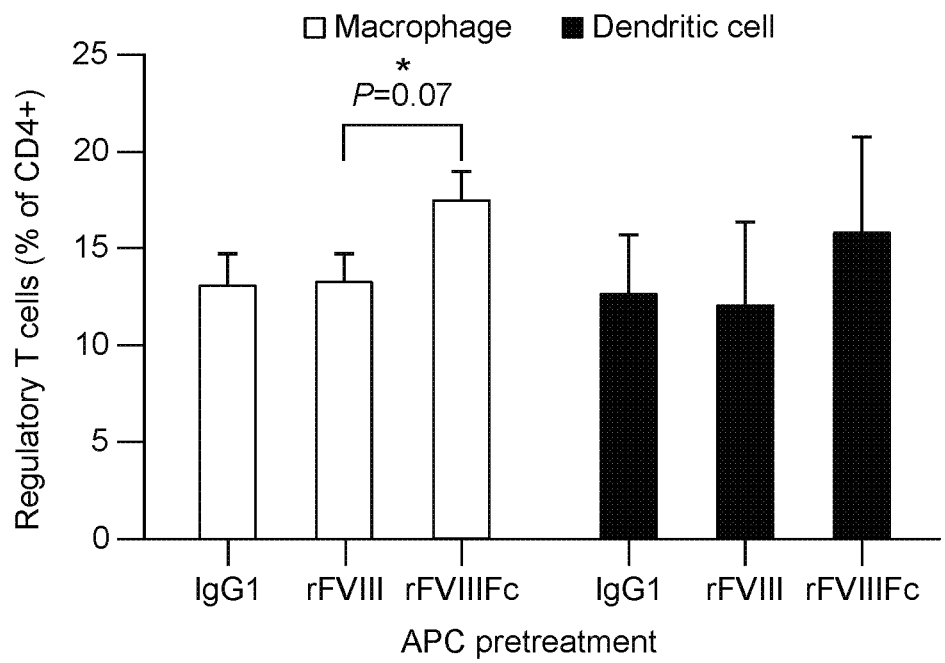
FIG. 6B is a graphical representation of the percent of regulatory T cells six days after macrophages or dendritic cells were treated with IgG1 (control), IFVIII, or FFVIIIFc for 24 hours, and then placed into co-culture with naïve CD4 positive T cells.
Figure 6C:
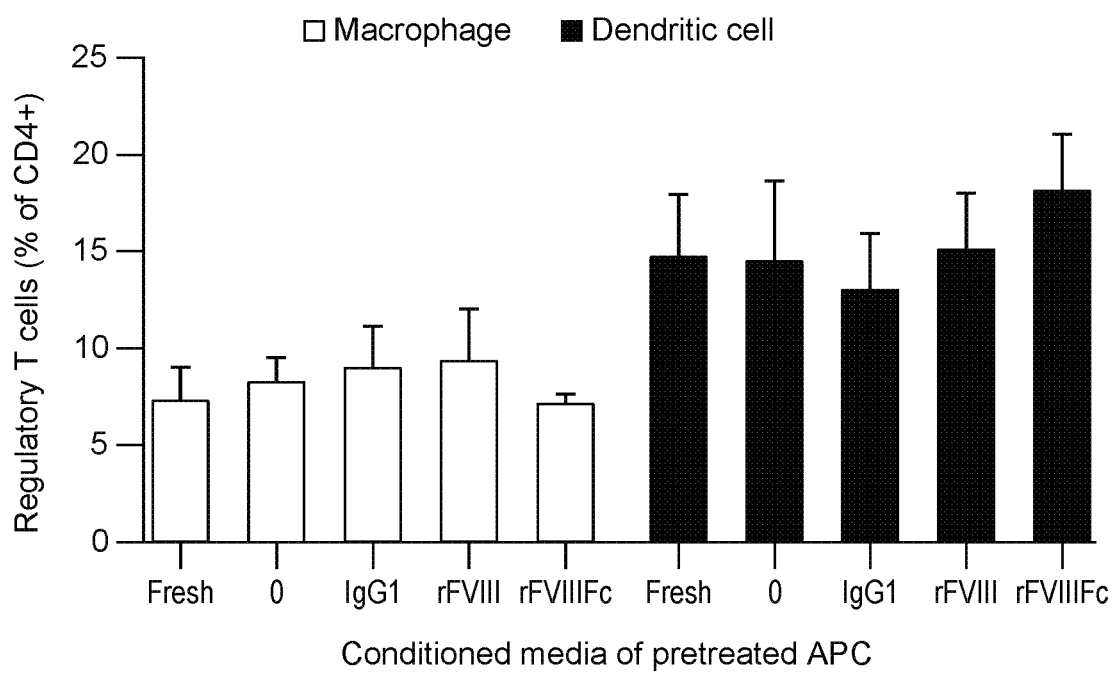
FIG. 6C is a graphical representation of the percent of regulatory T cells following culture of naïve CD4 positive T cells in the conditioned media of macrophages or dendritic cells pretreated with IgG1, FFVIII, or FFVIIIFc.

| Pathway Name | Set Size | Candidates Contained | P-value | q-value |
|---|---|---|---|---|
| Cysteine and methionine metabolism-Homo sapien (human) | 45 | 5 (11.1%) | 0.000137 | 0.00229 |
| C-MYB transcription factor network | 86 | 6 (7.0%) | 0.000389 | 0.00521 |
| Nuclear receptors meta-pathway | 316 | 11 (3.5%) | 0.000813 | 0.00908 | rFVIIIFc-treated antigen presenting cells influence regulatory T-cell differentiation that requires APC-T cell-cell contact (FIGS. 6A-6C). Peripheral blood monocyte-derived macrophages were treated with IgG1, FFVIII, or FFVIIIFc, then placed into co-culture with naïve CD4 positive T cells isolated from peripheral blood from the same donor. After six days in co-culture (FIG. 6A), the percent of regulatory T cells (CD4+ CD25+ FoxP3+) was quantified using flow cytometry (n=4) (FIG. 6B). The percent of regulatory T cells were also quantified when naïve T cells were cultured in the conditioned media of APCs pretreated with IgG1, FFVIII, or IFVIIIFc (n=4) (FIG. 6C).

Figure 7:
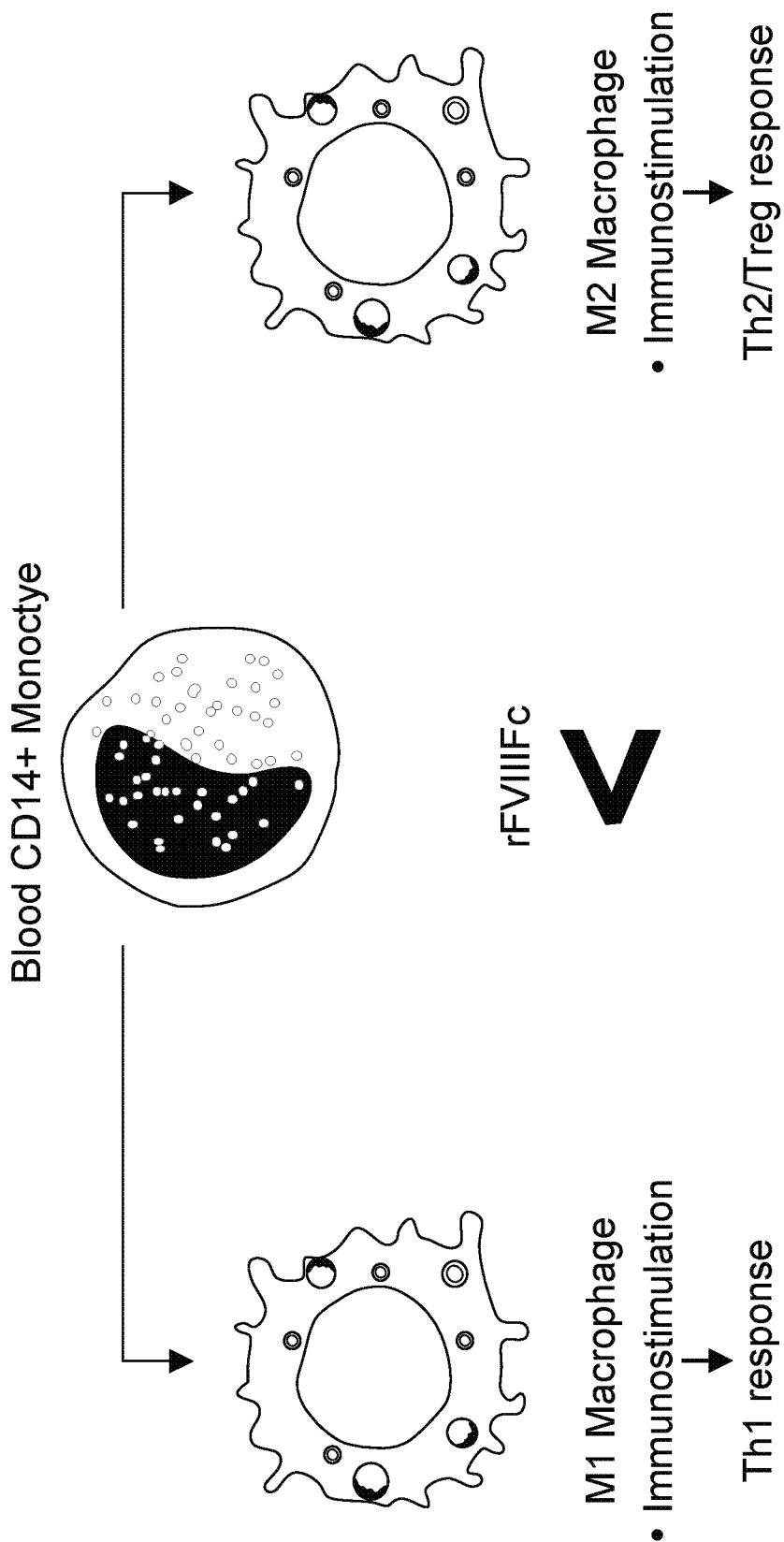
FIG. 7 is an illustration of the proposed mechanism of rFVIIIFc regulatory T-cell differentiation.

Conclusion rFVIIIFc appears to bind and induce internalization and signaling through Fcγ receptors on APCs. This signaling does not translate to proinflammatory cytokine production and does not activate the APCs (data not shown). Immunomodulatory signaling events are initiated upon rFVIIIFc treatment. These events appear to drive macrophage differentiation towards an M2-like phenotype characterized by the upregulation of NRF2 and PPARy pathways (FIG. 5H) as well as the upregulation of CD206 and arginase 1 molecules. Various other immunoregulators also showed increased expression, while at least guanylate cyclase 1 soluble subunit beta (2GUCY1B2), protoporphyrinogen oxidase (PPOX), and suppressor of cytokine signaling 3 (SOCS3) showed decreased expression in rFVIIIFc treated cells (FIG. 5H). These macrophages may execute the beneficial immunological effects previously reported, such as regulatory T-cell differentiation, FVIII tolerization, and anti-FVIII inhibitor reduction (FIG. 7).

Example 6

Early preclinical and clinical data indicate that rFVIIIFc may allow a relatively short time to negative inhibitor titre when used for ITI treatment, possibly due to immunomodulatory effects attributed to the Fc domain of the molecule. In order to obtain more robust clinical data a standardized protocol was developed. The study design is presented here.

ReITIrate (NCT03103542), a prospective, interventional, multicenter, open label study, aims to enroll 20 severe HA inhibitor patients, all ages, who failed previous ITI attempts. The primary purpose of the study is to describe the outcome of ITI performed with rFVIIIFc within a timeframe of 60 weeks. The primary endpoint will be ITI success; and the secondary endpoints assessed during ITI treatment will include time to ITI success, occurrence of relapse, number of bleeds, rFVIIIFc consumption, days of missed school or work, hospitalizations and adherence. The ITI treatment will comprise rFVIIIFc 200 IU/kg/day (once daily or divided on two daily doses) for a maximum of 60 weeks. After tolerance has been achieved, a tapering period of 16 weeks and a 32 weeks follow-up with rFVIIIFc given prophylactically follows. Success criteria will include negative inhibitor titre (<0.6 Bethesda Unit), incremental recovery >66% of expected, and terminal half-life of ≥7 hours.

Figure 8:
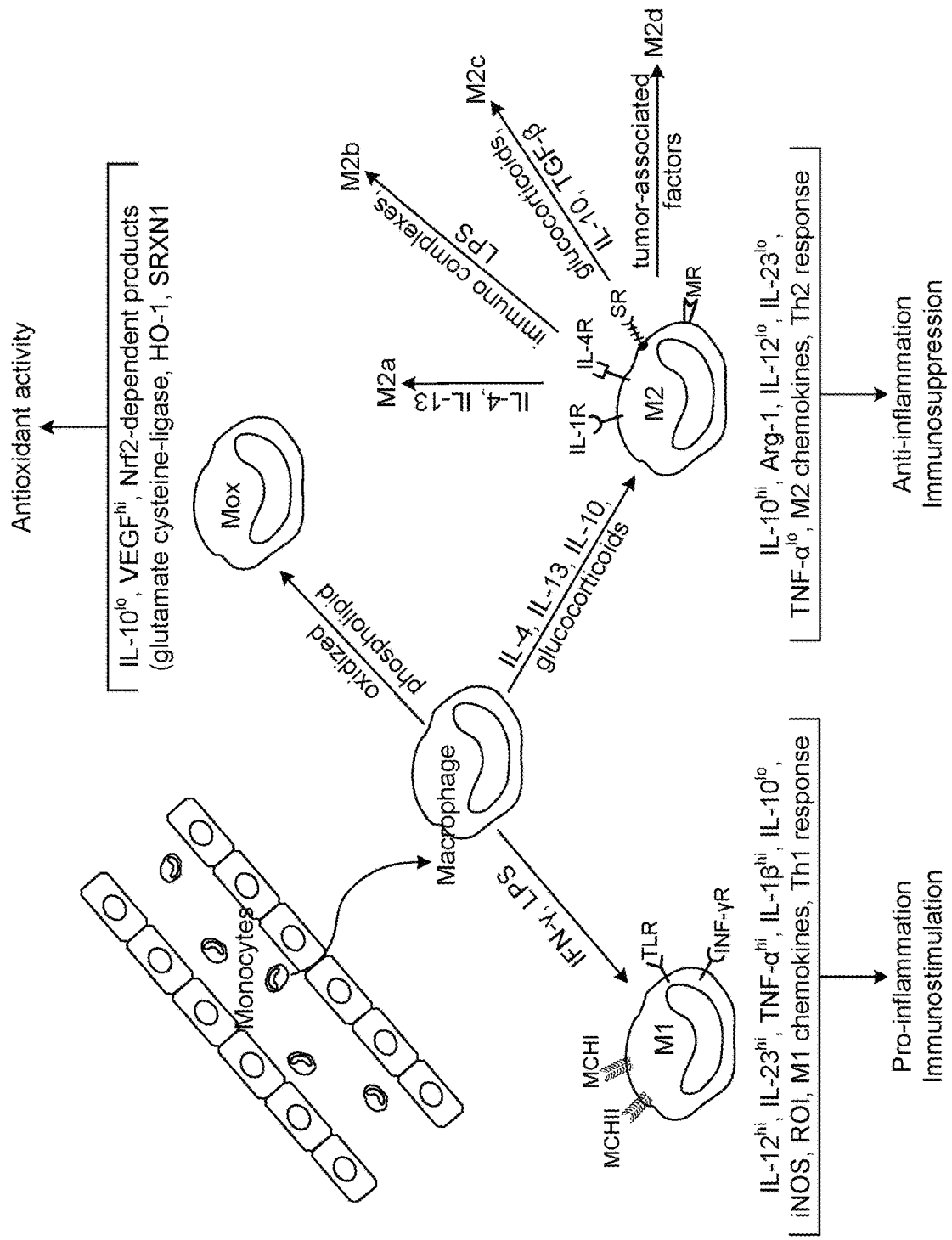
FIG. 8 is an illustration of the proposed effects of rFIXFc on macrophages.

FIG. 8 shows the proposed effects of rFIXFc on macrophages. IFVIIIFc appears to bind and to induce internalization and signaling through Fcγ receptors on APCs. This signaling does not translate to pro-inflammatory cytokine production and does not activate the APCs. Rather, immunomodulatory signaling events are initiated upon rFVIIIFc treatment. These events appear to drive macrophage differentiation towards an 'Mox/M2-like' phenotype characterized by the upregulation of NRF2 and PPARy pathways.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed is:

1. A method of treating a human with hemophilia A who has developed an inhibitory response to factor VIII (FVIII), the method comprising the following steps:
   (a) identifying a human subject who has hemophilia A and who has failed to respond to one or more previous immune tolerance therapies against FVIII,
   (b) administering between 85 IU/kg and 300 IU/kg of a chimeric protein comprising a FVIII and an Fc region (FVIII-Fc) daily to the human subject for a period sufficient to induce immune tolerance; and
   (c) following induction of immune tolerance, administering a tapering regimen of the chimeric protein to the human; and
   (d) following the tapering regimen, administering a prophylactic dose of the chimeric protein to the human; thereby reducing or eliminating an inhibitory immune response to FVIII.

2. The method of claim 1, wherein the immune tolerance is observed when titer of inhibitory antibodies in the human is less than about 0.6 Bethesda units (BU).

3. The method of claim 1, wherein the tapering regimen comprises administering a tapering dose of about 50 IU/kg to about 100 IU/kg of the chimeric protein.

4. The method of claim 3, wherein the tapering dose is administered once a day, once every other day, or three times every week.

5. The method of claim 3, wherein the tapering dose is administered for about 1 to 32 weeks.

6. The method of claim 1, wherein the tapering regimen comprises administering a tapering dose of the chimeric protein of about 50 IU/kg once a day from week 1 to week 6 following immune tolerance, or administering a tapering dose of the chimeric protein of about 100 IU/kg once a day from week 1 to week 6 following immune tolerance.

7. The method of claim 6, wherein the tapering regimen further comprises administering a tapering dose of the chimeric protein of about 50 IU/kg or about 100 IU/kg once every other day from week 6 to week 12 following immune tolerance, and/or administering a tapering dose of the chimeric protein of about 50 IU/kg or about 100 IU/kg once every other day from week 12 to week 16.

8. The method of claim 1, further comprising administering a prophylactic dose of the chimeric protein following the tapering regimen.

9. The method of claim 1, wherein time to immune tolerance is less than about 24 weeks.

10. The method of claim 1, wherein the clotting factor of the FVIII-Fc comprises a B domain deleted FVIII.

11. The method of claim 1, wherein the human has failed to respond to two previous immune tolerance therapies.

12. The method of claim 1, wherein the human has failed to respond to five previous immune tolerance therapies.

13. The method of claim 1, wherein the previous immune tolerance therapy comprises administration of one or more immunosuppressants.

14. The method of claim 1, wherein the previous immune tolerance therapy comprises a Malmo Regimen or a Bonn Protocol.

15. A method of treating a human with severe hemophilia A who has developed an inhibitory response to factor VIII (FVIII), the method comprising the following steps:
  (a) identifying a human subject who has severe hemophilia A and a historical inhibitor peak greater than or equal to (≥) 5 Bethesda units per milliliter (BU/mL), and who has failed to respond to one or more previous immune tolerance therapies against FVIII
  b) administering between 85 IU/kg and 300 IU/kg of a chimeric protein comprising a FVIII and an Fc region (FVIII-Fc) daily to the human subject for a period sufficient to induce immune tolerance; and
  (c) following induction of immune tolerance, administering a tapering regimen of the chimeric protein to the human subject; and
  (d) following the tapering regimen, administering a prophylactic dose of the chimeric protein to the human subject;
  thereby reducing or eliminating an inhibitory immune response to FVIII, wherein the human subject was diagnosed as having developed an inhibitor against FVIII at least about 24 months prior to the administering in step (b).

16. The method of claim 15, wherein the human was diagnosed as having developed an inhibitor against FVIII at least about five years prior to the administering in step (1).

17. The method of claim 15, wherein the tapering dose is administered for at least 6 weeks.

18. The method of claim 15, wherein the time to tolerance is less than 15 weeks.

19. The method of claim 15, wherein the human has a family history for developing an inhibitor immune response.

* * * * *

UNITED STATES PATENT AND TRADEMARK OFFICE
CERTIFICATE OF CORRECTION

| | | |
|---|---|---|
| PATENT NO. | : 12,257,288 B2 | Page 1 of 1 |
| APPLICATION NO. | : 16/464105 | |
| DATED | : March 25, 2025 | |
| INVENTOR(S) | : Dumont et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 638 days.

Signed and Sealed this
Sixteenth Day of December, 2025

John A. Squires
*Director of the United States Patent and Trademark Office*